(12) United States Patent
Galebach et al.

(10) Patent No.: US 11,518,725 B2
(45) Date of Patent: Dec. 6, 2022

(54) PROCESSES FOR PRODUCING ALCOHOLS FROM BIOMASS AND FURTHER PRODUCTS DERIVED THEREFROM

(71) Applicant: ExxonMobil Technology and Engineering Company, Annandale, NJ (US)

(72) Inventors: Peter H. Galebach, Madison, WI (US); Michael P. Lanci, Flemington, NJ (US); George W. Huber, Middleton, WI (US); Wenzhao Wu, Clinton, NJ (US); Ashley M. Wittrig, Houston, TX (US); Nathaniel M. Eagan, Arlington, MA (US); Paolo Andres Cuello Penaloza, Madison, WI (US); J. Scott Buchanan, Flemington, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 17/325,755

(22) Filed: May 20, 2021

(65) Prior Publication Data

US 2021/0363080 A1 Nov. 25, 2021

Related U.S. Application Data

(60) Provisional application No. 63/027,564, filed on May 20, 2020.

(51) Int. Cl.
*C07C 29/151* (2006.01)
*B01J 21/04* (2006.01)
(Continued)

(52) U.S. Cl.
CPC .......... *C07C 29/1518* (2013.01); *B01J 21/04* (2013.01); *B01J 23/06* (2013.01); *B01J 37/16* (2013.01);
(Continued)

(58) Field of Classification Search
CPC .............. C07C 29/1518; C07C 29/154; C10G 2300/1014; C10G 2300/1003; C10G 2300/4081
See application file for complete search history.

(56) References Cited

U.S. PATENT DOCUMENTS

| | | |
|---|---|---|
| 2011/0065814 A1 | 3/2011 | Matson et al. |
| 2014/0235901 A1 | 8/2014 | Gadewar et al. |
| 2019/0031585 A1 | 1/2019 | Ramasamy et al. |

FOREIGN PATENT DOCUMENTS

WO 2008/069983 A2 6/2008

OTHER PUBLICATIONS

The International Search Report and Written Opinion of PCT/US2021/033377 dated Sep. 6, 2021.
(Continued)

*Primary Examiner* — Jafar F Parsa
(74) *Attorney, Agent, or Firm* — Glenn T. Barrett

(57) ABSTRACT

Processes for producing alcohols from biomass are provided. The processes utilize supercritical methanol to depolymerize biomass with subsequent conversion to a mixture of alcohols. In particular the disclosure relates to continuous processes which produce high yields of alcohols through recycling gases and further employ dual reactor configurations which improve overall alcohol yields. Processes for producing higher ethers and olefins from the so-formed alcohols, through alcohol coupling and subsequent dehydra-
(Continued)

tion are also provided. The resulting distillate range ethers and olefins are useful as components in liquid fuels, such as diesel and jet fuel.

30 Claims, 16 Drawing Sheets

(51) Int. Cl.
    *B01J 23/06*    (2006.01)
    *B01J 37/16*    (2006.01)
    *C07C 29/154*   (2006.01)
    *C10G 11/04*    (2006.01)
    *C10G 11/18*    (2006.01)

(52) U.S. Cl.
    CPC ............ *C07C 29/154* (2013.01); *C10G 11/04* (2013.01); *C10G 11/182* (2013.01); *C10G 2300/1003* (2013.01); *C10G 2300/1014* (2013.01); *C10G 2300/4006* (2013.01); *C10G 2300/4012* (2013.01); *C10G 2300/4081* (2013.01); *C10G 2300/70* (2013.01)

(56) References Cited

OTHER PUBLICATIONS

The International Search Report and Written Opinion of PCT/US2021/033394 dated Sep. 7, 2021.
Eagan et al., "Catalytic synthesis of distillate-range ethers and olefins from ethanol through Guerbet coupling and etherification", Green Chemistry, vol. 1, No. 12, (2019), pp. 3300-3318.
Eagan et al., "Chemistries and processes for the conversion of ethanol into middle-distillate fuels", Nat. Rev. Chem., vol. 3 (2019), pp. 223-249.
Eagan et al., "Catalytic synthesis of distillate-range ethers and olefins from ethanol through Guerbet coupling and etherification". Green Chem., vol. 21 (2019), pp. 3300-3318.
Galebach et al., "Supercritical methanol depolymerization and hydrodeoxygenation of maple wood and biomass-derived oxygenates into renewable alcohols in a continuous flow reactor", ACS Sustainable Chem. Eng., vol. 7 (2019), pp. 15361-15372.
Eagan et al., "Kinetic modeling of alcohol oligomerization over calcium hydroxyapatite", ACS Catalysis, vol. 10 (2020), pp. 2978-2989.
Galebach et al., "Production of alcohols from cellulose by supercritical methanol depolymerization and hydrodeoxygenation", ACS Sustainable Chem. Eng., vol. 6 (2018), pp. 4330-4344.

PROCESSES FOR PRODUCING ALCOHOLS FROM BIOMASS AND FURTHER PRODUCTS DERIVED THEREFROM

CROSS-REFERENCE TO RELATED APPLICATIONS

This application is related to and claims the benefit of priority from U.S. Provisional Application No. 63/027,564 filed May 20, 2020, which is hereby incorporated by reference in its entirety.

FIELD OF THE INVENTION

This disclosure generally relates to processes for producing alcohols from biomass. The processes utilize supercritical methanol to depolymerize biomass with subsequent conversion to a mixture of alcohols. In particular the disclosure relates to continuous processes which produce high yields of alcohols through recycling gases and further employ dual reactor configurations which improve alcohol yields. The disclosure also relates to further processes for producing ethers and olefins from the so-formed alcohols. In particular, the disclosure also relates to processes for producing distillate range ethers and olefins, useful as components in liquid fuels, such as diesel and jet fuel.

BACKGROUND OF THE INVENTION

Biomass conversion technologies have received substantial interest as a source of fuels from renewable feedstocks like wood and agricultural residues. Thermochemical processes, such as fast pyrolysis have been studied, however they suffer from low yields to the desired liquid fuel products due to char formation or degradation reactions.

United States Patent Application Publication No. 2011/0065814 describes a catalytic method for converting biomass into fluid products including alcohols. The method uses supercritical methanol to depolymerize biomass and subsequent hydrodeoxygenation (SCM-DHDO) over a copper catalyst to $C_2$-$C_9$ alcohols with no char formation.

However, SCM-DHDO has limitations as large amounts of methanol are reformed into unreacted hydrogen, carbon monoxide, and carbon dioxide gases. In addition, SCM-DHDO has largely been studied in small scale batch reactors which are not commercially relevant.

The continuous production of alcohols from biomass using SCM-DHDO has been reported by Galebach et al in ACS Sustainable Chem. Eng., 2018, 6, 4330-4344 and 2019, 7, 15361-15372.

The production of distillate-range fuels from biomass-derived alcohols has recently received attention due to the projected increase in the demand of these fuels and the commercialization of alcohol production.

While ethanol production is commercially well established with over 25 billion barrels produced per year, its fuel applications are currently confined to gasoline with blending levels that have been historically limited to around 10 vol. % in the United States. However, the demand for gasoline is projected to decrease over the next few decades, while the demand for heavier $C_8$-$C_{22}$ distillate fuels, such as jet fuel and diesel is projected to increase.

Therefore, technologies for the conversion of ethanol into diesel and jet fuel blendstocks which can take advantage of the existing ethanol infrastructure are desirable.

Several approaches have been proposed for the conversion of ethanol to distillate fuels as recently discussed in Nat. Rev. Chem., 2019, 3, 223-249. However, the selective production of diesel blendstocks from ethanol with high cetane numbers (CNs), a measure of combustion quality, remains challenging.

The most common technologies involve acid-catalyzed ethanol dehydration to ethylene followed by olefin oligomerization with solid acids or transition metals. While dehydration and oligomerization can be performed in a single reactor when using acid catalysis, ethylene oligomerization is slow and necessitates operation at temperatures above 300° C. where the more highly reactive products (resulting from their increased substitution) can be rapidly converted through undesirable side-reactions including cracking, hydrogen transfer, and aromatization. As a result, such processes are limited to producing mainly C3-C8 paraffins and C6-C12 aromatics, species more suitable for use in gasoline or in the chemical industry (e.g. BTEX).

Alternatively, transition metals can be used to catalyze ethylene oligomerization selectively at lower temperatures. The olefins produced obey statistically-constrained Schulz-Flory distributions which limit ethylene to be at most 63 C % selective to the distillate range (C8-C22) and at most 51 C % selective to specifically the diesel range (C10-C22) in single-pass conversion. Typically, this oligomerization also involves homogeneous catalysts, organic solvents, and alkylating agents which require downstream separation processes.

Supported Ni and Co catalysts have shown promise as heterogeneous alternatives, though the same mechanisms lead to similar limitations.

To overcome the limitations of these two oligomerization chemistries, they can be combined in series such that transition metals are used to convert ethylene to C4-C6 olefin mixtures that can be oligomerized using solid acids without significant side-reactions. The latter stage promotes the formation of branched oligomers, which can be beneficial for cold flow properties, but detrimental to cetane number.

An alternative oligomerization chemistry which can be performed in a single step and introduces branching in a more predictable manner is Guerbet coupling. This coupling reaction formally involves three reactions performed in a single catalytic system: (1) dehydrogenation of two alcohols to aldehydes, (2) aldol condensation to an alkenal, and (3) hydrogenation to a saturated alcohol. The product alcohol can then undergo continued condensation reactions with another alcohol present in the system. United States Patent Application Publication No. 20190031585 describes a method and copper MgO-$Al_2O_3$ catalyst for converting ethanol to higher alcohols.

Ethers possess high cetane numbers and can be produced selectively from the acid-catalyzed etherification of linear primary alcohols.

Eagan et al have reported the synthesis of distillate-range ethers and olefins from ethanol through Guerbet coupling and etherification (Green Chem., 2019, 21, 3300-3318). A calcium hydroxyapatite catalyst was used to effect the Guerbet coupling.

In view of the foregoing there is a need to provide improved processes for the conversion of biomass to alcohols and, additionally, for the production of distillate range ethers and olefins from the so-formed alcohols. The present disclosure addresses, at least in part, these needs.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY OF THE INVENTION

The present disclosure relates to novel processes for producing alcohols from biomass and optional further conversion of the alcohols to ethers and olefins, which in turn may be utilized in liquid fuel formulation or further upgraded to components suitable for liquid fuel formulation.

Alcohols from Biomass

In one aspect the present disclosure provides a process for producing alcohols from biomass, the process comprising:

(a) contacting biomass and methanol with catalyst (A) in reactor (A) under conditions effective to produce an effluent comprising a mixture of alcohols;

(b) separating the effluent from reactor (A) into at least two alcohol rich streams and a gas stream comprising carbon monoxide and hydrogen, wherein at least one alcohol rich stream comprises methanol;

(c) recycling at least a portion of the at least one alcohol rich stream comprising methanol to the reactor (A) and/or a feed to reactor (A); and, one or both of steps (d) and (e);

(d) recycling at least a portion of the gas stream comprising carbon monoxide and hydrogen to reactor (A) and/or a feed to reactor (A);

(e) contacting at least a portion of the gas stream comprising carbon monoxide and hydrogen with catalyst (B) in reactor (B) under conditions effective to produce methanol and subsequently feeding at least a portion of the so-formed methanol to reactor (A) and/or a feed to reactor (A).

The biomass and methanol may be introduced into reactor (A) in a number of ways.

In one embodiment the biomass may be pre-mixed with methanol so as to disperse or solubilize the biomass in the methanol prior to feeding to reactor (A). The degree of solubilization will depend on the nature of the biomass, the concentration of biomass in the methanol and the temperature.

In another embodiment the biomass may be pre-mixed with a suitable fluid so as to disperse or solubilize the biomass prior to feeding to reactor (A). The degree of solubilization will depend on the nature of the biomass, the concentration of biomass in the fluid and the temperature.

In this embodiment the methanol may be separately fed to reactor (A).

In some embodiments, the fluid comprises one or more of methanol, ethanol and an inert fluid, such as a saturated hydrocarbon.

Suitable fluids comprise, but are not limited to, inert fluids such as pentane or other saturated hydrocarbons.

In other embodiments, higher alcohols, such as ethanol, may be mixed with the biomass and the resulting mixture comprising biomass and higher alcohol fed to reactor (A). In this embodiment the methanol may be separately fed to reactor (A).

In other embodiments a mixture comprising biomass, methanol and one or more higher alcohols may be fed to reactor (A).

In some embodiments, the fluid comprises one or more of methanol, ethanol and an inert fluid, such as a saturated hydrocarbon.

In some embodiments, the biomass is solubilized under conditions of elevated temperature, for example, temperatures greater than about 20° C. The process of solubilizing the biomass, at elevated temperatures, may partially depolymerize the biomass in the absence of catalyst. In the presence of catalyst the biomass is further depolymerized, but also undergoes hydrodeoxygenation and other reactions, for example, retro-aldol condensations, dehydrations, hydrogenations, and aldol reactions.

The weight percent biomass in reactor (A) may be at least about 5 wt. %, or at least about 10 wt. %, or at least about 15 wt. %, or at least about 20 wt. %, based on the total weight of feed components to reactor (A).

In some embodiments, catalyst (A) comprises one or more metals supported on one or more metal oxides. The one or more metals may comprise one or more of Cu, Pd, Pt, Ni and Ru, and the one or more metal oxides may comprise one or more of MgO, CaO, SrO, BaO, CeO, $Al_2O_3$, $SiO_2$, $ZrO_2$, and $TiO_2$.

In some embodiments catalyst (A) comprises one or more of Cu and Pd supported on a metal oxide comprising MgO and $Al_2O_3$.

In some embodiments catalyst (A) is reduced prior to contacting with biomass and methanol.

In some embodiments the contacting in step (a) is performed at about 280° C. to about 350° C.

In some embodiments the pressure in reactor (A) is between about 500 psi (3.45 MPa) and about 5000 psi (34.5 MPa).

In some embodiments the pressure in reactor (A) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

In some embodiments the pressure in reactor (A) is less than 2000 psi (13.8 MPa).

In some preferred embodiments, prior to step (b), at least a portion of the effluent from the reactor (A) is contacted with catalyst (C) in reactor (C) under conditions effective to produce methanol from carbon monoxide and hydrogen.

In some embodiments catalyst (C) comprises one or more metals supported on one or more metal oxides. The one or more metals may comprise one or more of Cu, Pd, Pt, Ni and Ru, and the one or more metal oxides may comprise one or more of MgO, CaO, ZnO, SrO, BaO, CeO, $Al_2O_3$, $SiO_2$, $ZrO_2$, and $TiO_2$.

In some embodiments catalyst (C) comprises Cu supported on a metal oxide comprising ZnO and $Al_2O_3$.

In some embodiments catalyst (C) is reduced prior to use.

Advantageously, the temperature of contacting with catalyst (C) is preferably lower than the temperature of contacting with catalyst (A).

In some embodiments the contacting with catalyst (C) is performed at about 240° C. to about 300° C.

In some embodiments the pressure in reactor (C) is between about 500 psi (3.45 MPa) and about 5000 psi (34.5 MPa).

In some embodiments the pressure in reactor (C) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

In some embodiments the pressure in reactor (C) is less than 2000 psi (13.8 MPa).

In step (e) catalyst (B) comprises one or more metals supported on one or more metal oxides. The one or more metals may comprise one or more of Cu, Pd, Pt, Ni and Ru, and the one or more metal oxides may comprise one or more of MgO, CaO, ZnO, SrO, BaO, CeO, $Al_2O_3$, $SiO_2$, $ZrO_2$, and $TiO_2$.

In some embodiments catalyst (B) comprises Cu supported on a metal oxide comprising ZnO and $Al_2O_3$.

In some embodiments catalyst (B) is reduced prior to use.

In some embodiments the contacting with catalyst (B) is performed at about 240° C. to about 350° C.

In some embodiments the pressure in reactor (B) is between about 500 psi (3.45 MPa) and about 5000 psi (34.5 MPa).

In some embodiments the pressure in reactor (B) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

Prior to step (d) or step (e), the gas stream comprising carbon monoxide and hydrogen may be treated to remove at least a portion of carbon dioxide.

In some embodiments the process further comprises feeding a make-up stream of carbon monoxide and hydrogen to reactor (A) and/or to any one or more of the feeds to reactor (A). For example, the make-up stream of carbon monoxide and hydrogen may be directly fed to the reactor (A). Alternatively, or additionally, the make-up stream of carbon monoxide and hydrogen may be fed to the biomass/methanol mixture, biomass/fluid mixture and/or methanol, and the resulting streams fed to the reactor (A).

In some embodiments the process further comprises feeding a make-up stream of carbon monoxide and hydrogen to reactor (C).

In some embodiments the process further comprises feeding a make-up stream of carbon monoxide and hydrogen to reactor (C) and/or to any one or more of the feeds to reactor (C). For example, the make-up stream of carbon monoxide and hydrogen may be directly fed to reactor (C). Alternatively, or additionally, the make-up stream of carbon monoxide and hydrogen may be fed to the effluent from reactor (A) prior to feeding to reactor (C).

In some embodiments the process further comprises feeding a make-up stream of carbon monoxide and hydrogen to reactor (B).

In some embodiments the process further comprises feeding a make-up stream of carbon monoxide and hydrogen to reactor (B) and/or to any one or more of the feeds to reactor (B). For example, the make-up stream of carbon monoxide and hydrogen may be directly fed to reactor (B). Alternatively, or additionally, the make-up stream of carbon monoxide and hydrogen may be fed to the gas stream prior to feeding to reactor (B).

In some embodiments at least a portion of the make-up stream of carbon monoxide and hydrogen is derived from the gasification of biomass.

In some embodiments the make-up stream of carbon monoxide and hydrogen is rich in hydrogen.

In other embodiments the make-up stream of carbon monoxide and hydrogen is rich in carbon monoxide.

In some embodiments the alcohol rich stream comprising methanol substantially comprises methanol. In these embodiments the methanol content of the alcohol rich stream comprising methanol is preferably greater than 90% by weight based on the total weight of the alcohol rich stream comprising methanol.

In other embodiments the alcohol rich stream comprising methanol further comprises $C_2$ to $C_4$ alcohols.

In some embodiments, in step (b), the mixture of alcohols is separated into three or more alcohol rich streams. These alcohol rich streams may be utilized for further upgrading.

In some embodiments the alcohol rich stream comprising methanol is first contacted with biomass, prior to feeding to reactor (A), to solubilize at least some of the biomass, and the resulting biomass/methanol mixture fed to reactor (A).

In some embodiments a stream comprising biomass and methanol are fed to reactor (A) after a period of time during which only carbon monoxide and hydrogen are fed to reactor (A), wherein during said period of time the carbon monoxide and hydrogen produce methanol.

Advantageously, this embodiment may represent a suitable start-up procedure for the process, such that methanol may be present in reactor (A) when biomass is first introduced.

In some embodiments, the process further comprises the step of recycling at least part of the effluent from reactor (A) back to reactor (A). This recycling occurs prior to separation step (b). Preferably, prior to recycling back to reactor (A), the effluent is first treated so as to remove gases, such as carbon dioxide, carbon monoxide and/or hydrogen.

Advantageously, recycling the effluent from reactor (A) concentrates the higher alcohols prior to separation step (b), lowering the energy requirements for separation.

In embodiments, the biomass comprises one or more of manure, agricultural residues, energy crops, wood, wood wastes, food waste, municipal waste, paper waste, cardboard waste, cellulose, seed or vegetable oil, sugar cane bagasse, corn stover, straws, grasses and chitin.

In another aspect the present disclosure provides a process for producing alcohols from biomass, the process comprising:

(a) contacting biomass and methanol with catalyst (A) in reactor (A) under conditions effective to produce an effluent comprising a mixture of alcohols;

(b) contacting the effluent from reactor (A) with catalyst (C) in reactor (C) under conditions effective to produce methanol from carbon monoxide and hydrogen;

(c) separating effluent from reactor (C) into at least two alcohol rich streams and a gas stream comprising carbon monoxide and hydrogen, wherein at least one alcohol rich stream comprises methanol;

(d) recycling at least a portion of the at least one alcohol rich stream comprising methanol to reactor (A) and/or a feed to reactor (A); and, one or both of steps (e) and (f);

(e) recycling at least a portion of the gas stream comprising carbon monoxide and hydrogen to reactor (C);

(f) contacting at least a portion of the gas stream comprising carbon monoxide and hydrogen with a catalyst (B) in reactor (B) under conditions effective to produce methanol and subsequently feeding at least a portion of the so-formed methanol to reactor (A) and/or a feed to reactor (A).

The biomass and methanol may be introduced into the reactor (A) in a number of ways.

In one embodiment the biomass may be pre-mixed with methanol so as to disperse or solubilize the biomass in the methanol prior to feeding to reactor (A). The degree of solubilization will depend on the nature of the biomass, the concentration of biomass in the methanol and the temperature.

In one embodiment the biomass may be pre-mixed with a suitable fluid so as to disperse or solubilize the biomass prior to feeding to reactor (A). The degree of solubilization will depend on the nature of the biomass, the concentration of biomass in the fluid and the temperature.

In this embodiment the methanol may be separately fed to reactor (A).

In some embodiments, the fluid comprises one or more of methanol, ethanol and an inert fluid, such as a saturated hydrocarbon.

Suitable fluids comprise, but are not limited to, inert fluids such as pentane or other saturated hydrocarbons.

In another embodiment the biomass may be pre-mixed with the methanol so as to disperse or solubilize the biomass prior to feeding to reactor (A). The degree of solubilization will depend on the nature of the biomass, the concentration of biomass in the methanol and the temperature.

In other embodiments, higher alcohols, such as ethanol, may be mixed with the biomass and the resulting mixture comprising biomass and higher alcohol fed to reactor (A). In this embodiment the methanol may be separately fed to reactor (A).

In other embodiments a mixture comprising biomass, methanol and one or more higher alcohols may be fed to reactor (A).

In some embodiments, the biomass is solubilized under conditions of elevated temperature, for example, temperatures greater than about 20° C. The process of solubilizing the biomass, at elevated temperatures, may partially depolymerize the biomass in the absence of catalyst. In the presence of catalyst the biomass is further depolymerized, but also undergoes hydrodeoxygenation and other reactions, for example, retro-aldol condensations, dehydrations, hydrogenations, and aldol reactions.

The weight percent biomass in reactor (A) may be at least about 5 wt. %, or at least about 10 wt. %, or at least about 15 wt. %, or at least about 20 wt. %, based on the total weight of feed components to reactor (A).

In some embodiments catalyst (A) comprises one or more metals supported on one or more metal oxides. The one or more metals may comprise one or more of Cu, Pd, Pt, Ni and Ru, and the one or more metal oxides may comprise one or more of MgO, CaO, SrO, BaO, CeO, $Al_2O_3$, $SiO_2$, $ZrO_2$, and $TiO_2$.

In some embodiments catalyst (A) may comprise one or more of Cu and Pd supported on a metal oxide comprising MgO and $Al_2O_3$.

In some embodiments catalyst (A) is reduced prior to contacting with biomass and methanol.

In some embodiments the contacting in step (a) is performed at about 280° C. to about 350° C.

In some embodiments the pressure in reactor (A) is between about 500 psi (3.45 MPa) and about 5000 psi (34.5 MPa).

In some embodiments the pressure in reactor (A) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

In some embodiments the pressure in reactor (A) is less than 2000 psi (13.8 MPa).

In some embodiments catalyst (C) comprises one or more metals supported on one or more metal oxides. The one or more metals may comprise one or more of Cu, Pd, Pt, Ni and Ru, and the one or more metal oxides may comprise one or more of MgO, CaO, ZnO, SrO, BaO, CeO, $Al_2O_3$, $SiO_2$, $ZrO_2$, and $TiO_2$.

In some embodiments catalyst (C) may comprise Cu supported on a metal oxide comprising ZnO and $Al_2O_3$.

In some embodiments catalyst (C) is reduced prior to use.

Advantageously, the temperature of contacting with catalyst (C) is preferably lower than the temperature of contacting with catalyst (A).

In some embodiments the contacting with catalyst (C) is performed at about 240° C. to about 300° C.

In some embodiments the pressure in reactor (C) is between about 500 psi (3.45 MPa) and about 5000 psi (34.5 MPa).

In some embodiments the pressure in reactor (C) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

In some embodiments the pressure in reactor (C) is less than 2000 psi (13.8 MPa).

In step (f) in reactor (B), catalyst (B) comprises one or more metals supported on one or more metal oxides. The one or more metals may comprise one or more of Cu, Pd, Pt, Ni and Ru, and the one or more metal oxides may comprise one or more of MgO, CaO, ZnO, SrO, BaO, CeO, $Al_2O_3$, $SiO_2$, $ZrO_2$, and $TiO_2$.

In some embodiments catalyst (B) comprises Cu supported on a metal oxide comprising ZnO and $Al_2O_3$.

In some embodiments catalyst (B) is reduced prior to use.

In some embodiments the contacting with catalyst (B) is performed at about 240° C. to about 350° C.

In some embodiments the pressure in reactor (B) is between about 500 psi (3.45 MPa) and about 5000 psi (34.5 MPa).

In some embodiments the pressure in reactor (B) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

In some embodiments, prior to step (e) or (f), the gas stream comprising carbon monoxide and hydrogen is treated to remove at least a portion of carbon dioxide.

In some embodiments the process further comprises feeding a make-up stream of carbon monoxide and hydrogen to reactor (A).

In some embodiments the process further comprises feeding a make-up stream of carbon monoxide and hydrogen to reactor (A) and/or to any one or more of the feeds to reactor (A). For example, the make-up stream of carbon monoxide and hydrogen may be directly fed to reactor (A). Alternatively, or additionally, the make-up stream of carbon monoxide and hydrogen may be fed to the biomass/methanol mixture, biomass/fluid mixture and/or the methanol, and the resulting streams fed to reactor (A).

In some embodiments the process further comprises feeding a make-up stream of carbon monoxide and hydrogen to reactor (C).

In some embodiments the process further comprises feeding a make-up stream of carbon monoxide and hydrogen to reactor (C) and/or to any one or more of the feeds to reactor (C). For example, the make-up stream of carbon monoxide and hydrogen may be directly fed to reactor (C). Alternatively, or additionally, the make-up stream of carbon monoxide and hydrogen may be fed to the effluent from reactor (A) prior to feeding to reactor (C).

In some embodiments the process further comprises feeding a make-up stream of carbon monoxide and hydrogen to reactor (B).

In some embodiments the process further comprises feeding a make-up stream of carbon monoxide and hydrogen to reactor (B) and/or to any one or more of the feeds to reactor (B). For example, the make-up stream of carbon monoxide and hydrogen may be directly fed to reactor (B). Alternatively, or additionally, the make-up stream of carbon monoxide and hydrogen may be fed to the gas stream prior to feeding to reactor (B).

In some embodiments at least a portion of the make-up stream of carbon monoxide and hydrogen is derived from the gasification of biomass.

In some embodiments the make-up stream of carbon monoxide and hydrogen is rich in hydrogen.

In other embodiments the make-up stream of carbon monoxide and hydrogen is rich in carbon monoxide.

In some embodiments the alcohol rich stream comprising methanol substantially comprises methanol. In these embodiments the methanol content of the alcohol rich stream comprising methanol is preferably greater than 90% by weight based on the total weight of the alcohol rich stream comprising methanol.

In other embodiments the alcohol rich stream comprising methanol further comprises $C_2$ to $C_4$ alcohols.

In some embodiments, in step (b), the mixture of alcohols is separated into three or more alcohol rich streams. These alcohol rich streams may be utilized for further upgrading.

In some embodiments the alcohol rich stream comprising methanol is first contacted with biomass, prior to feeding to reactor (A), to solubilize at least some of the biomass, and the resulting biomass/methanol mixture fed to reactor (A).

In some embodiments the biomass and methanol are fed to reactor (A) after a period of time during which only carbon monoxide and hydrogen are fed to reactor (A), wherein during said period of time the carbon monoxide and hydrogen produce methanol.

Advantageously, this embodiment may represent a suitable start-up procedure for the process, such that methanol may be present in reactor (A) when biomass is first introduced.

In some embodiments the process further comprises the step of recycling at least part of the effluent from one or both reactor (A) and reactor (C) back to reactor (A). This recycling occurs prior to step (b) and/or prior to step (c). Preferably, prior to recycling back to reactor (A) and/or reactor (C), the effluent is first treated so as to remove gases, such as carbon dioxide, carbon monoxide and/or hydrogen.

Advantageously, this recycling concentrates the higher alcohols prior to step (b) and/or step (c), lowering the energy requirements for separation in step (c).

In embodiments, the biomass comprises one or more of manure, agricultural residues, energy crops, wood, wood wastes, food waste, municipal waste, paper waste, cardboard waste, cellulose, seed or vegetable oil, sugar cane bagasse, corn stover, straws, grasses and chitin.

Ethers and Olefins from Biomass

In another aspect the present disclosure provides a process for producing ethers and olefins from biomass, the process comprising:

a) contacting biomass and methanol with catalyst (A) in reactor (A) under conditions effective to produce a first effluent comprising a mixture of alcohols;

b) contacting at least a portion of the first effluent comprising a mixture of alcohols with a catalyst (D) in reactor (D) under conditions effective to produce a second effluent comprising higher alcohols; and c) contacting at least a portion of the second effluent comprising higher alcohols with a catalyst (E) in reactor (E) under conditions effective to dehydrate at least a portion of the higher alcohols to ethers and olefins.

The biomass and methanol may be introduced into the reactor (A) in a number of ways.

In one embodiment the biomass may be pre-mixed with methanol so as to disperse or solubilize the biomass in the methanol prior to feeding to reactor (A). The degree of solubilization will depend on the nature of the biomass, the concentration of biomass in the methanol and the temperature.

In one embodiment the biomass may be pre-mixed with a suitable fluid so as to disperse or solubilize the biomass prior to feeding to reactor (A). The degree of solubilization will depend on the nature of the biomass, the concentration of biomass in the fluid and the temperature.

In this embodiment the methanol may be separately fed to reactor (A).

In some embodiments, the fluid comprises one or more of methanol, ethanol and an inert fluid, such as a saturated hydrocarbon.

Suitable fluids comprise, but are not limited to, inert fluids such as pentane or other saturated hydrocarbons.

In another embodiment the biomass may be pre-mixed with the methanol so as to disperse or solubilize the biomass prior to feeding to reactor (A). The degree of solubilization will depend on the nature of the biomass, the concentration of biomass in the methanol and the temperature.

In other embodiments, higher alcohols, such as ethanol, may be mixed with the biomass and the resulting mixture comprising biomass and higher alcohol fed to reactor (A). In this embodiment the methanol may be separately fed to reactor (A).

In other embodiments a mixture comprising biomass, methanol and one or more higher alcohols may be fed to reactor (A).

In some embodiments, the biomass is solubilized under conditions of elevated temperature, for example, temperatures greater than about 20° C. The process of solubilizing the biomass, at elevated temperatures, may partially depolymerize the biomass in the absence of catalyst. In the presence of catalyst the biomass is further depolymerized, but also undergoes hydrodeoxygenation and other reactions, for example, retro-aldol condensations, dehydrations, hydrogenations, and aldol reactions.

The weight percent biomass in reactor (A) may be at least about 5 wt. %, or at least about 10 wt. %, or at least about 15 wt. %, or at least about 20 wt. %, based on the total weight of feed components to reactor (A).

In some embodiments catalyst (A) comprises one or more metals supported on one or more metal oxides. The one or more metals may comprise one or more of Cu, Pd, Pt, Ni and Ru, and the one or more metal oxides may comprise one or more of MgO, CaO, SrO, BaO, CeO, $Al_2O_3$, $SiO_2$, $ZrO_2$, and $TiO_2$.

In some embodiments catalyst (A) may comprise one or more of Cu and Pd supported on a metal oxide comprising MgO and $Al_2O_3$.

In some embodiments catalyst (A) is reduced prior to contacting with biomass and methanol.

In some embodiments, the contacting in step (a) is performed at about 280° C. to about 350° C.

In some embodiments, the pressure in reactor (A) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

The process may further comprise:

(i) separating the effluent from reactor (A) into at least two alcohol rich streams and a gas stream comprising carbon monoxide and hydrogen, wherein at least one alcohol rich stream comprises methanol; and (ii) recycling at least a portion of the at least one alcohol rich stream comprising methanol to reactor (A) and/or a feed to reactor (A).

The process may further comprise one or both of the following (i) and (ii):

(i) recycling at least a portion of the gas stream comprising carbon monoxide and hydrogen to reactor (A) and/or a feed to reactor (A);

(ii) contacting at least a portion of the gas stream comprising carbon monoxide and hydrogen with catalyst (B) in reactor (B) under conditions effective to produce methanol, and subsequently feeding at least a portion of the so-formed methanol to reactor (A) and/or a feed to reactor (A).

Catalyst (B) may comprise one or more metals supported on one or more metal oxides.

The one or more metals may comprise one or more of Cu, Pd, Pt, Ni and Ru, and the one or more metal oxides may comprise one or more of MgO, CaO, ZnO, SrO, BaO, CeO, $Al_2O_3$, $SiO_2$, $ZrO_2$, and $TiO_2$.

In some embodiments catalyst (B) comprises Cu supported on a metal oxide comprising ZnO and $Al_2O_3$.

In some embodiments catalyst (B) is reduced prior to use.

In some embodiments the contacting with catalyst (B) is performed at about 240° C. to about 350° C.

In some embodiments the pressure in reactor (B) is between about 500 psi (3.45 MPa) and about 5000 psi (34.5 MPa).

In some embodiments the pressure in reactor (B) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

In some embodiments, prior to step (b), at least a portion of the effluent from reactor (A) is contacted with catalyst (C) in a reactor (C) under conditions effective to produce methanol from carbon monoxide and hydrogen.

In some embodiments catalyst (C) comprises one or more metals supported on one or more metal oxides. The one or more metals may comprise one or more of Cu, Pd, Pt, Ni and Ru, and the one or more metal oxides may comprise one or more of MgO, CaO, ZnO, SrO, BaO, CeO, $Al_2O_3$, $SiO_2$, $ZrO_2$, and $TiO_2$.

In some embodiments catalyst (C) may comprise Cu supported on a metal oxide comprising ZnO and $Al_2O_3$.

In some embodiments the catalyst (C) is reduced prior to use.

In some embodiments, the contacting with the catalyst (C) is performed at about 240° C. to about 300° C.

In some embodiments, prior to step (a) or step (b), the gas stream comprising carbon monoxide and hydrogen is treated to remove at least a portion of carbon dioxide.

In some embodiments the process further comprises feeding a make-up stream of carbon monoxide and hydrogen to reactor (A).

In some embodiments the process further comprises feeding a make-up stream of carbon monoxide and hydrogen to reactor (A) and/or to any one or more of the feeds to reactor (A). For example, the make-up stream of carbon monoxide and hydrogen may be directly fed to reactor (A). Alternatively, or additionally, the make-up stream of carbon monoxide and hydrogen may be fed to the biomass/methanol mixture, biomass/fluid mixture and/or the methanol, and the resulting streams fed to reactor (A).

In some embodiments the process further comprises feeding a make-up stream of carbon monoxide and hydrogen to reactor (C).

In some embodiments the process further comprises feeding a make-up stream of carbon monoxide and hydrogen to reactor (C) and/or to any one or more of the feeds to reactor (C). For example, the make-up stream of carbon monoxide and hydrogen may be directly fed to reactor (C). Alternatively, or additionally, the make-up stream of carbon monoxide and hydrogen may be fed to the effluent from reactor (A) prior to feeding to reactor (C).

In some embodiments the process further comprises feeding a make-up stream of carbon monoxide and hydrogen to reactor (B).

In some embodiments the process further comprises feeding a make-up stream of carbon monoxide and hydrogen to reactor (B) and/or to any one or more of the feeds to reactor (B). For example, the make-up stream of carbon monoxide and hydrogen may be directly fed to reactor (B). Alternatively, or additionally, the make-up stream of carbon monoxide and hydrogen may be fed to the gas stream prior to feeding to reactor (B).

In some embodiments at least a portion of the make-up stream of carbon monoxide and hydrogen is derived from the gasification of biomass.

In some embodiments the make-up stream of carbon monoxide and hydrogen is rich in hydrogen.

In other embodiments the make-up stream of carbon monoxide and hydrogen is rich in carbon monoxide.

In some embodiments, the alcohol rich stream comprising methanol substantially comprises methanol.

In other embodiments, the alcohol rich stream comprising methanol further comprises C2 to C4 alcohols.

In some embodiments, the mixture of alcohols from step (a) is separated into three or more alcohol rich streams.

In some embodiments, the alcohol rich stream comprising methanol is first contacted with biomass, to solubilize at least a portion of the biomass, prior to feeding the resulting mixture to reactor (A).

In some embodiments, biomass and methanol are fed to reactor (A) after a period of time during which only carbon monoxide and hydrogen are fed to reactor (A), wherein during said period of time the carbon monoxide and hydrogen produce methanol.

In some embodiments the process further comprises the step of recycling at least a portion of the effluent from reactor (A) back to reactor (A).

In some embodiments, the biomass comprises one or more of agricultural residues, energy crops, wood, wood wastes, food waste, municipal solid waste, cellulose, sugar cane bagasse, corn stover, and chitin.

In some embodiments, the selectivity to mono-alcohols in the effluent from reactor (A) is at least about 30%.

In some embodiments, the selectivity to mono-alcohols in an effluent from reactor (C) is at least about 30%.

In some embodiments, the weight percent biomass in reactor (A) is at least 10 wt. % based on the total weight of feed components to reactor (A) and the selectivity to monoalcohols in the effluent from reactor (A) is at least about 30%.

In some embodiments, at least a portion of the mixture of alcohols contacted with catalyst (D) in step (b) comprise primary alcohols.

In some embodiments, the primary alcohols comprise one or more C2 to C5 alcohols.

In some embodiments, the primary alcohols comprise one or more of ethanol and 1-butanol.

In some embodiments, the contacting in step (b) is performed in the presence of one or more of hydrogen and inert gas.

In some embodiments, the higher alcohols produced in step (b) comprise one or more C4+ alcohols.

In embodiments, step (b) is performed at a temperature from about 250° C. to about 370° C., preferably from about 280° C. to about 350° C.

Step (b) may be performed at a pressure from about 15 psi (0.1 MPa) to about 1000 psi (6.9 MPa), or from about 100 psi (0.69 MPa) to about 1000 psi (6.9 MPa), or from about 200 psi (1.38 MPa) to about 500 psi (3.45 MPa).

In step (b), the partial pressure of hydrogen may be less than 100 psi (0.69 MPa), or less than 90 psi (0.62 MPa), or less than 80 psi (0.55 MPa) or less than 70 psi (0.48 MPa), or less than 60 psi (0.41 MPa).

In some embodiments, catalyst (D) is a heterogeneous catalyst comprising one or more Group A oxides, said Group A oxides being oxides of Mg, Ca, Zn, Mn, Sr, Si and Zr; one or more Group B oxides, said Group B oxides being one or more oxides of Al, La, Ga, Ce, Fe, Sc, Cr, P and V; and combinations of both Group A and Group B oxides, and, optionally, one or more of Cu, Ni, Pt, Pd, Rh, Co, Cs and Rb.

Catalyst (D) may be a heterogeneous catalyst comprising one or more oxides of Mg, Ca, Zn, Sr, Al and Ce.

Catalyst (D) may be a heterogeneous catalyst comprising one or more oxides of Mg, Ca and Zn, one or more oxides of Al, La, Ga, Ce, Fe and Cr, and one or more of Cu, Ni, Pt, Pd, Rh and Co.

Catalyst (D) may be a heterogeneous catalyst comprising one or more oxides of Mg, Ca and Sr, one or more of P and V, and, optionally, one or more of Cu, Ni, Pt, Pd, Rh, and Co.

Catalyst (D) may be a heterogeneous catalyst comprising Al and Si metal oxides and one or more of Cs and Rb.

The weight percent of the one or more of Cu, Ni, Pt, Pd, Rh and Co in catalyst (D) may be up to about 10 wt. %, or from about 0.01 wt. % to about 9 wt. %, or from about 0.01 wt. % to about 8 wt. %, or from about 0.01 wt. % to about 7 wt. %, or from about 0.01 wt. % to about 6 wt. %, or from about 0.01 wt. % to about 5 wt. %, or from about 0.01 wt. % to about 4 wt. %, or from about 0.01 wt. % to about 3 wt. %, or from about 0.01 wt. % to about 2 wt. %, or from about 0.01 wt. % to about 1 wt. %, or from about 0.01 wt. % to about 0.5 wt. %, or from about 0.01 wt. % to about 0.4 wt. %, or from about 0.01 wt. % to about 0.3 wt. %, or from about 0.01 wt. % to about 0.2 wt. %, or from about 0.01 wt. % to about 0.1 wt. %, based on the total weight of the catalyst.

Catalyst (D) may comprise Mg and Al oxides and Cu and the weight percent of Cu is preferably 0.05 wt. % to 1.0 wt. %, or 0.05 wt. % to 0.5 wt. %, or 0.05 wt. % to 0.2 wt. %, based on the total weight of the catalyst.

Preferably, catalyst (D) is reduced prior to use.

In some embodiments, the selectivity to alcohols in step (b) is at least about 45%, or at least about 50%, or at least about 55%, or at least about 60%, or at least about 65%, or at least about 70%, or at least about 75%, or at least about 80%.

In some embodiments, the selectivity to primary linear alcohols in step (b), based on total alcohols formed, is at least about 80%, or at least about 85%, or at least about 90%, or at least about 95%, or at least about 96%, or at least about 97%, or at least about 98%, or at least about 99%.

In some embodiments, the selectivity to primary branched alcohols in step (b), based on total alcohols formed, is less than about 20%, or less than about 15%, or less than about 10%, or less than about 5%, or less than about 4%, or less than about 3%, or less than about 2%, or less than about 1%.

In some embodiments, the effluent from step (b) further comprises one or more olefins.

The selectivity to olefins in step (b) may be less than about 20%, or less than about 15%, or less than about 10%, or less than about 5%.

In some embodiments, the effluent from step (b) further comprises one or more esters.

The selectivity to esters in step (b) may be less than about 30%, or less than about 25%, or less than about 20%, or less than about 15%, or less than about 10%, or less than about 5%.

In some embodiments, the effluent from step (b) further comprises one or more ethers.

The selectivity to ethers in step (b) may be less than about 20%, or less than about 15%, or less than about 10%, or less than about 5%.

In some embodiments, the effluent from step (b) further comprises one or more aldehydes and/or ketones.

The selectivity to aldehydes and ketones in step (b) may be less than about 20%, or less than about 15%, or less than about 10%, or less than about 5%. The selectivity to aldehydes and ketones may be between about 0.5% and about 25%, or between about 1% and about 20%.

In some embodiments, step (c) is performed at a temperature from about 100° C. to about 180° C.

In some embodiments, catalyst (E) is a solid acid catalyst comprising one or more of acidic resins, alumina and aluminosilicates, heteropoly acids, and tungsten and molybdenum functionalized oxides.

In some embodiments, the ethers produced in step (c) comprise one or more C8-C24 ethers.

In some embodiments, the olefins produced in step (c) comprise one or more C6-C14 olefins.

The process may further comprise:

(i) separating the effluent from step (b) into a first stream rich in olefins and one or more second streams rich in alcohols, wherein the one or more second streams rich in alcohols comprise a first stream rich in C2-C4 alcohols and a second stream rich in C4+ alcohols; and (ii) recycling at least a portion of the first stream rich in C2-C4 alcohols to step (b).

The process may further comprise:

(iii) contacting at least a portion of the second stream rich in C4+ alcohols with the catalyst (E) in reactor (E) under conditions effective to dehydrate at least a portion of the C4+ alcohols to ethers and olefins; and (iv) separating the ethers and olefins produced in step (iii) into a second stream rich in olefins, a stream rich in ethers, and a stream rich in alcohols.

The process may further comprise the step of combining at least a portion of the first stream rich in olefins produced in step (i) with at least a portion of the second stream rich in olefins produced in step (iv).

In some embodiments, the first stream rich in olefins produced in step (i) comprises C2-C4 olefins.

In some embodiments, the process further comprises the step of recycling at least a portion of the stream rich in alcohols produced in step (iv) to step (iii).

In some embodiments, the stream rich in ethers produced in step (iv) comprises one or more C8-C16+ ethers.

In some embodiments, the second stream rich in olefins produced in step (iv) comprises one or more C6+ olefins.

In further, optional steps, at least a portion of any one or more of the first stream rich in olefins, the second stream rich in olefins, and the combined streams of olefins, are oligomerized to higher olefins in the presence of a catalyst comprising acidic sites.

The catalyst comprising acid sites may further comprise a transition metal, for example cobalt or nickel.

In some embodiments, the higher olefins may comprise C8-C16+ olefins.

In some embodiments, at least a portion of the higher olefins may be hydrotreated in the presence of a transition metal catalyst to paraffins.

In some embodiments, the paraffins may comprise C8-C16+ paraffins.

Further features and advantages of the present disclosure will be understood by reference to the following drawings and detailed description.

DETAILED DESCRIPTION OF THE EMBODIMENTS

Figure 1:
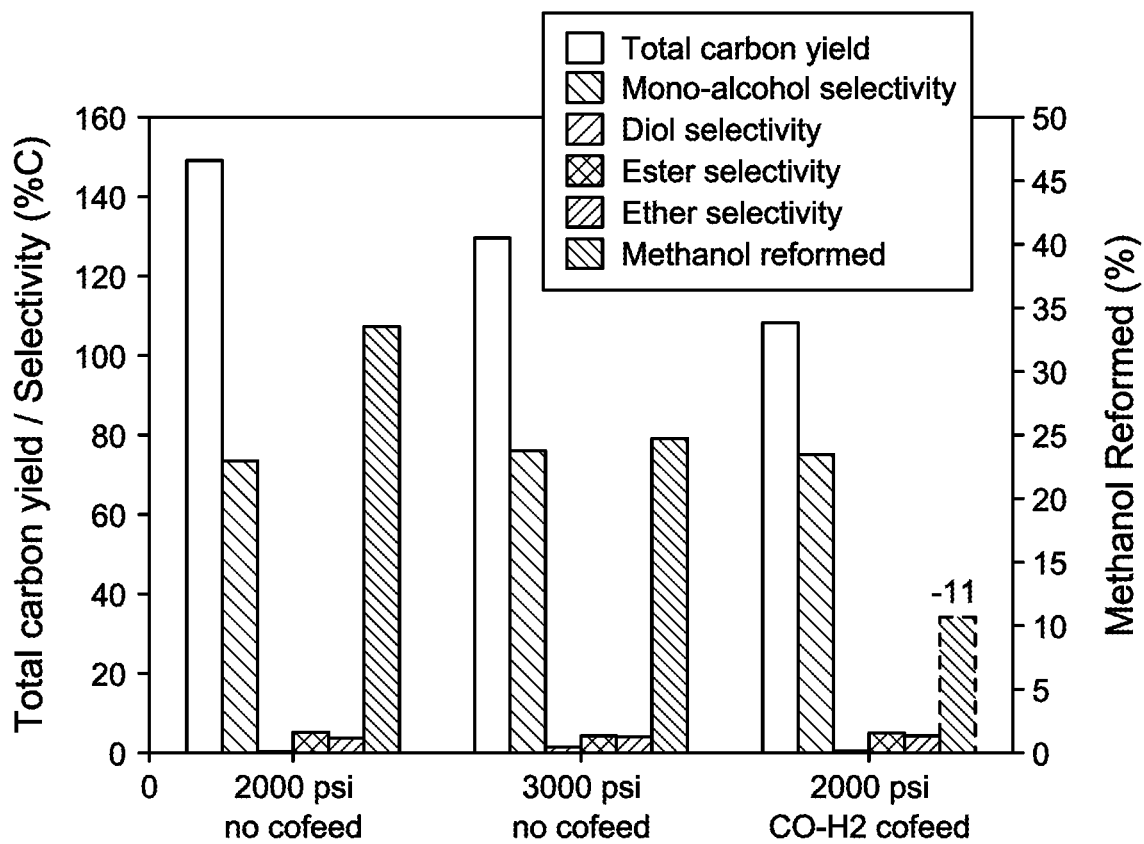
FIG. 1 is a bar chart illustrating carbon yield, product selectivity, and percentage methanol reformed at different pressures and with CO—$H_2$ addition.

The following is a detailed description of the disclosure provided to aid those skilled in the art in practicing the present disclosure. Those of ordinary skill in the art may make modifications and variations in the embodiments described herein without departing from the spirit or scope of the present disclosure.

Although any processes and materials similar or equivalent to those described herein can also be used in the practice or testing of the present disclosure, the preferred processes and materials are now described.

It must also be noted that, as used in the specification and the appended claims, the singular forms 'a', 'an' and 'the' include plural referents unless otherwise specified. Thus, for example, reference to 'alcohol' may include more than one alcohols, and the like.

Throughout this specification, use of the terms 'comprises' or 'comprising' or grammatical variations thereon shall be taken to specify the presence of stated features, integers, steps or components but does not preclude the presence or addition of one or more other features, integers, steps, components or groups thereof not specifically mentioned.

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as Hawley's Condensed Chemical Dictionary 14th Edition, by R. J. Lewis, John Wiley & Sons, New York, N.Y., 2001.

Unless specifically stated or obvious from context, as used herein, the term 'about' is understood as within a range of normal tolerance in the art, for example within two standard deviations of the mean. 'About' can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term 'about'.

Any processes provided herein can be combined with one or more of any of the other processes provided herein.

Ranges provided herein are understood to be shorthand for all the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein the term 'biomass' can include plant or animal matter such as one or more of manure, agricultural residues, energy crops, wood, wood wastes, food waste, municipal waste, paper waste, cardboard waste, cellulose, seed or vegetable oil, sugar cane bagasse, corn stover, straws, grasses and chitin.

Reference will now be made in detail to exemplary embodiments of the disclosure.

While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims.

Biomass to Alcohols

The present disclosure relates to processes for converting biomass to alcohols. Central to the processes is the use of supercritical methanol depolymerization and hydrodeoxygenation of biomass to produce a mixture of alcohols. The processes may operate continuously and may employ one or both recycle of reformed gases (CO and $H_2$) and recycle of light alcohols, including methanol, to improve higher alcohol yields. Further, employing a second reactor (reactor (C)) which operates at a lower temperature to the first reactor (reactor (A)) shifts the methanol reforming equilibrium to favour alcohol production.

In the present disclosure, reference to 'separation' of process streams may refer to one or more distillative separations, wherein components are separated based on boiling point.

Processes

Embodiments of the herein disclosed biomass to alcohol processes utilize either a single reactor for biomass depolymerization and hydrodeoxygenation or multiple reactor configurations, for example, a dual reactor configuration, wherein biomass depolymerization and hydrodeoxygenation is performed in a first reactor (reactor (A)) and methanol synthesis from CO and $H_2$ is performed in a second reactor (reactor (C)), thus limiting the loss of methanol through reforming.

Solubilization/Dispersion of Biomass

As biomass may be solid it is preferentially pretreated so as to aid in conveying to the reactor. The biomass may be pretreated in a number of ways.

The biomass may be fed to reactor (A) in one or more of methanol, higher alcohol and inert fluid.

In one embodiment the biomass may be pre-treated with methanol so as to disperse or solubilize the biomass prior to conversion to alcohols. The degree of solubilization will depend on the nature of the biomass, the concentration of biomass in the methanol and the temperature.

Additionally or alternately, the biomass may be pretreated with a suitable fluid so as to disperse or solubilize the biomass prior to conversion to alcohols. The degree of solubilization will depend on the nature of the biomass, the concentration of biomass in the fluid and the temperature. Suitable fluids comprise, but are not limited to, inert fluids such as pentane or other saturated hydrocarbons. In such an embodiment the methanol may be separately fed to the depolymerization and hydrodeoxygenation reactor (reactor (A)).

In other embodiments, other alcohols, such as ethanol, may be mixed with the biomass and the resulting mixture comprising biomass and ethanol fed to reactor (A). In this embodiment the methanol may be separately fed to reactor (A).

In other embodiments a mixture of biomass, methanol and one or more higher alcohols may be fed to reactor (A).

In some embodiments, the biomass is solubilized under conditions of elevated temperature, for example, temperatures greater than about 20° C. The process of solubilizing the biomass, at elevated temperatures, may partially depolymerize the biomass in the absence of catalyst. In the presence of catalyst the biomass is further depolymerized, but also undergoes hydrodeoxygenation and other reactions, for example, retro-aldol condensations, dehydrations, hydrogenations, and aldol reactions.

The amount of biomass in the methanol and/or inert fluid and/or higher alcohol in reactor (A) may be at least 5% by weight, or at least 10% by weight, or at least 15% by weight, or at least 20% by weight.

The percentage by weight of biomass fed to reactor (A) is, advantageously, as high as possible, without significantly negatively influencing the yield of product alcohols. A higher weight percent biomass results in lower methanol consumption which in turn reduces the amount of fossil derived carbon in the product alcohols, assuming the methanol utilized is fossil derived.

Single Reactor Process

In embodiments, a feed comprising biomass and methanol are fed into reactor (A) that contains catalyst (A). The biomass may be converted into a mixture of $C_2$-$C_6$ alcohols, ethers and esters, as well as $C_8$-$C_{10}$ cyclic alcohols, while methanol is reformed to a mixture of $H_2$, CO and $CO_2$. During the reaction methanol is also incorporated into the products through C—C coupling according to the reaction shown in Equation 1, while hydrogen is incorporated into the products according to the reaction shown in Equation 2.

$$C_xH_yO_z + CH_4O \rightarrow C_{x+1}H_{y+2}O_z + H_2O \qquad \text{Equation 1}$$

$$C_xH_yO_z + H_2 \rightarrow C_xH_yO_{z-1} + H_2O \qquad \text{Equation 2}$$

The effluent from reactor (A) is separated into one or more liquid streams and a gas stream. The gases are recycled back to reactor (A) and, in some embodiments, mixed with a make-up stream of gas comprising $H_2$, CO, and $CO_2$. The recycled gases and the make-up stream of synthesis gas maintain an equilibrium between methanol and reformed gases given by the reactions shown in Equation 3 and Equation 4 and replace methanol incorporated into the liquid products shown in Equation 1 by synthesizing methanol via methanol synthesis (reverse of the reaction shown in Equation 3).

$$CH_4O \leftrightarrow CO + 2H_2 \qquad \text{Equation 3}$$

$$CO + H_2O \leftrightarrow CO_2 + H_2 \qquad \text{Equation 4}$$

The synthesis gas make-up can be either hydrogen rich or carbon monoxide rich to remove oxygen from the system as either water (through Equation 2) or as carbon dioxide (through a combination of Equation 2 and Equation 4 shown as Equation 5) respectively.

$$C_xH_yO_z + CO \rightarrow C_xH_yO_{z-1} + CO_2 \qquad \text{Equation 5}$$

By recycling gases and adding a make-up stream, the only loss of methanol may be the amount incorporated into the products which may be replaced with synthesis gas rather than methanol.

In some embodiments, the supercritical methanol depolymerization and hydrodeoxygenation is performed in a single reactor, the reactor containing one or more beds of catalyst (A).

The temperature of reactor (A) bed may be from about 200° C. to about 500° C., preferably from about 250° C. to about 400° C., more preferably from about 280° C. to about 350° C., even more preferably from about 280° C. to about 320° C.

In some embodiments, the weight hour space velocity (WHSV) in reactor (A) may be from about 0.1 h-1 to about 10 h-1, or from about 0.2 h-1 to about 5 h-1, or from about 0.5 h-1 to about 5 h-1.

Reactions at High Pressure or CO—$H_2$ Co-Feed

Reactions with either higher pressure in reactor (A) or a 35%/65% CO—$H_2$ co-feed to the reactor (A) were performed to test the influence on methanol reforming. The CO—$H_2$ mixture composition was chosen to match the stoichiometric composition for methanol synthesis.

These reactions were performed with 10 wt. % glycerol in methanol. Glycerol was used as a model compound in place of biomass as it has been shown to undergo the same C—C coupling and C—C scission reactions as oxygenates produced from retro-aldol condensation of cellulose monomers (Galebach P. H, et al, *Investigation of the Reaction Pathways of Biomass Derived Oxygenate Conversion into Monoalcohols in Supercritical Methanol Depolymerization and Hydrodeoxygenation*, ACS Sustainable Chem. Eng., 2018, 6(3), 4330-4344)

Reactions were performed with 10 wt. % glycerol in methanol at 2000 psi (13.8 MPa) and 3000 psi (20.7 MPa) without a co-feed, and 2000 psi (13.8 MPa) with CO—$H_2$ co-feed. The liquid products and methanol reformed at each condition are shown in FIG. 1. Although the carbon yields are different between the three reaction conditions, the liquid phase product selectivity is very similar. In all three reactions, the primary products are mono-alcohols (74-76% selectivity) with some selectivity to esters and ethers (4-6% selectivity). The selectivity to diols is low (0-1% selectivity).

The methanol reformed from each reaction is also shown in FIG. 1. At 2000 psi (13.8 MPa) without a gas co-feed the methanol reformed is 35%. When the pressure of the reactor is increased to 3000 psi (20.7 MPa) the extent of methanol reforming decreases to 26%. The CO—$H_2$ co-feed was set to give an inlet composition of 71% gas and 29% liquid. The reaction at 2000 psi (13.8 MPa) with a CO—$H_2$ gas co-feed had a negative extent of methanol reforming of 11%. The negative methanol reforming indicates the co-feed of CO and $H_2$ synthesized methanol in the reactor. The co-feed experiment demonstrates that carrying out supercritical methanol depolymerisation and hydrodeoxygenation of glycerol while operating at methanol reforming equilibrium is possible and that the catalyst can act as a methanol synthesis catalyst.

Reactor A Catalyst ('Catalyst A')

Catalyst (A) may comprise one or more metals supported on one or more metal oxides. The one or more metals may comprise one or more of Cu, Pd, Pt, Ni and Ru.

The one or more metal oxides may comprise one or more of MgO, CaO, SrO, BaO and CeO.

The metal oxide may further comprise one or more of $Al_2O_3$, $SiO_2$, $ZrO_2$, and $TiO_2$.

In some preferred embodiments, catalyst (A) comprises one or more of Cu and Pd supported on a mixed metal oxide. Preferably, the mixed metal oxide comprises MgO and $Al_2O_3$.

In other preferred embodiments, catalyst (A) comprises Cu supported on a mixed metal oxide comprising MgO and $Al_2O_3$.

The copper may be present as Cu (0), Cu(I) or mixtures thereof. Typically, a majority of copper is present as Cu (0).

The weight percent of the one or more of Cu, Pd, Pt, Ni and Ru in catalyst (A) may be from about 0.1 wt. % to about 95 wt. % based on the total weight of catalyst (A). Thus, the upper limit on the range of the one or more of Cu, Pd, Pt, Ni and Ru metals in catalyst (A) may be 95 wt. %, 90 wt. %, 85 wt. %, 80 wt. %, 75 wt. %, 70 wt. %, 65 wt. %, 60 wt. %, 55 wt. %, 50 wt. %, 45 wt. %, 40 wt. %, 35 wt. %, 30 wt. %, 25 wt. %, 20 wt. %, 19 wt. %, 18 wt. %, 17 wt. %, 16 wt. %, 15 wt. %, 14 wt. %, 13 wt. %, 12 wt. %, 11 wt. %, 10.0 wt. %, 9.0 wt. %, 8.0 wt. %, 7.0 wt. %, 6.0 wt. %, or 5.0 wt. %; and the lower limit on the range may be 10 wt. %, 9.0 wt. %, 8.0 wt. %, 7.0 wt. %, 6.0 wt. %, 5.0 wt. %, 4.0 wt. %, 3.0 wt. %, 2.0 wt. %, 1.0 wt. %, or 0.1 wt. %.

In some embodiments, when the one or more metals comprise Cu or Ni the upper limit on the range may be 95 wt. %, 90 wt. %, 85 wt. %, 80 wt. %, 75 wt. %, 70 wt. %, 65 wt. %, 60 wt. %, 55 wt. %, 50 wt. %, 45 wt. %, 40 wt. %, 35 wt. %, or 30 wt. % and the lower limit on the range may be 10 wt. %, 9.0 wt. %, 8.0 wt. %, 7.0 wt. %, 6.0 wt. %, or 5.0 wt. %.

In some embodiments, when the one or more metals comprise Pt, Pd or Ru the upper limit on the range may be 25 wt. %, 20 wt. %, 19 wt. %, 18 wt. %, 17 wt. %, 16 wt. %, 15 wt. %, 14 wt. %, 13 wt. %, 12 wt. %, 11 wt. %, 10.0 wt. %, 9.0 wt. %, 8.0 wt. %, 7.0 wt. %, 6.0 wt. %, or 5.0 wt. %; and the lower limit on the range may be 4.0 wt. %, 3.0 wt. %, 2.0 wt. %, 1.0 wt. %, or 0.1 wt. %.

Ranges expressly disclosed include combinations of any of the above-enumerated upper and lower limits.

Generally, catalyst (A) having the desired activity can have a molar ratio of one or more of magnesium, calcium, strontium, barium and cerium to one or more of aluminium, silicon, zirconium and titanium of about 10 to about 1, for example about 5 to about 1, about 4 to about 1, or about 3 to about 1. In some embodiments, the molar ratio of one or more of magnesium, calcium, strontium, barium and cerium to one or more of aluminium, silicon, zirconium and titanium can be at least about 10, for example at least about 5, at least about 4, or at least about 3.

Additionally, or alternately, the molar ratio of one or more of magnesium, calcium, strontium, barium and cerium to one or more of aluminium, silicon, zirconium and titanium can be about 10 or less, for example about 5 or less, about 4 or less, or about 3 or less.

In some preferred embodiments, the molar ratio of one or more of magnesium, calcium, strontium, barium and cerium to one or more of aluminium, silicon, zirconium and titanium can be at least about 5, for example at least about 4 or at least about 3. In such embodiments, the molar ratio of one or more of magnesium, calcium, strontium, barium and cerium to one or more of aluminium, silicon, zirconium and titanium can optionally be about 5 or less, for example about 4 or less, or about 3 or less.

In some preferred embodiments, wherein catalyst (A) comprises Cu supported on, for example, a mixed metal oxide comprising MgO and $Al_2O_3$, the amount of Cu in the catalyst is between 5 wt. % and 30 wt. %, or between 10 wt. % and 20 wt. %, based on the total weight of the catalyst.

Preferably, catalyst (A) is reduced prior to use. Catalyst (A) may be reduced through treatment with hydrogen at elevated temperature. Typical temperatures may be between about 80° C. and about 450° C., or about 150° C. and about 450° C., or about 250° C. and about 450° C., or between about 300° C. and about 400° C.

Biomass Loading

Figure 2:
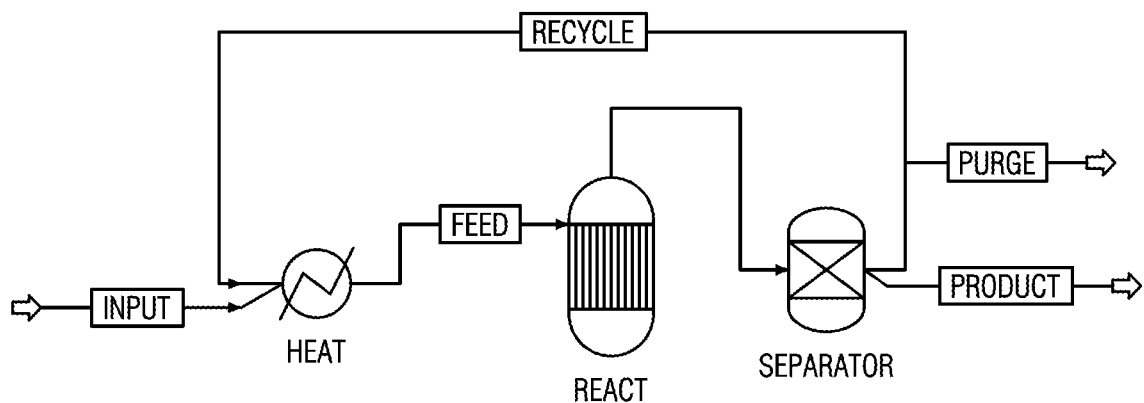
FIG. 2 is a process flow diagram used to simulate the effect of biomass loading on greenhouse gas emissions contributed by methanol consumption.

Process simulations were performed in Aspen Plus (Aspen Technology, Inc.) based on the process flow chart shown in FIG. 2. The simulations examined the effect of biomass loading in methanol under single reactor operation with methanol and gas (CO, $H_2$ and $CO_2$) recycle.

Figure 3:
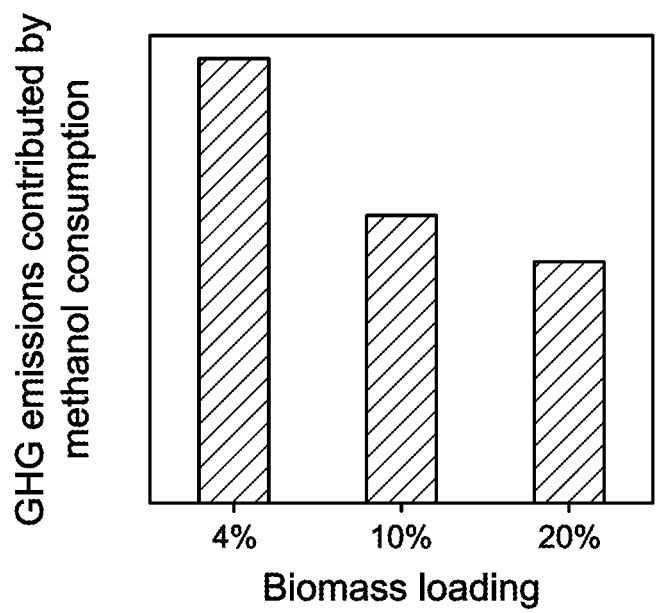
FIG. 3 is a bar chart illustrating the effect of biomass loading on greenhouse gas emissions contributed by methanol consumption.

Biomass loadings in methanol of 4, 10 and 20 wt. % were examined and the simulations revealed that increasing the loading from 4 to 20 wt. % resulted in a significant decrease in greenhouse gas emissions. FIG. 3 illustrates the results of the simulations and indicates that emissions were up to 50% less when the biomass loading was 20 wt. %, compared to 4 wt. %.

During the supercritical methanol depolymerization and hydrodeoxygenation process, methanol carbon is incorporated into the alcohol products. Since the methanol is primarily derived from fossil fuels, it is not renewable. An increase in biomass loading in the reactor reduces the methanol carbon incorporation into the produced alcohols, thus reducing the net requirement for fresh methanol addition.

Additionally, methanol recycle loops are significantly smaller at 20 wt. % biomass loading, which reduces both capital costs and energy consumption during operation.

Furthermore, increasing biomass loading reduces feed volumetric flowrate which in turn reduces the size of the reactor and, therefore, reactor capital cost. Reactor capital cost can be approximated as being equal to reference cost* (reactor volume/reference volume)$^X$, where X may be, in some embodiments, about 0.6. In such a scenario, reactor capital cost would change with feed volumetric flowrate with a 0.6 power.

Accordingly, increasing biomass loading improves the overall economics of the process.

Methanol Synthesis in a Two-Stage Reactor

In some embodiments, a second reactor (reactor C) is employed, the second reactor containing, for example, one or more beds of catalyst (C). Preferably, the temperature of reactor (C) bed is lower than the temperature of reactor (A) bed. This is advantageous as the lower temperature in reactor (C) bed will shift the methanol reforming equilibrium toward methanol, with the result that overall alcohol yield is improved.

Under two-stage reactor operation, the temperature of reactor (A) bed may be from about 200° C. to about 500° C., or from about 250° C. to about 400° C., or from about 280° C. to about 350° C., or from about 280° C. to about 320° C., and the temperature of reactor (C) bed may be from about 200° C. to about 350° C., or from about 230° C. to about 320° C., or from about 240° C. to about 300° C., or from about 240° C. to about 280° C.

Figure 4:
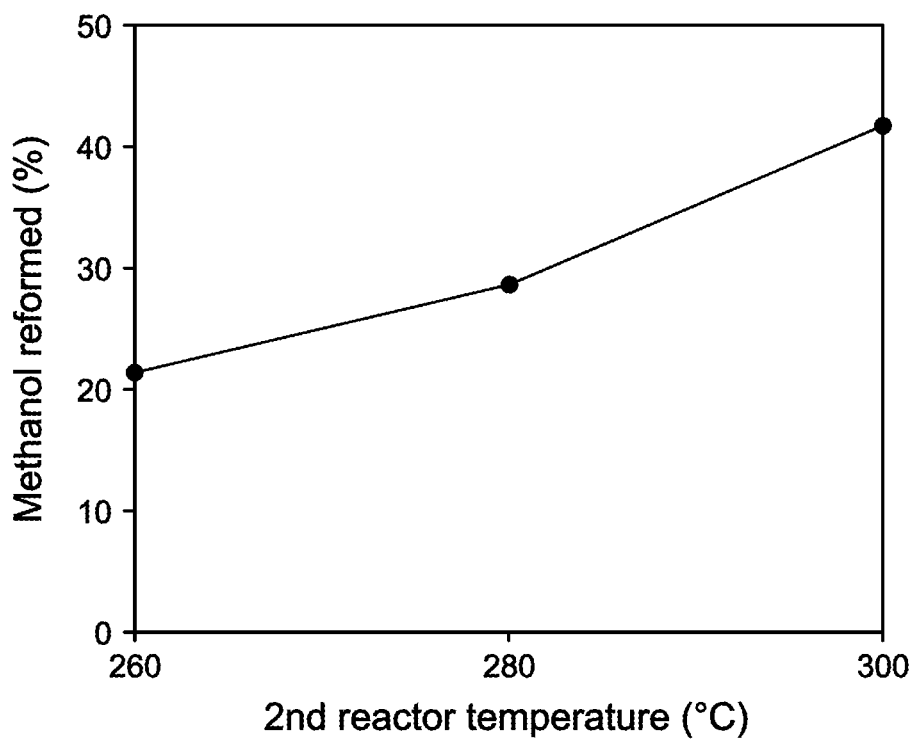
FIG. 4 is a graph illustrating the percentage reformed methanol at 260° C., 280° C. and 300° C.

Experimental studies employing a two-stage reactor configuration in which the reactor (A) bed was at a temperature of about 300° C. and reactor (C) bed was at a temperature of either about 300° C. or about 260° C. revealed that the 260° C. reactor (C) bed temperature significantly reduced the % methanol reformed from 42% to 22% without affecting either the yield or selectivity to higher alcohols. FIG. 4 illustrates the % methanol reformed in the second reactor (reactor (C)) and indicates that, advantageously, significantly less methanol was reformed when the second reactor (V) operated at 260° C. (22% reformed) relative to 300° C. (42% reformed).

Figure 5:
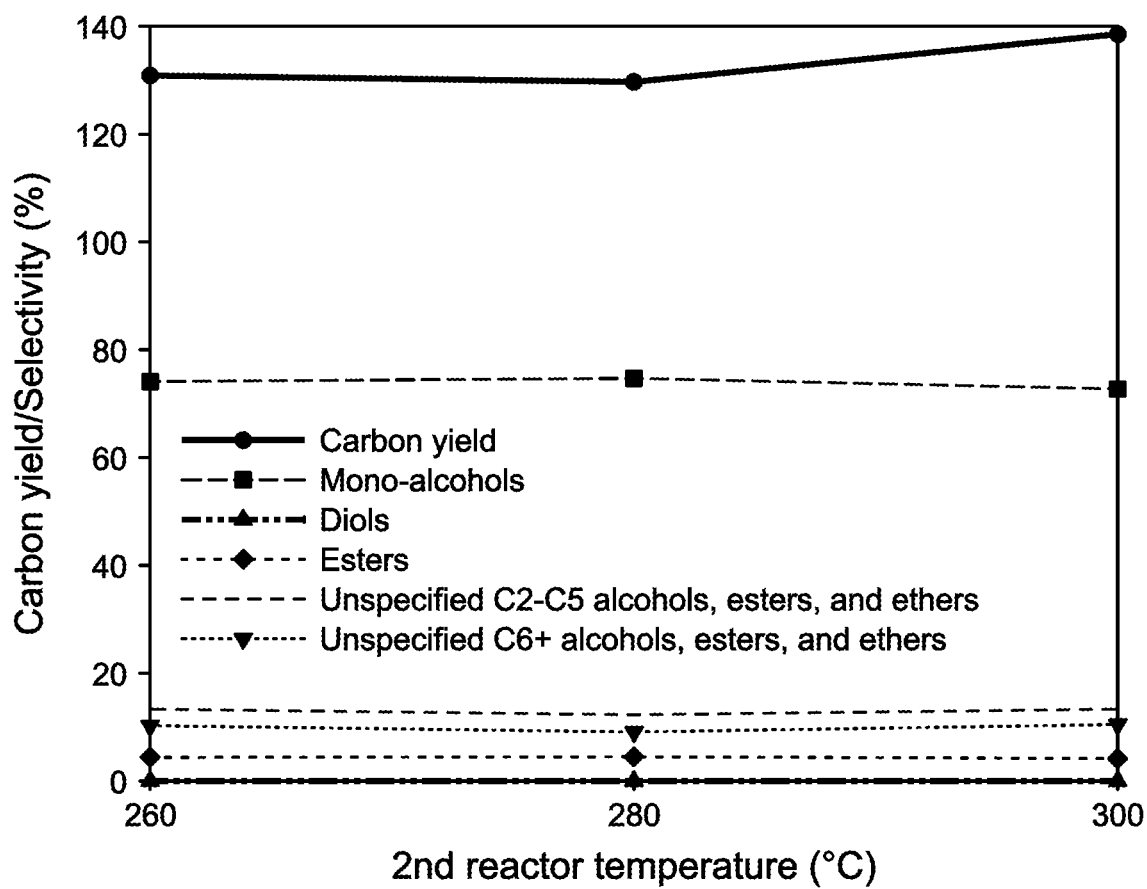
FIG. 5 is a graph illustrating percentage carbon yield and product selectivity at 260° C., 280° C. and 300° C.

FIG. 5 illustrates the carbon yield and product selectivity of supercritical methanol depolymerization and hydrodeoxygenation of glycerol at 300° C. in a first reactor (reactor (A)) and methanol synthesis in a second reactor (reactor (C)) at 260-300° C. It is evident that the temperature in the second reactor had minimal effect on carbon yield and product selectivity.

In some embodiments, the weight hour space velocity (WHSV) in the first reactor (A) is from about 0.1 to about 10 $h^{-1}$, or from about 0.2 $h^{-1}$ to about 5 or from about 0.5 to about 5 $h^{-1}$.

In some embodiments, the weight hour space velocity (WHSV) in the second reactor (C) is from about 0.1 $h^{-1}$ to about 10 $h^{-1}$, or from about 0.2 $h^{-1}$ to about 5 $h^{-1}$, or from about 0.5 $h^{-1}$ to about 5 $h^{-1}$.

Reactor C Catalyst ('Catalyst C')

Catalyst (C) may comprise one or more metals supported on one or more metal oxides. The one or more metals may comprise one or more of Cu, Pd, Pt, Ni and Ru.

The one or more metal oxides may comprise one or more of MgO, CaO, ZnO, SrO, BaO and CeO.

The metal oxide may further comprise one or more of $Al_2O_3$, $SiO_2$, $ZrO_2$, and $TiO_2$.

In some preferred embodiments, catalyst (C) is a methanol synthesis catalyst comprising Cu supported on a metal oxide. Preferably, the metal oxide comprises one or more of ZnO, MgO, $Al_2O_3$ and $SiO_2$.

The weight percent of the one or more of Cu, Pd, Pt, Ni and Ru in catalyst (C) may be from about 0.1 wt. % to about 95 wt. % based on the total weight of catalyst (C). Thus, the upper limit on the range of the one or more of Cu, Pd, Pt, Ni and Ru metals in catalyst (C) may be 95 wt. %, 90 wt. %, 85 wt. %, 80 wt. %, 75 wt. %, 70 wt. %, 65 wt. %, 60 wt. %, 55 wt. %, 50 wt. %, 45 wt. %, 40 wt. %, 35 wt. %, 30 wt. %, 25 wt. %, 20 wt. %, 19 wt. %, 18 wt. %, 17 wt. %, 16 wt. %, 15 wt. %, 14 wt. %, 13 wt. %, 12 wt. %, 11 wt. %, 10.0 wt. %, 9.0 wt. %, 8.0 wt. %, 7.0 wt. %, 6.0 wt. %, or 5.0 wt. %; and the lower limit on the range may be 10 wt. %, 9.0 wt. %, 8.0 wt. %, 7.0 wt. %, 6.0 wt. %, 5.0 wt. %, 4.0 wt. %, 3.0 wt. %, 2.0 wt. %, 1.0 wt. %, or 0.1 wt. %.

In some embodiments, when the one or more metals comprise Cu or Ni the upper limit on the range may be 95 wt. %, 90 wt. %, 85 wt. %, 80 wt. %, 75 wt. %, 70 wt. %, 65 wt. %, 60 wt. %, 55 wt. %, 50 wt. %, 45 wt. %, 40 wt. %, 35 wt. %, or 30 wt. % and the lower limit on the range may be 10 wt. %, 9.0 wt. %, 8.0 wt. %, 7.0 wt. %, 6.0 wt. %, or 5.0 wt. %.

In some embodiments, when the one or more metals comprise Pt, Pd or Ru the upper limit on the range may be 25 wt. %, 20 wt. %, 19 wt. %, 18 wt. %, 17 wt. %, 16 wt. %, 15 wt. %, 14 wt. %, 13 wt. %, 12 wt. %, 11 wt. %, 10.0 wt. %, 9.0 wt. %, 8.0 wt. %, 7.0 wt. %, 6.0 wt. %, or 5.0 wt. %; and the lower limit on the range may be 4.0 wt. %, 3.0 wt. %, 2.0 wt. %, 1.0 wt. %, or 0.1 wt. %.

Ranges expressly disclosed include combinations of any of the above-enumerated upper and lower limits.

Generally, catalyst (C) having the desired activity can have a molar ratio of one or more of zinc, magnesium, calcium, strontium, barium and cerium to one or more of aluminium, silicon, zirconium and titanium of about 10 to about 1, for example about 5 to about 1, about 4 to about 1, or about 3 to about 1. In some embodiments, the molar ratio of one or more of zinc, magnesium, calcium, strontium, barium and cerium to one or more of aluminium, silicon, zirconium and titanium can be at least about 10, for example at least about 5, at least about 4, or at least about 3. Additionally, or alternately, the molar ratio of one or more of zinc, magnesium, calcium, strontium, barium and cerium to one or more of aluminium, silicon, zirconium and titanium can be about 10 or less, for example about 5 or less, about 4 or less, or about 3 or less.

In some preferred embodiments, the molar ratio of one or more of zinc, magnesium, calcium, strontium, barium and cerium to one or more of aluminium, silicon, zirconium and titanium can be at least about 5, for example at least about 4 or at least about 3. In such embodiments, the molar ratio of one or more of zinc, magnesium, calcium, strontium, barium and cerium to one or more of aluminium, silicon, zirconium and titanium can optionally be about 5 or less, for example about 4 or less, or about 3 or less.

In some preferred embodiments, wherein catalyst (C) comprises Cu supported on a metal oxide, for example, comprising ZnO and $Al_2O_3$, the amount of Cu in the catalyst is between 5 wt. % and 30 wt. %, or between 10 wt. % and 20 wt. %, based on the total weight of the catalyst. The amount of Zn in the catalyst is between 2 wt. % and 15 wt. %, or between 5 wt. % and 10 wt. %.

Preferably, catalyst (C) is reduced prior to use. Catalyst (C) may be reduced through treatment with hydrogen at elevated temperature. Typical temperatures may be between about 80° C. and about 450° C., or about 150° C. and about 450° C., or about 250° C. and about 450° C., or between about 300° C. and about 400° C.

In some embodiments of the herein disclosed processes catalyst (B) may be any one of the options disclosed in relation to catalyst (C) and may be the same or different to catalyst (C).

Catalyst Form

Catalysts as described herein can employ the catalyst in a powder form, prepared, for example by co-precipitation techniques or incipient wetness impregnation. Alternately, or additionally, the powder can be formulated into catalyst particles, such as by extrusion. Such catalyst particles, or extrudates, may be bound using one or more binders typically employed in the art.

Reactor Types

Various types of reactors may provide a suitable configuration for performing a supercritical methanol depolymerisation and hydrodeoxygenation of biomass. Suitable reactors may include fixed bed reactors, moving bed reactors, and slurry bed reactors.

It is noted that the activity and/or selectivity of a catalyst for supercritical methanol depolymerisation and hydrodeoxygenation of biomass may vary as the catalyst is exposed to increasing amounts of biomass feed.

In embodiments where a catalyst can be removed from the reactor for regeneration and recycle during operation of the reactor, such as a moving bed reactor, catalyst can be removed and replaced with regenerated catalyst.

In embodiments where fixed bed reactors are utilized, the reactors may comprise one or more beds of catalyst powder, particles or extrudates. Each bed may comprise the same catalyst, or, alternately, beds may comprise different catalysts. Where different catalysts are utilized, they may vary in terms of one or more of metal loading, metal type and metal oxide type.

For example, in one embodiment, a given reactor may contain more than one catalyst bed, each of which contain the same CuMgAl oxide catalyst. In another embodiment, a given reactor may contain more than one catalyst bed, wherein at least one bed has a different catalyst than another bed. For example one bed may contain a CuMgAl oxide having a particular Cu loading and another bed may contain a CuMgAl oxide catalyst having a different Cu loading. In another embodiment, one bed may contain a CuMgAl oxide catalyst and another bed may contain a CuZnAl oxide catalyst.

Other reactor types may also employ mixtures of different catalysts.

In the present disclosure, the total carbon yield (% C) is defined as in Equation (6).

$$\text{Total carbon yield } (\% \; C) = \frac{\text{mol } C_{products}}{\text{mol } C_{reactants}} \quad \text{Equation 6}$$

The total carbon yield is based on the sum of moles of carbon in the products and the moles of carbon in the reactants (biomass). Due to methanol incorporation in the liquid products the carbon yield can be above 100%.

In some embodiments of the present disclosure, the total carbon yield is at least about 50%, or at least about 55%, or at least about 60%, or at least about 65%, or at least about 70%, or at least about 75%, or at least about 80%, or at least about 85%, or at least about 90%, or at least about 95%.

The selectivity to mono-alcohols (% C) is defined in Equation 7.

$$\text{Monoalcohol selectivity } (\% \; C) = \frac{\text{mol } C_{monoalcohol}}{\text{mol } C_{total\;products}} \quad \text{Equation 7}$$

In some embodiments of the present disclosure, the selectivity to mono-alcohols is at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%.

In other embodiments of the present disclosure, the selectivity to mono-alcohols is between about 25% and about 90%, or between about 30% and about 90%, or between about 25% and about 80%, or between about 25% and about 70%.

The methanol reformed is defined by Equation 8.

$$\text{Methanol reformed} = \frac{mol_{CO} + mol_{CO_2} + mol_{CH_4}}{mol_{methanol} \text{ in feed}} \quad \text{Equation 8}$$

In some embodiments of the present disclosure, the methanol reformed is less than about 50%, or less than about 45%, or less than about 40%, or less than about 35%, or less than about 30%, or less than about 25%.

Biomass to Alcohol Process Embodiments

Figure 6:
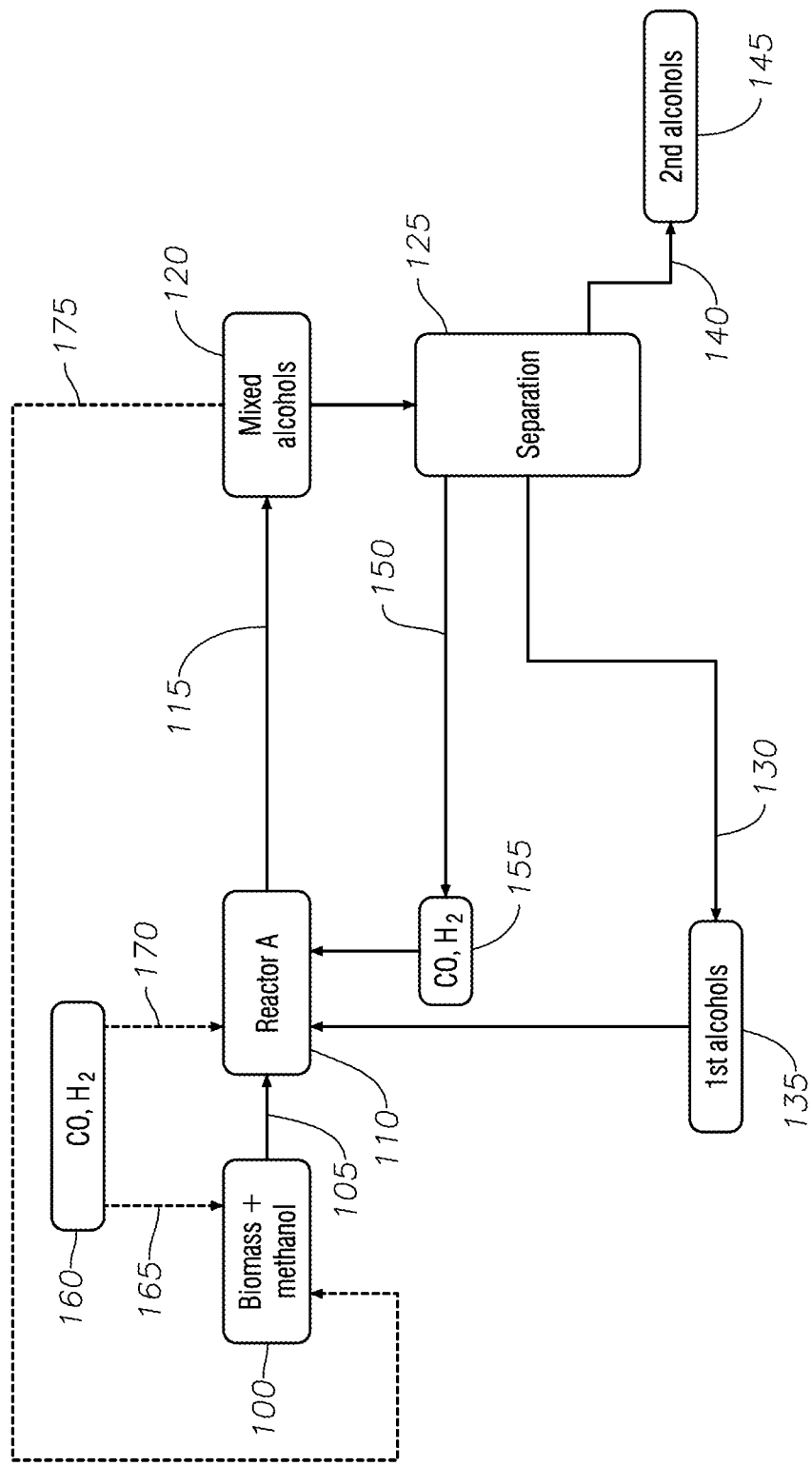
FIG. 6 is a flow diagram of a process for producing alcohols from biomass according to one embodiment of the present disclosure.

Referring first to FIG. 6, the process flow diagram illustrates the production of mixed alcohols from biomass and methanol according to one embodiment of the present disclosure.

In a first step a mixture of biomass and methanol (100) is fed via stream (105) to first reactor (110).

In some embodiments, and as illustrated, the biomass and methanol may be first contacted and fed to the first reactor as a mixture.

In other embodiments, the biomass may be first mixed (not illustrated) with a suitable alternate fluid to methanol. The fluid may solubilize, partially solubilize or disperse the biomass to facilitate feeding to the first reactor (110). In such embodiments, the methanol is separately fed to the first reactor.

In some embodiments, the biomass is solubilized under conditions of elevated temperature, for example, temperatures greater than about 20° C. The process of solubilizing the biomass, at elevated temperatures, may partially depolymerize the biomass in the absence of catalyst. In the presence of catalyst the biomass is further depolymerized, but also undergoes hydrodeoxygenation and other reactions, for example, retro-aldol condensations, dehydrations, hydrogenations, and aldol reactions.

In the first reactor (reactor A), which preferably comprises one or more beds of a CuMgAl oxide catalyst, the biomass is depolymerized. The effluent from reactor (A) which comprises a mixture of alcohols (120) is withdrawn via stream (115) and separated in one or more distillation units (125) into two alcohol rich streams (130) and (140) and a gas stream (150). Stream (130) ($1^{st}$ alcohols (135)) comprises lower boiling alcohols, including methanol, and is recycled to reactor (110). Stream (140) ($2^{nd}$ alcohols (145)) comprises higher boiling alcohols and may be utilized for other purposes, such as upgrading.

The gas stream (150) comprising carbon monoxide and hydrogen (155) is recycled to the reactor A (110).

Although FIG. 6 illustrates the recycled light alcohols, stream (130), and recycled gases, stream (150), being fed to reactor A, in other embodiments at least a portion of one or both of streams (130) and (150) may be fed to the biomass/methanol (100) and fed to reactor A with the biomass/methanol.

In optional steps, make-up syngas (160) may be fed to one or both the reactor A (110) or the biomass/methanol (100) via streams (170) and (165) respectively.

In an optional embodiment of the process, a portion of the effluent from reactor A comprising mixed alcohols may be recycled via stream (175) to the biomass/methanol (100) or to the reactor A (110) (not shown). Prior to this recycling, the effluent from reactor A may be subjected to a separation step wherein gases such as CO and $H_2$ are removed (not shown).

Figure 7:
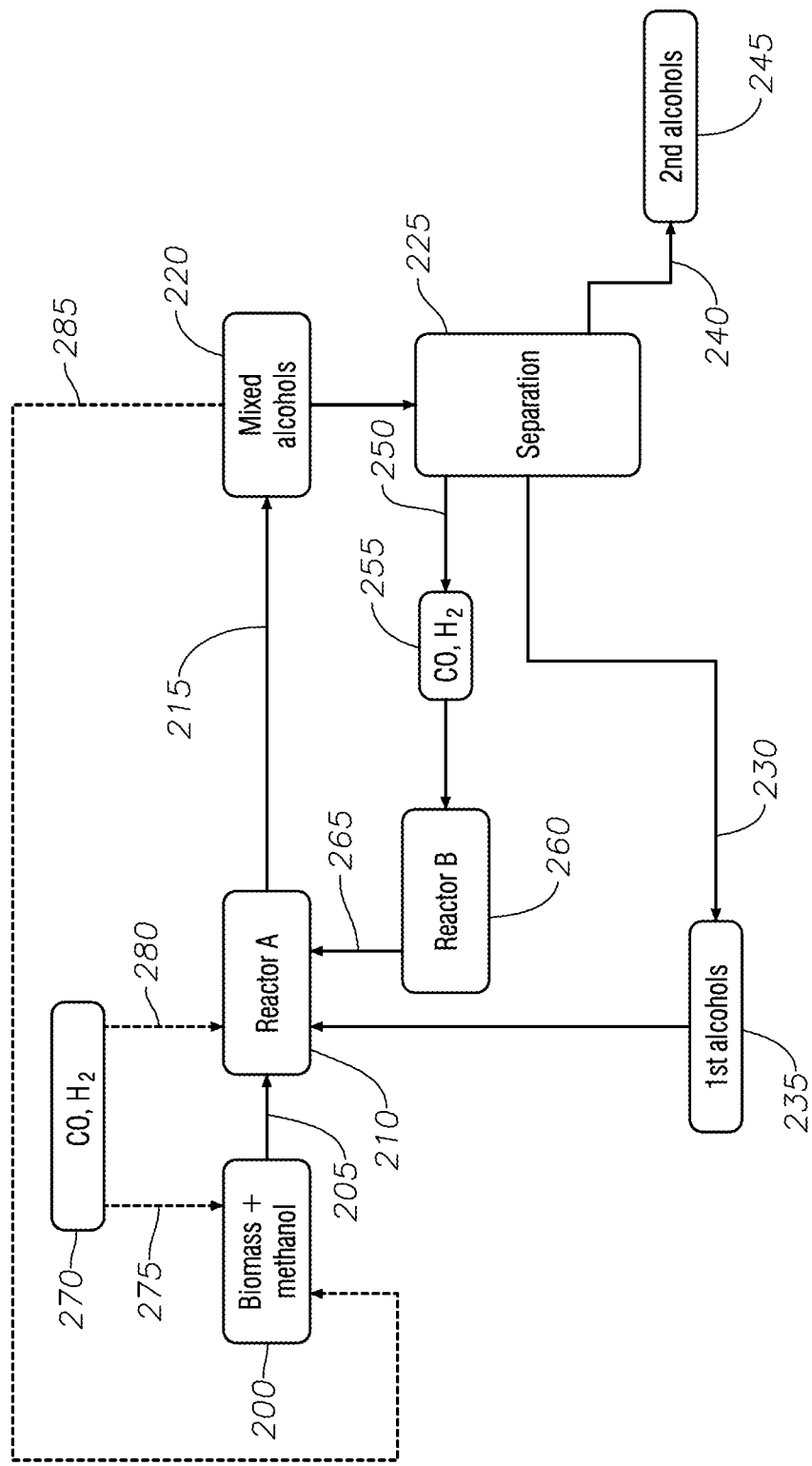
FIG. 7 is a flow diagram of a process for producing alcohols from biomass according to another embodiment of the present disclosure.

Referring to FIG. 7, the process flow diagram illustrates the production of mixed alcohols from biomass and methanol according to another embodiment of the present disclosure.

In a first step a mixture of biomass and methanol (200) is fed via stream (205) to first reactor A (210).

In some embodiments, and as illustrated, the biomass and methanol may be first contacted and fed to reactor A as a mixture.

In other embodiments, the biomass may be first mixed (not illustrated) with a suitable alternate fluid to methanol. The fluid may solubilize, partially solubilize or disperse the biomass to facilitate feeding to reactor A (210). In such embodiments, the methanol may be separately fed to the reactor A.

In some embodiments, the biomass is solubilized under conditions of elevated temperature, for example, temperatures greater than about 20° C. The process of solubilizing the biomass, at elevated temperatures, may partially depolymerize the biomass in the absence of catalyst. In the presence of catalyst the biomass is further depolymerized, but also undergoes hydrodeoxygenation and other reactions, for example, retro-aldol condensations, dehydrations, hydrogenations, and aldol reactions.

In reactor A, which preferably comprises one or more beds of a CuMgAl oxide catalyst, the biomass is depolymerized. The effluent from reactor A which comprises a mixture of alcohols (220) is withdrawn via stream (215) and separated in one or more distillation units (225) into two alcohol rich streams (230) and (240) and a gas stream (250). Stream (230) ($1^{st}$ alcohols (235)) comprises lower boiling alcohols, including methanol, and is recycled to reactor A (210).

Stream (240) ($2^{nd}$ alcohols (245)) comprises higher boiling alcohols and may be utilized for other purposes, such as upgrading.

The gas stream comprising CO and $H_2$ is fed via stream (250) to a reactor B (260) containing a catalyst which converts the CO and $H_2$ to methanol. The methanol is fed via stream (265) to reactor A.

Although FIG. 7 illustrates the recycled light alcohols, stream (230) being fed to the reactor A, in other embodiments at least a portion of stream (230) may be fed to the biomass/methanol (200) and fed to reactor A with the biomass/methanol.

Similarly, in some embodiments, at least a portion of methanol stream (265) may be fed to the biomass/methanol (200) and fed to reactor A with the biomass/methanol.

In optional steps, make-up syngas (270) may be fed to one or both reactor A (210) or the biomass/methanol (200) via streams (280) and (275) respectively.

In an optional embodiment of the process, a portion of the effluent from reactor A comprising mixed alcohols may be recycled via stream (285) to the biomass/methanol (200) or to reactor A (210) (not shown). Prior to recycling, the effluent from reactor A may be subjected to a separation step wherein gases such as CO and $H_2$ are removed (not shown).

Figure 8:
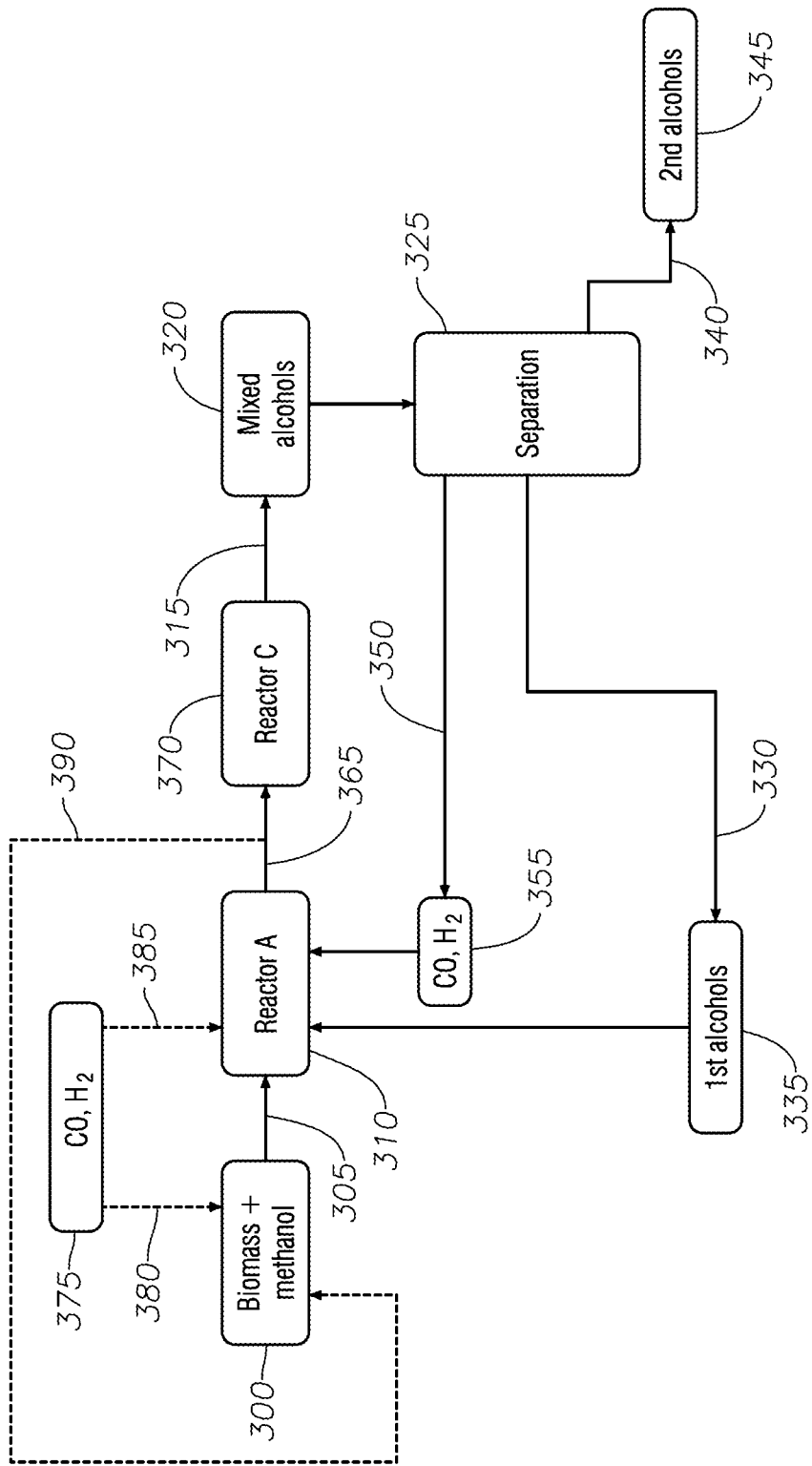
FIG. 8 is a flow diagram of a process for preparing alcohols from biomass according to another embodiment of the present disclosure utilizing two reactors and gas recycle to the first reactor.

Referring to FIG. 8, the process flow diagram illustrates the production of mixed alcohols from biomass and methanol according to another embodiment of the present disclosure, in which two reactors are employed.

In a first step a mixture of biomass and methanol (300) is fed via stream (305) to reactor A (310).

In some embodiments, and as illustrated, the biomass and methanol may be first contacted and fed to reactor A as a mixture.

In other embodiments, the biomass may be first mixed (not illustrated) with a suitable alternate fluid to methanol. The fluid may solubilize, partially solubilize or disperse the biomass to facilitate feeding to reactor A (310). In such embodiments, the methanol is separately fed to the reactor A.

In some embodiments, the biomass is solubilized under conditions of elevated temperature, for example, temperatures greater than about 20° C. The process of solubilizing the biomass, at elevated temperatures, may partially depolymerize the biomass in the absence of catalyst. In the presence of catalyst the biomass is further depolymerized, but also undergoes hydrodeoxygenation and other reactions, for example, retro-aldol condensations, dehydrations, hydrogenations, and aldol reactions.

In reactor A, which preferably comprises one or more beds of a CuMgAl oxide catalyst, the biomass is depolymerized. The effluent from reactor A is withdrawn via stream (365) and fed to second reactor B (370). The reactor B (370), which may comprise one or more beds of a CuMgAl oxide catalyst, or preferably a methanol synthesis catalyst, for example a CuZnAl oxide catalyst, is preferably operated at a lower temperature to reactor A. This facilitates the conversion of CO and $H_2$ formed in reactor A to methanol.

The effluent from reactor B, which comprises a mixture of alcohols (320), is withdrawn via stream (315) and separated in one or more distillation units (325) into two alcohol rich streams (330) and (340) and a gas stream (350). Stream (330) (1$^{st}$ alcohols (335)) comprises lower boiling alcohols, including methanol, and is recycled to reactor A (310). Stream (340) (2$^{nd}$ alcohols (345)) comprises higher boiling alcohols and may be utilized for other purposes, such as upgrading.

The gas stream (350) comprising carbon monoxide and hydrogen (355) is recycled to reactor A (310).

Although FIG. 8 illustrates the recycled light alcohols, stream (330), and recycled gases, stream (350), being fed reactor A, in other embodiments at least a portion of one or both of streams (330) and (350) may be fed to the biomass/methanol (300) and fed to reactor A with the biomass/methanol.

In optional steps, make-up syngas (375) may be fed to one or both reactor A (310) or the biomass/methanol (300) via streams (385) and (380) respectively.

In an optional embodiment of the process, a portion of the effluent from reactor A comprising mixed alcohols may be recycled via stream (390) to the biomass/methanol (300) or to reactor A (310) (not shown). Prior to this recycling, the effluent from reactor A may be subjected to a separation step wherein gases such as CO and H$_2$ are removed (not shown).

Figure 9:
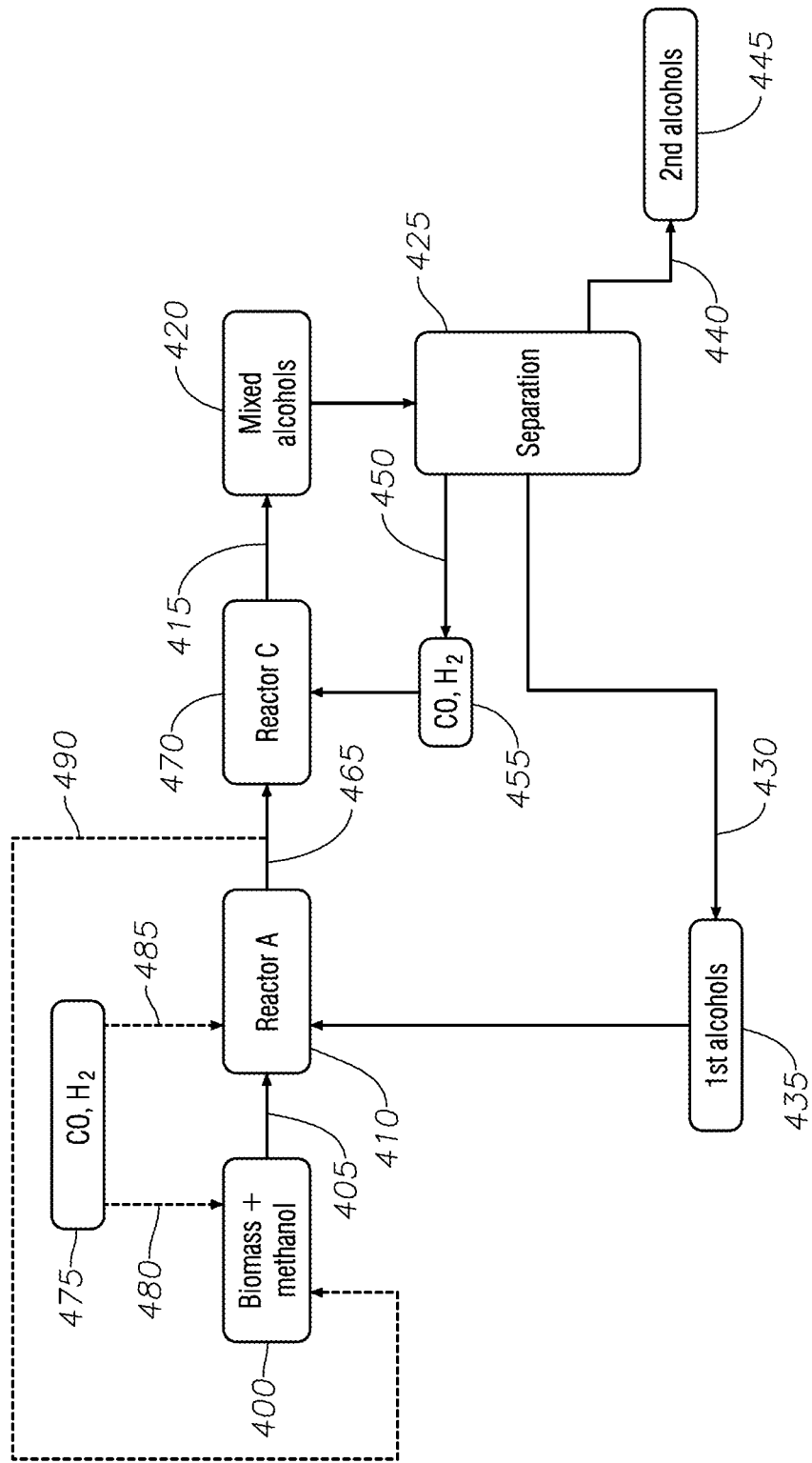
FIG. 9 is a flow diagram of a process for preparing alcohols from biomass according to another embodiment of the present disclosure utilizing two reactors and gas recycle to the second reactor.

Referring to FIG. 9, the process flow diagram illustrates the production of mixed alcohols from biomass and methanol according to another embodiment of the present disclosure. The process illustrated in FIG. 9 is identical to that of FIG. 8, except that the gas recycle stream (450) is recycled to reactor B (470) which advantageously converts the CO and H$_2$ to methanol.

In other embodiments, the gas stream comprising CO and H$_2$ may be recycled to one or both the reactors A and B.

In an optional embodiment of the process, a portion of the effluent from reactor A comprising mixed alcohols may be recycled via stream (490) to the biomass/methanol (400) or to the reactor A (410) (not shown). Prior to this recycling, the effluent from reactor A may be subjected to a separation step wherein gases such as CO and H$_2$ are removed (not shown).

Figure 10:
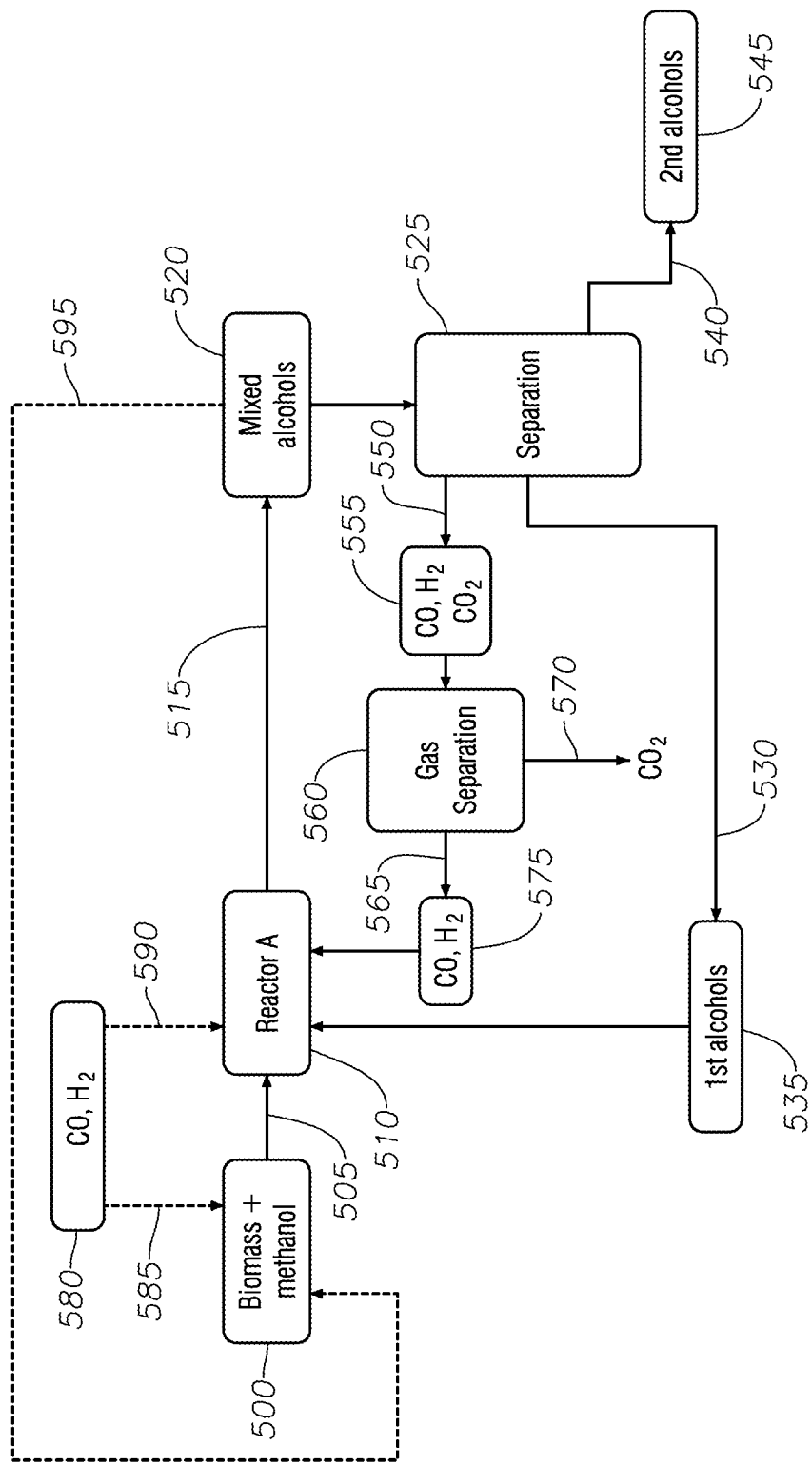
FIG. 10 is a flow diagram of a process for preparing alcohols from biomass according to another embodiment of the present disclosure, illustrating removal of $CO_2$ from the CO/$H_2$ recycle stream.

FIG. 10 illustrates a further process option according to the present disclosure. wherein the recycled gas stream (550) comprising carbon monoxide and hydrogen may also contain carbon dioxide which is reduced in concentration in separator (560) to provide carbon dioxide stream (570) and carbon monoxide/hydrogen stream (565) which is then fed to reactor A. It will be appreciated that the CO$_2$ separation step may also be present in any one or more of the herein disclosed processes, wherein the gases are recycled to one or both reactor A and reactor B.

In an optional embodiment of the process, a portion of the effluent from reactor A comprising mixed alcohols may be recycled via stream (595) to the biomass/methanol (500) or to the reactor A (510) (not shown). Prior to this recycling, the effluent from reactor A may be subjected to a separation step wherein gases such as CO and H$_2$ are removed (not shown).

Figure 11:
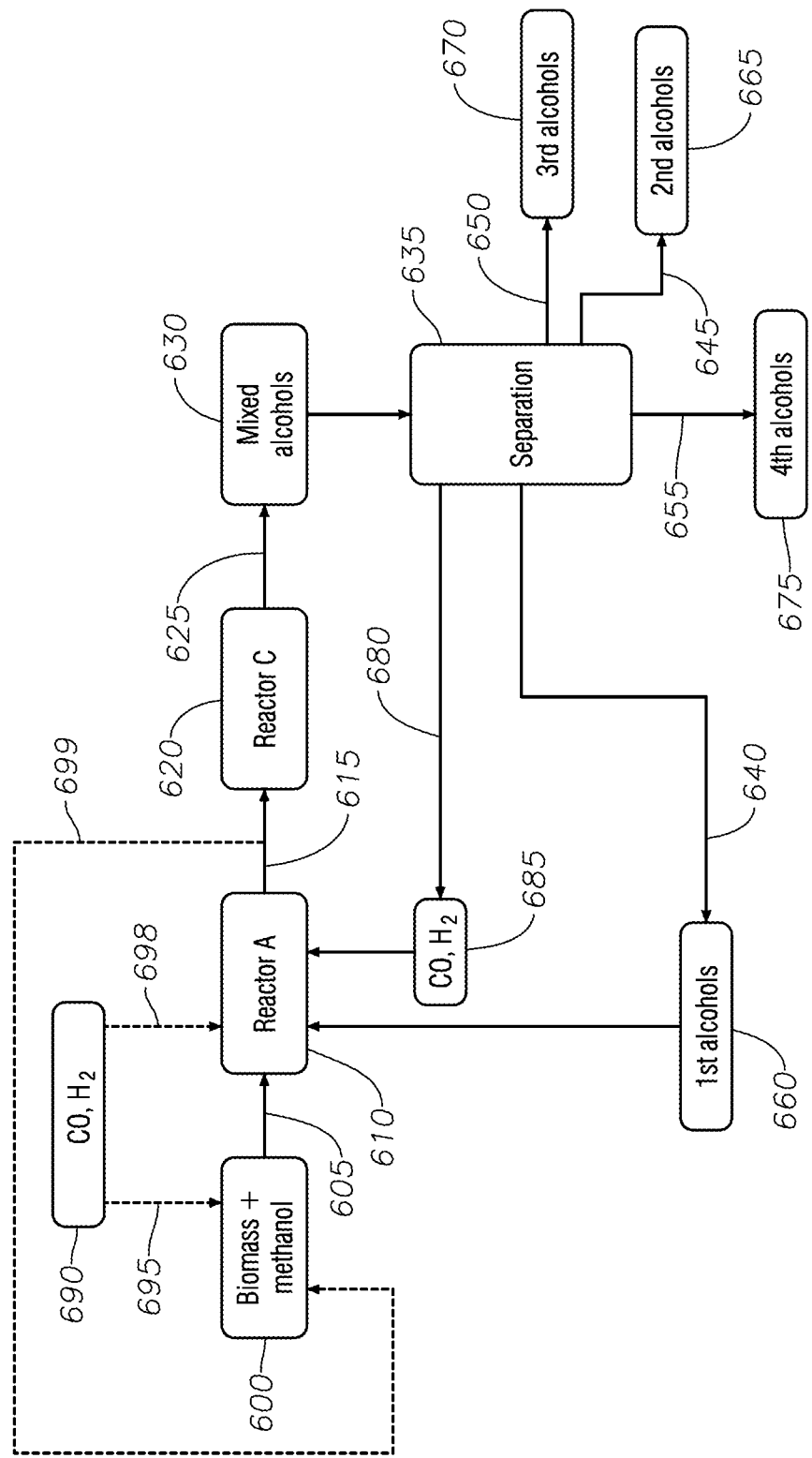
FIG. 11 is a flow diagram of a process for preparing alcohols from biomass according to another embodiment of the present disclosure and illustrating separation of mixed alcohols into multiple alcohol rich streams.

FIG. 11 illustrates a further process option according the present disclosure in which the separation of the mixed alcohols in separator (635) results in four alcohol rich streams based on boiling point. The light stream (640) is recycled to reactor A (610) and the three heavier alcohol rich streams (645), (650) and (655) may be subjected to further processing. It will be appreciated that the separation of the mixed alcohols into multiple alcohol rich streams may also be present in any one or more of the herein disclosed processes.

In an optional embodiment of the process, a portion of the effluent from reactor A comprising mixed alcohols may be recycled via stream (699) to the biomass/methanol (600) or to the reactor A (610) (not shown). Prior to this recycling, the effluent from reactor A may be subjected to a separation step wherein gases such as CO and H$_2$ are removed (not shown).

Alcohols to Ethers and Olefins

The present disclosure further relates to a two-stage process by which alcohols, particularly primary alcohols such as ethanol or 1-butanol are converted into distillate-range ethers and olefins utilizing Guerbet coupling followed by intermolecular dehydration. The ethers can be used, for example, as cetane-improvers in diesel fuel, while the olefins can be hydrogenated and blended with gasoline or oligomerized and hydrogenated to jet-range paraffins.

Embodiments of the herein disclosed processes utilize a first reaction in the presence of a heterogeneous catalyst to couple primary alcohols to higher alcohols. The higher alcohols may comprise mixtures of linear and branched alcohols. In a second reaction, the higher alcohols are dehydrated over a solid acid catalyst to olefins and ethers.

Primary Alcohol Coupling

In embodiments, a feed comprising primary alcohols are fed to reactor (D) that contains catalyst (D).

In some embodiments, the primary alcohol coupling is performed in a single reactor, the reactor containing one or more beds of catalyst (D).

The temperature of a catalyst bed may be from about 200° C. to about 500° C., preferably from about 250° C. to about 400° C., more preferably from about 280° C. to about 350° C.

The pressure in reactor (D) may be from about 15 psi (0.1 MPa) to about 1000 psi (6.9 MPa), or from about 100 psi (0.69 MPa) to about 1000 psi (6.9 MPa), or from about 200 psi (1.38 MPa) to about 500 psi (3.45 MPa).

The partial pressure of hydrogen in reactor (D) may be less than 100 psi (0.69 MPa), or less than 90 psi (0.62 MPa), or less than 80 psi (0.55 MPa) or less than 70 psi (0.48 MPa), or less than 60 psi (0.41 MPa).

In some embodiments, the weight hour space velocity (WHSV) in reactor (D) is from about 0.1 h$^{-1}$ to about 20 h$^{-1}$, or from about 0.1 h$^{-1}$ to about 10 h$^{-1}$, or from about 0.2 h$^{-1}$ to about 5 h$^{-1}$, or from about 0.5 h$^{-1}$ to about 5 h$^{-1}$.

In the present disclosure, yields are calculated on a carbon basis according to Equation 9 where $\dot{n}_{C,i}$ is the flow rate of carbon for species of category i.

$$Yield_i = Y_i = \frac{\dot{n}_{C,i,out}}{\dot{n}_{C,in}} \quad \text{Equation 9}$$

In some embodiments of the present disclosure, the yield of alcohols in the primary alcohol coupling reaction is at least about 20%, or at least about 25%, or at least about 30%, or at least about 35%, or at least about 40%, or at least about 45%, or at least about 50%, or at least about 55%, or at least about 60%, or at least about 65%.

At alcohol conversions below about 60%, conversion was calculated as the sum of all observed products according to Equation 10. This was performed since small changes in feed alcohol quantification can lead to large nonphysical fluctuations in the calculated conversion; carbon balances (carbon out divided by carbon in) ranged between 95 and 105 C %. The yield of unidentified gas chromatography (GC)-detected species was estimated by multiplying the unidentified GC area by the total yield of identified products divided by the total GC area of such products.

At elevated conversions where carbon balances are lower (85-95%), conversion was calculated based on the disappearance of the feed alcohol (Equation 11) since Equation 10 does not account for undetected heavy species which are more likely to be present at these conversions.

$$\text{Conversion} = X = \Sigma Y_i \qquad \text{Equation 10}$$

$$\text{Conversion} = X = \frac{\dot{n}_{C,\text{feed alcohol in}} - \dot{n}_{C,\text{feed alcohol out}}}{\dot{n}_{C,\text{feed alcohol in}}} \qquad \text{Equation 11}$$

Selectivities are calculated on a carbon basis from the yield and the relevant metric for conversion based on Equation 12.

$$\text{Selectivity}_i = S_i = \frac{Y_i}{X} \qquad \text{Equation 12}$$

In some embodiments of the present disclosure, the selectivity to alcohols in the alcohol coupling reaction is at least about 45%, or at least about 50%, or at least about 55%, or at least about 60%, or at least about 65%, or at least about 70%, or at least about 75%, or at least about 80%.

In other embodiments of the present disclosure, the selectivity to alcohols in the alcohol coupling reaction is between about 45% and about 80%, or between about 50% and about 75%.

In some embodiments of the present disclosure, the selectivity to primary linear alcohols in relation to all alcohols formed in the alcohol coupling step is at least about 80%, or at least about 85%, or at least about 90%, or at least about 95%, or at least about 96%, or at least about 97%, or at least about 98%, or at least about 99%.

In some embodiments, the selectivity to primary alcohols is between about 80% and about 99.5%.

A feature of the presently disclosed alcohol coupling reaction is the very high selectivity to primary linear alcohols in relation to all alcohols formed. In some embodiments, selectivities as high as 85% or greater are achieved at conversions of close to 70%.

In some embodiments the yield of primary linear alcohols is between about 10% and about 99%.

Typically, selectivity to primary linear alcohols, such as 1-butanol and 1-hexanol is very high at low conversions and can be as high as greater than 99%. As conversion is increased, selectivity to the primary linear alcohols decreases and the selectivity to primary branched alcohols, such as 2-ethyl-1-butanol and 2-ethyl-1-hexanol, increases. Advantageously, by controlling conversion, the ratio of primary linear alcohols to primary branched alcohols may be varied.

Alcohol Coupling Catalyst ('Catalyst D')

Catalyst (D) is a heterogeneous catalyst comprising one or more Group A oxides, said Group A oxides being oxides of Mg, Ca, Zn, Mn, Sr, Si and Zr; one or more Group B oxides, said Group B oxides being one or more oxides of Al, La, Ga, Ce, Fe, Sc, Cr, P and V; and combinations of both Group A and Group B oxides, and, optionally, one or more of Cu, Ni, Pt, Pd, Rh, Co, Cs and Rb.

Catalyst (D) may be a heterogeneous catalyst comprising one or more oxides of Mg, Ca, Zn, Sr, Al and Ce. In some embodiments the catalyst (D) comprises one of an oxide of Mg, Ca, Zn, Sr, Al and Ce.

Catalyst (D) may be a heterogeneous catalyst comprising one or more oxides of Mg, Ca and Zn, one or more oxides of Al, La, Ga, Ce, Fe and Cr, and one or more of Cu, Ni, Pt, Pd, Rh and Co.

Catalyst (D) may be a heterogeneous catalyst comprising one or more oxides of Mg, Ca and Sr, one or more of P and V, and, optionally, one or more of Cu, Ni, Pt, Pd, Rh and Co.

Catalyst (D) may be a heterogeneous catalyst comprising Al and Si metal oxides and one or more of Cs and Rb.

In some embodiments the weight percent of the one or more of Cu, Ni, Pt, Pd, Rh and Co in catalyst (D) is up to about 1 wt. %, or from about 0.01 wt. % to about 1 wt. %, or from about 0.01 wt. % to about 0.5 wt. %, or from about 0.01 wt. % to about 0.4 wt. %, or from about 0.01 wt. % to about 0.3 wt. %, or from about 0.01 wt. % to about 0.2 wt. %, or from about 0.02 wt. % to about 0.15 wt. %, based on the total weight of the catalyst.

In some embodiments catalyst (D) comprises Mg and Al oxides and Cu. The weight weight percent of Cu is preferably 0.05 wt. % to 1.0 wt. %, or 0.05 wt. % to 0.5 wt. %, or 0.05 wt. % to 0.2 wt. %, based on the total weight of the catalyst.

Generally, catalyst (D) having the desired activity can have a molar ratio of one or more of Mg, Ca, Zn, Mn, Sr, Si and Zr to one or more of Al, La, Ga, Ce, Fe, Sc, Cr, 0 and V of about 10 to about 1, for example about 5 to about 1, about 4 to about 1, or about 3 to about 1. In some embodiments, the molar ratio of one or more of Mg, Ca, and Zn to one or more of Al, La, and Ga, can be at least about 10, for example at least about 5, at least about 4, or at least about 3. Additionally, or alternately, the molar ratio of one or more of Mg, Ca, and Zn, to one or more of Al, La, and Ga can be about 10 or less, for example about 5 or less, about 4 or less, or about 3 or less.

In some preferred embodiments, the molar ratio of Mg to Al, can be at least about 5, for example at least about 4 or at least about 3. In such embodiments, the molar ratio of Mg to Al can optionally be about 5 or less, for example about 4 or less, or about 3 or less.

Preferably, catalyst (D) is reduced prior to use. Catalyst (D) may be reduced through treatment with hydrogen at elevated temperature. Typical temperatures may be in the range 250° C. to 450° C., between 300° C. and 400° C.

Catalyst Form

Catalysts (D) as described herein can employ the catalyst in a powder form, prepared, for example, by co-precipitation techniques or wet impregnation techniques, such as incipient wetness impregnation. Alternately, or additionally, the powder can be formulated into catalyst particles, such as by extrusion. Such catalyst particles, or extrudates, may be bound using one or more binders typically employed in the art.

Reactor Types

Various types of reactors (reactor D) may provide a suitable configuration for performing alcohol coupling. Suitable reactors may include fixed bed reactors, moving bed reactors, and slurry bed reactors. In some preferred embodiments the reactor is a fixed bed reactor.

It is noted that the activity and/or selectivity of a catalyst for alcohol coupling may vary as the catalyst is exposed to increasing amounts of primary alcohol.

In embodiments where a catalyst can be removed from the reactor for regeneration and recycle during operation of the reactor, such as a moving bed reactor, catalyst can be removed and replaced with regenerated catalyst.

In embodiments where fixed bed reactors are utilized, the reactors may comprise one or more beds of catalyst powder, particles or extrudates. Each bed may comprise the same catalyst, or, alternately, beds may comprise different catalysts. Where different catalysts are utilized, they may vary in terms of one or more of metal loading, metal type and basic metal oxide type.

For example, in one embodiment, a given reactor may contain more than one catalyst bed, each of which contain the same, for example, CuMgAl oxide catalyst. In another embodiment, a given reactor may contain more than one catalyst bed, wherein at least one bed has a different catalyst to another bed. For example one bed may contain a CuMgAl oxide having a particular Cu loading and another bed may contain a CuMgAl oxide catalyst having a different Cu loading. In another embodiment, one bed may contain, for example, a CuMgAl oxide catalyst and another bed may contain a different catalyst.

Alcohol Dehydration

In embodiments the higher alcohols formed through alcohol coupling are contacted with catalyst (E) in reactor (E) to dehydrate the higher alcohols to ethers and olefins.

In some embodiments, the dehydration is performed in a single reactor, the reactor containing one or more beds of catalyst (E).

The temperature of a catalyst bed may be from about 100° C. to about 200° C., or from about 120° C. to about 180° C., or from about 130° C. to about 170° C., or from about 135° C. to about 165° C.

In some embodiments, the weight hour space velocity (WHSV) in reactor (E) may be from about 0.1 to about 10 or from about 0.2 to about 5 or from about 0.5 $h^{-1}$ to about 5 $h^{-1}$.

Dehydration Catalyst ('Catalyst E')

In some embodiments catalyst (E) is a solid acid catalyst. Exemplary solid acid catalysts may comprise one or more of acidic resins, alumina and aluminosilicates, heteropoly acids, and tungsten and molybdenum functionalized oxides.

Non-limiting examples of acidic resins include resins available under the trade names Amberlyst™, Nafion™ and Dowex™.

Suitable examples of Amberlyst™ resins include Amberlyst™ 15, 16, 31, 35, 39, 70 and 121. Suitable examples of Nafion™ resins include Nafion™ H and NR-50. Suitable examples of Dowex™ resins include Dowex™ 50Wx2, 50Wx4 and 50Wx8.

Non-limiting examples of aluminosilicates include $SiO_2$—$Al_2O_3$, and zeolites such as H-β, H-Y, and H-ZSM-5.

Non-limiting examples of heteropoly acids include tungstophosphoric acid, silicotungstic acid, molybdotungstic acid, and molybdophosphoric acid, Non-limiting examples of tungsten and molybdenum functionalized oxides include $WO_x/ZrO_2$, $WO_x/TiO_2$, $WO_x/Al_2O_3$, $MoO_x/ZrO_2$, $MoO_x/TiO_2$, and $MoO_x/Al_2O_3$, wherein x is 1-3.

Model Alcohol Dehydrations

Experiments were performed individually on the major alcohols observed in the alcohol coupling step, namely the primary linear alcohols 1-butanol and 1-hexanol. These alcohols were dehydrated to di-n-butyl ether and di-n-hexyl ether respectively at about 97% selectivity.

The only other products observed were olefins. This established that primary linear alcohols were dehydrated to ethers with high selectivity with only small amounts of olefins formed.

Dehydrations were also performed on the primary branched alcohols 2-ethyl-1-butanol and 2-ethyl-1-hexanol, which are formed in increasing amounts in the alcohol coupling step as conversion increases. On dehydration, these alcohols are more selective to olefins than the linear alcohols. 2-ethyl-1-butanol was about 65% selective to 3-methylpentenes and 2-ethyl-1-hexanol about 75% selective to 3-methylheptenes.

Dehydration of mixed alcohol feeds was examined under controlled reactant ratios to establish whether crossed products were formed. Mixtures of 1-butanol and 2-ethyl-1-hexanol were examined with molar ratios of 8:1, 2:1, 1:1, and 1:2.

Feeds with higher 1-butanol contents show higher ether selectivities and lower olefin selectivities. No species other than light olefins and ethers were observed. The conversion of a 1:1 molar ratio of 1-butanol and 2-ethyl-1-hexanol led to an ether selectivity of 59% and an olefin selectivity of 33% at 66% feed conversion. The conversion of 1-butanol was 79% while that of 2-ethyl-1-hexanol was lower at 59%. The cross-etherification product 1-butoxy-2-ethylhexane was positively identified via GC-MS-EI, clearly showing that cross-etherification occurred between linear and branched alcohols.

Model alcohol mixtures representative of ethanol coupled products from the alcohol coupling step were prepared and subjected to dehydration. Mixtures containing 1-butanol, 1-hexanol, 2-ethyl-1-butanol and 2-ethyl-1-hexanol were prepared having linear:branched ratios of 12.5, 5.3, 3.2 and 2.0.

The mixtures reacted to 65.0-69.5% conversion with ether selectivities ranging from 65.0-81.8%. Cross-etherification was observed between the various alcohols with ethers positively identified based on molecular weight via GC-MS-FI. As in the etherification of butanol-ethylhexanol mixtures, ether and olefin selectivities could be directly correlated with the linear:branched alcohol feed ratio, though ether selectivities were slightly lower than with the two-component feed. This implies that performing Guerbet condensation at higher conversions where the linear:branched alcohol ratio is lower will result in lower ether selectivities, though these ethers will be larger and therefore possess higher energy densities. The olefins were almost entirely 3-methylpentenes and 3-methylheptenes derived from the branched alcohols. These could be partially hydrogenated and utilized in gasoline or oligomerized with solid acids and hydrogenated to jet-range paraffins.

Combined Alcohol Coupling and Dehydration

After validation of the individual reaction stages, the two were combined in series to produce a mixture of distillate-range ethers from ethanol. In one embodiment ethanol condensation was first carried out at 42% conversion using a hydroxyapatite catalyst to produce C4+ alcohols at 82% selectivity. The product distribution remained steady for over 400 h time-on-stream.

Water is known to inhibit dehydration reactions and therefore is advantageously removed from the coupling products prior to dehydration. In some embodiments, molecular sieves may be used to reduce the water content of the ethanol derived alcohol mixture from, for example, 15 wt. % to less than, for example, 0.5 wt. %.

In some embodiments, unreacted ethanol may be removed via distillation since dehydration reactions involving ethanol would produce significant amounts of volatile C4-C6 ethers. The major components after ethanol removal are, for example, 1-butanol (about 50 wt. %), 2-ethyl-1-butanol (about 15 wt. %), 1-hexanol (about 12 wt. %), and 2-ethyl-1-hexanol (about 4 wt. %). In some embodiments, about 80 mol. % of the alcohols in this mixture are linear.

The alcohol mixture may then be converted to ethers over, for example, a solid acid catalyst, with, in some embodiments, about 75% alcohol conversion, about 70% ether selectivity, and about 10% olefin selectivity. This demonstrates that combination of the two catalytic steps in series necessitates only conventional separation processes already common in alcohol purification (i.e. distillation and drying with molecular sieves).

Assuming ethanol coupling is performed at, for example about 50% conversion with about 77% selectivity to alcohols, in some embodiments the product may then be separated into four streams: water, ethanol, olefins, and C4+ alcohols with other heavy by-products. The ethanol may be recycled to the alcohol coupling reactor. The alcohols and heavy by-products may be fed to a dehydration reactor. The selectivities of the dehydration process are directly linked to the ratio of linear:branched alcohols in the dehydration feed. The product stream from the dehydration reactor may be separated into four streams: olefins, ethers, water, and by-products.

In some embodiments, the olefins may be suitable for gasoline blending after partial hydrogenation. Alternatively, or additionally, the olefins may be combined with the olefins produced during alcohol coupling into a stream which may be oligomerized via acid or metal catalysis and then hydrogenated to jet-range paraffins.

In some embodiments, oligomerization may be 80% selective to the distillate range since oligomerization of C4-rich streams is selective to this range and the subsequent hydrogenation is well-established to be a highly selective process.

In some embodiments, the overall process demonstrates about a 60% yield of diesel-range ethers and about a 15% yield of jet-range paraffins with an overall about 75% distillate fuel yield from ethanol.

To understand the sensitivity of these yields to the conversion at which the alcohol coupling reactor is operated, correlations can be drawn between ethanol conversion and alcohol selectivity, olefin selectivity, and the linear:branched alcohol ratio. These can then be combined with correlations between the dehydration feed composition and product selectivities to predict overall process yields as a function of alcohol coupling conversion.

For example, in one embodiment, increasing ethanol conversion from about 10 to about 60% shifts overall ether yields from about 77 to about 59% while olefin yields increase from about 5 to about 16%, with total distillate yields of about 82 to about 75%. Combined with the maximum theoretical ethanol yield achievable from glucose fermentation (67% carbon basis), this technology may be used to produce distillate fuel from sugars at yields of, some embodiments, 50-55%.

While only conventional separation schemes are likely required in the herein disclosed processes (e.g. distillation, adsorption with molecular sieves, liquid-liquid extraction), the person of ordinary skill in the art would appreciate that these separations may be performed in a multitude of ways depending on how the process is designed. For example, removal of water from ethanol condensation products may only require molecular sieves if condensation is performed at low conversions. Operation at higher conversions may require both distillation and molecular sieves. Operation at yet higher conversions would additionally allow for the production of a biphasic product, thus water removal would only occur after C4+ organic products are removed via decantation. Such a phase separation may also be induced via the recycling of a heavy phase if this improved process economics.

Compared to conventional ethanol-to-distillate technologies, the herein disclosed process possesses several benefits. The C8+ ethers have much higher cetane than the products from acid-catalyzed olefin oligomerization. These ethers also have lower freezing points than linear paraffins of the same carbon number that can be produced through metal-catalyzed olefin oligomerization (followed by hydrogenation). The freezing points of dodecane and hexadecane, for example, are −10 and 18° C., respectively, while those of di-n-hexyl ether and di-n-octyl ether are −43 and −8° C., respectively. The herein disclosed process additionally uses solely inexpensive heterogeneous catalysts and does not require added solvents.

Alcohol to Ethers and Olefins Process Embodiments

Figure 12:
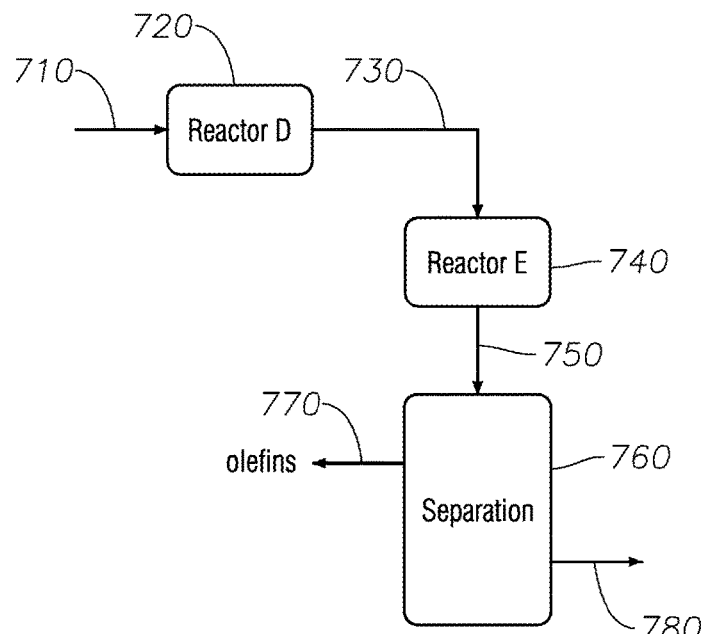
FIG. 12 is a flow diagram of a process for producing ethers and olefins from primary alcohols according to one embodiment of the present disclosure.

Referring first to FIG. 12, the process flow diagram illustrates the production of olefins and ethers from alcohols according to one embodiment of the present disclosure.

In a first step, a feed comprising primary alcohols is fed via line (710) to reactor (720) which contains one or more beds of heterogeneous catalyst. The effluent from the reactor, which comprises higher alcohols, is fed via line (730) to reactor (740) which contains one or more beds of heterogeneous dehydration catalyst. The effluent from reactor (740), which comprises olefins and ethers, is fed via line (750) to separation unit (760) which separates the olefins and ethers into olefin rich stream (770) and ether rich stream (780).

Figure 13:
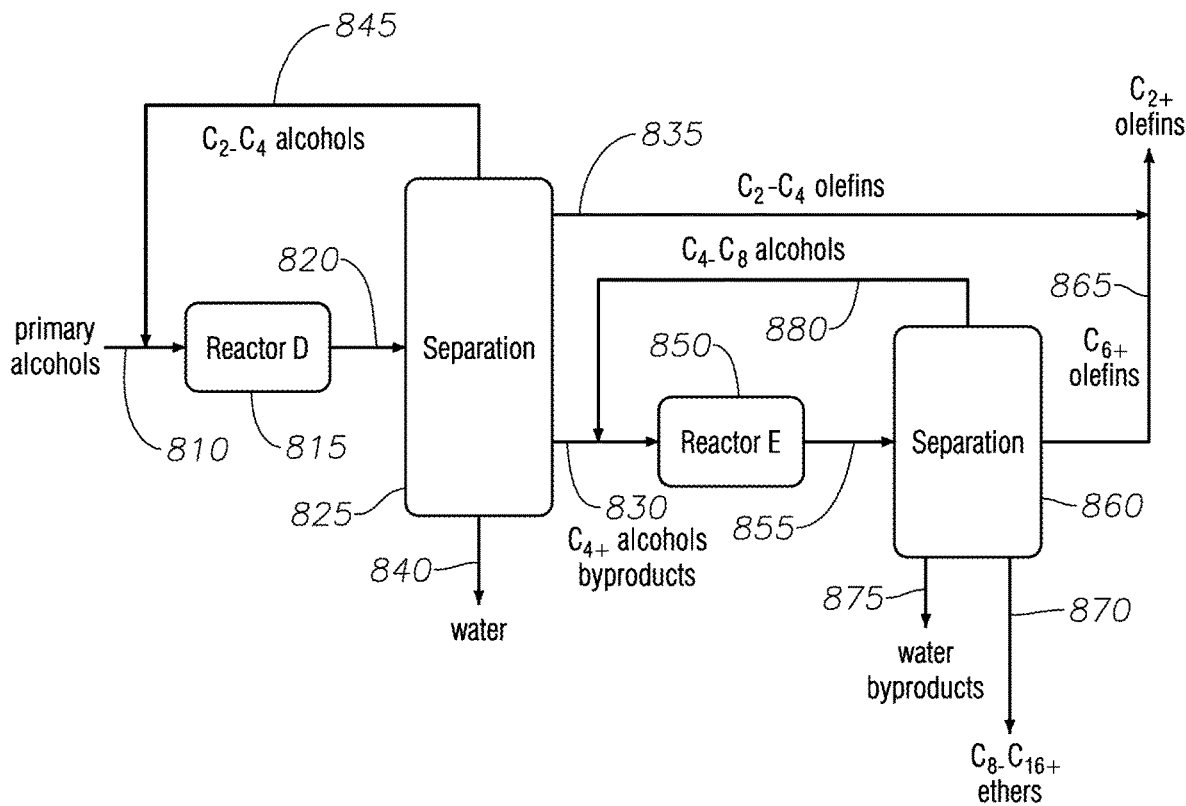
FIG. 13 is a flow diagram of a process for producing ethers and olefins from primary alcohols according to another embodiment of the present disclosure.

Referring to FIG. 13, the process flow diagram illustrates the production of olefins and ethers from alcohols according to another embodiment of the present disclosure.

In a first step, a feed comprising primary alcohols is fed via line (810) to reactor (815) which contains one or more beds of heterogeneous catalyst. The effluent from the reactor, which comprises higher alcohols, is fed via line (820) to separation unit (825) which separates the effluent into four streams. Stream (845) comprises light alcohols, for example in the $C_2$-$C_4$ range; stream (835) comprises olefins, for example in the $C_2$-$C_4$ range; stream (830) comprises heavier alcohols, for example greater than $C_4$; and stream (840) comprises water.

The light alcohol stream (845) is recycled to reactor (815) to build higher chain length compounds. The heavier alcohol stream (830) is fed to dehydration reactor (850) the effluent from which is fed via line (855) to separation unit (860) which separates the effluent into four streams.

Stream (880) comprises unreacted alcohols which are recycled back to the dehydration reactor feed (830); stream (865) comprises olefins, for example greater than $C_6$, the stream is combined with olefin stream (835) from separation (825); stream (870) comprises ethers, for example $C_8$-$C_{16+}$ ethers; and stream (875) comprises water and by-products.

Figure 14:
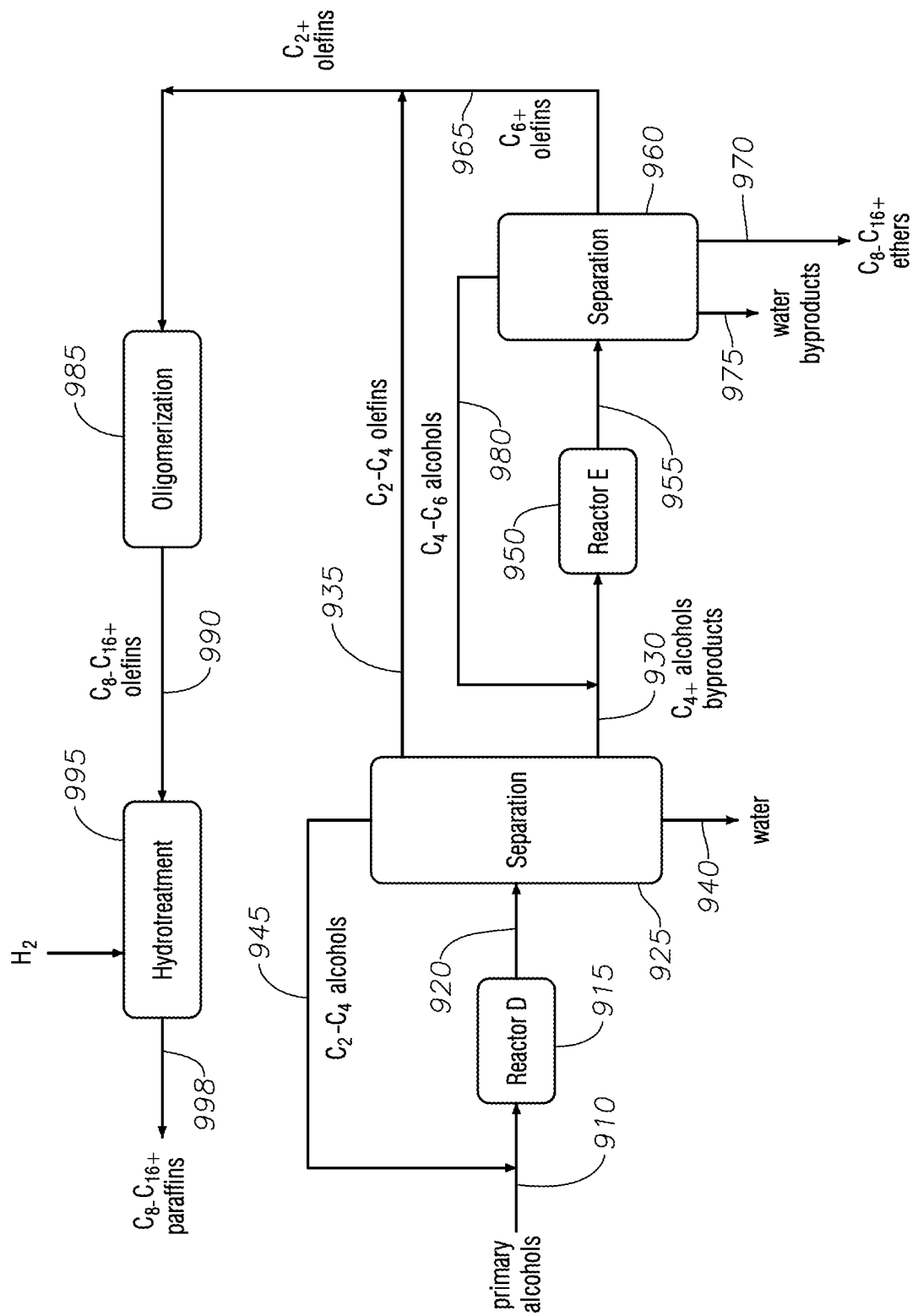
FIG. 14 is a flow diagram of a process for producing distillate range hydrocarbons and ethers from primary alcohols according to another embodiment of the present disclosure.

FIG. 14 illustrates a process flow diagram similar to that of FIG. 13, with the addition that combined olefin streams (935) and (965) are fed to reactor (985) which contains one or more beds of an olefin oligomerization catalyst. The effluent from this reactor, which contains higher olefins, for example in the range $C_8$-$C_{16+}$, is fed via line (990) to reactor (995) which contains one or more beds of a hydrotreating catalyst. Hydrogen is also fed to the reactor, resulting in effluent stream (998) which comprises higher paraffins, for example in the range $C_8$-$C_{16+}$.

Biomass to Ethers and Olefins Process Embodiments

Any one of the herein disclosed embodiments of the processes to produce alcohols from biomass may be combined with any one of the herein disclosed embodiments of processes to produce ethers and olefins from alcohols to provide processes to produce ethers and olefins from biomass.

In one embodiment, the $2^{nd}$ alcohols produced in the processes according to any one of FIGS. 6 to 10 may comprise the feed (710) in FIG. 12.

In another embodiment, the $2^{nd}$ alcohols produced in the processes according to any one of FIGS. 6 to 10 may comprise the feed (810) in FIG. 13.

In another embodiment, the $2^{nd}$ alcohols produced in the processes according to any one of FIGS. 6 to 10 may comprise the feed (910) in FIG. 14.

In another embodiment, any one or more of the $2^{nd}$, $3^{rd}$ or $4^{th}$ alcohols produced in the process according to FIG. 11 may comprise the feed (710) in FIG. 12.

In another embodiment, any one or more of the $2^{nd}$, $3^{rd}$ or $4^{th}$ alcohols produced in the process according to FIG. 11 may comprise the feed (810) in FIG. 13.

In another embodiment, any one or more of the $2^{nd}$, $3^{rd}$ or $4^{th}$ alcohols produced in the process according to FIG. 11 may comprise the feed (910) in FIG. 14.

EXAMPLES

Example 1: Preparation of CuMgAl Oxide Catalyst

The catalyst was prepared using a co-precipitation technique. In a typical synthesis, a 150 mL solution of dionized (DI) water containing 0.06 mol of $Mg(NO_3)_2.6(H_2O)$, 0.025 mol of $Al(NO_3)_3.9(H_2O)$, and 0.015 mol of $Cu(NO_3)_2.3(H_2O)$ was added to a 187.5 mL solution of DI water containing 0.025 mol of $Na_2CO_3$ over the course of 1 h at 60° C. The pH was kept at 10 by the addition of a 250 mL 1 M NaOH solution. The combined solution was aged at 60° C. for 24 h and then washed and filtered. The filtered catalyst was dried in a 110° C. oven overnight. The dried catalyst was calcined at 460° C. for 12 h with a 5° C./min temperature ramp in an air atmosphere.

The Mg, Al, and Cu content of the catalyst were determined after dissolution in 3 M $HNO_3$ with inductively coupled plasma atomic emission spectroscopy (ICP-AES) using a PerkinElmer Plasma 400 at wavelengths of 279.079, 396.152, 324.754 nm for Mg, Al, and Cu, respectively. The Al/Cu/Mg molar ratio was 5.1/3.5/12.0. The surface area of the catalyst powder as determined by the Brunauer-Emmett-Teller (BET) method using a Micrometrics ASAP 2020 Plus was about 250 $m^2/g$.

Example 2: Conversion of Whole Biomass

Conversions were performed in a flow reactor comprising a packed bed of catalyst powder in a ⅜" tube with a 2" length of inert glass beads at the beginning of the reactor with 2.5" of quartz wool on either side to hold the catalyst bed in place. A biomass solubilization bed was located upstream of the catalyst bed. The reactor was enclosed in an aluminum heating block that was heated by a clamshell furnace. The liquid feed was pumped using a 1SM Eldex HPLC pump. An optional gas co-feed ($CO/H_2$) was fed through a Brooks gas flow controller.

The pressure in the reactor was maintained by an Equilibar dome-loaded back pressure regulator using argon as the pilot fluid. Liquid product was collected in a collection vessel that was chilled using a circulating temperature bath. Effluent from the reactor was bubbled through the chilled liquid products via a dip tube below the liquid level. The collection vessel was maintained at 43 psi (300 kPa) to reduce evaporation of the products. The gas was analyzed using an online gas chromatograph (GC) equipped with a thermal conductivity detector (TCD) and a flame ionization detector. Liquid products were analyzed using a gas chromatograph equipped with a flame ionization detector (GC-FID). Response factors were obtained from calibrations using standard solutions.

In a typical experiment utilizing whole biomass, 1.2 g of calcined catalyst was loaded in a ⅜" stainless steel tube. The solubilization bed was filled with 1.87 g of maple wood (sieved between 355 and 180 μm) or cellulose (Avicel PH-101) and packed with quartz wool on either end of the bed. The catalyst was reduced at 350° C. with a 1° C./min ramp and a 4 h hold in 100 mL/min of $H_2$ and then returned to ambient temperature.

At the start of the reaction, the dome loaded back pressure regulator was increased to 2000 psi (13.8 MPa) and the catalyst bed heated to 300° C. with a 10° C./min temperature ramp. The solubilization bed was kept at ambient temperature. Methanol was pumped with an HPLC pump through the solubilization bed to the catalyst bed at 0.431 mL/min. When the two beds were at steady state, the collection vessel was drained and the solubilization bed ramped from 20 to 190° C. at 10° C./min and held for 1.5 h. The solubilization bed was then ramped to 230° C., 300° C., and then 330° C. at the same ramp rate and hold time. An online gas sample was taken every 1.5 h, and the liquid products collected after every temperature hold. The liquid and gas products were analyzed as described previously.

With this setup, 92.2 wt. % of the maple wood and 100 wt. % of the cellulose was solubilized during the reaction. The overall carbon yield from the solubilized maple wood was 68.9% while the carbon yield from cellulose was 73.3% as shown in Table 1. The total carbon yield is based on the sum of moles of carbon in the products and the moles of carbon in the reactant (cellulose, or maple wood). Due to methanol incorporation in the liquid products, the carbon yield can be above 100%, however in Table 1 the carbon yield excludes products incorporating methanol.

TABLE 1

| | Maple Wood | Cellulose |
|---|---|---|
| Overall carbon yield (% C) | 68.9 | 73.3 |
| Product selectivity | | |
| C2-C6 mono-alcohols | 27.3 | 31.8 |
| C6-C7 cyclic alcohols | 18.9 | 42.2 |
| C8-C10 cyclic alcohols | 12.2 | — |
| Phenolics (lignin) | 7.3 | — |
| Ethers and esters | 13.1 | 10.5 |
| Unknown C2-C6 alcohols, ethers and esters | 13.5 | 9.1 |
| Dimers and trimers (lignin) | 7.8 | — |

Example 3: Methanol Synthesis in a Two-Stage Reactor

To examine the extent of methanol reformed and the influence of temperature on methanol reforming, a solution of glycerol in methanol was fed to the reactor of Example 1. Subsequently, the effluent from the first reactor was fed to a second reactor which contained the same CuMgAl oxide catalyst, but operating at variable temperature.

Reaction conditions for the first reactor bed: 300° C., 2000 psi (13.8 MPa), 0.7102 g of catalyst, 1 $h^{-1}$ WHSV, 10 wt. % glycerol in methanol, 0.15 mL/min feed flow rate.

Reaction conditions for second reactor bed: 260-300° C., 2000 psi (13.8 MPa), 1.9672 g of catalyst, 0.36 h-1 WHSV, 10 wt. % glycerol in methanol, 0.15 mL/min feed flow rate.

FIG. 4 illustrates the % methanol reformed in the second reactor and indicates that, advantageously, significantly less methanol was reformed when the second reactor operated at 260° C. (22% reformed) relative to 300° C. (42% reformed).

FIG. 5 illustrates the carbon yield and product selectivity of supercritical methanol depolymerization and hydrodeoxygenation of glycerol at 300° C. in a first reactor and methanol synthesis in a second reactor at 260-300° C. It is evident that the temperature in the second reactor had minimal effect on carbon yield and product selectivity.

Example 4: Reactions at High Hydrogen Selectivity-High Pressure and CO—$H_2$ Co-Feed Reactions with either higher pressure or a 35%/65% CO—$H_2$ co-feed were examined. The CO—$H_2$ mixture composition was chosen to match the stoichiometric composition for methanol synthesis.

Reactions were performed with 10 wt. % glycerol in methanol at 2000 psi (13.8 MPa) and 3000 psi (20.7 MPa) without a co-feed, and 2000 psi (13.8 MPa) with a 200 mL/min CO—$H_2$ co-feed. The reactions at 2000 psi (13.8 MPa) and 3000 psi (20.7 MPa) without co-feeds were operated for 24 h time on stream while the reaction with the CO—$H_2$ co-feed was operated for 11 h. The liquid products and methanol reformed at each condition are shown in FIG. 1. The carbon yield was highest for the reaction at 2000 psi (13.8 MPa) with no co-feed at 148% compared to 130% carbon yield at 3000 psi (20.7 MPa with no co-feed and 108% carbon yield at 2000 psi (13.8 MPa) with a CO—$H_2$ co-feed. The lower carbon yield with the CO—$H_2$ co-feed was likely due to the reduced partial pressure of glycerol in the reactor which reduced the rate of C—C coupling reactions between methanol and glycerol. Although the carbon yields were different between the three reaction conditions, the liquid phase product selectivity was very similar. In all three reactions, the primary products were mono-alcohols (74-76% selectivity) with some selectivity to esters and ethers (4-6% selectivity). The selectivity to diols was low (0-1% selectivity).

The methanol reformed from each reaction is also shown in FIG. 1. At 2000 psi (13.8 MPa) without a gas co-feed the methanol reformed was 35%. When the pressure of the reactor was increased from 2000 psi (13.8 MPa) to 3000 psi (20.7 MPa) the extent of methanol reforming decreased to 26%. The CO—$H_2$ co-feed was set at 200 mL/min which gave an inlet composition of 71% gas and 29% liquid. The reaction at 2000 psi (13.8 MPa) with a CO—$H_2$ gas co-feed had a negative extent of methanol reforming of 11%. The negative methanol reforming indicates the co-feed of CO and $H_2$ synthesized methanol in the supercritical methanol depolymerization hydrodeoxgenation reactor. The co-feed experiment demonstrates that the CuMgAl oxide catalyst can act as a methanol synthesis catalyst.

Reaction conditions: 300° C., 2000-3000 psi (13.8-20.7 MPa), WHSV=0.5 h-1, 1.42 g of catalyst, 0.15 mL/min, 10 wt. % glycerol in methanol, 200 mL/min gas co-feed (35%/65% CO—$H_2$ mixture), 24 h TOS for reactions without a co-feed, 11 h TOS for CO—$H_2$ co-feed.

Example 5: Influence of Biomass Concentration

Several batch reactions were performed in which the concentration of biomass in methanol was varied (4 wt. %, 10 wt. %, and 20 wt. %) and the effect on total carbon yield and $C_2$-$C_6$ mono-alcohol selectivity determined. In a typical reaction, maple wood, reduced CuMgAl oxide catalyst, and methanol were mixed and added to a 7.5 mL volume steel reactor. The amount of maple wood for the 4 wt. %, 10 wt. %, 20 wt. % reactions were 100 mg, 200 mg, and 400 mg respectively, the amount of catalyst 100 mg, 200 mg, and 400 mg respectively and the amount of methanol, 2400 mg, 1800 mg, and 1600 mg respectively. The batch reactions were carried out by putting the batch reactors in a sand bath at 300° C. for 4 hours. The gas products were collected through a gas sampling valve at the top of the batch reactor while the liquid products were collected by opening the batch reactor and removing the liquids with a syringe.

A further reaction was performed using two charges of maple wood, designated as a 10+10 wt. % reaction. In a first step maple wood, catalyst, and methanol (200 mg, 200 mg, and 1800 mg respectively) were charged to a batch reactor and the reaction was run in the same way as the 10 wt. % reaction. The reactor was weighed before and after collecting gas products. After collecting the gas products, the reactor was opened and makeup methanol (which was equal to the mass of gas products from the difference in reactor weights) was added back to the reactor as well as 200 mg of additional maple wood. The reaction was then re-run at 300° C. for 4 h. The liquid and gas products were analyzed after the second reaction.

The results are collected in Table 2.

TABLE 2

| Biomass wt. % | 4 | 10 | 20 | 10 + 10 |
|---|---|---|---|---|
| Total carbon yield % | 104.9 | 92.9 | 77.4 | 88.6 |
| C2-C6 mono-alcohol selectivity | 44.7 | 38.0 | 28.6 | 35.0 |

Increasing the wt. % biomass from 4 wt. % to 20 wt. % resulted in a decrease in total carbon yield and mono-alcohol selectivity. However, the 10+10 experiment resulted in higher total carbon yield and higher selectivity to C2-C6 mono-alcohols, compared to the experiment in which a single 20 wt. % charge of biomass was utilized.

The results indicate that the presence of alcohols facilitate a high concentration of biomass in the solution. In a continuous process, operating at higher biomass loading (wt. %) equates to reduced volumetric throughput, with the result that a smaller reactor could be utilized, which has clear cost benefits.

Example 6: Alcohol Coupling Catalyst Preparation

A CuMgAl oxide catalyst was prepared by co-precipitation techniques. Three aqueous solutions were prepared as outlined in Tables 3 through 5.

TABLE 3

| Compounds and amounts for solution 1 | |
|---|---|
| Compound | Amount (g) |
| Mg(NO$_3$)$_2$•6H$_2$O | 35.51 |
| Al(NO$_3$)$_2$•9H$_2$O | 15.02 |
| Cu(NO$_3$)$_2$•3H$_2$O | 0.067 |
| H$_2$O | 240.0 |

TABLE 4

Compounds and amounts for solution 2

| Compound | Amount (g) |
|---|---|
| $Na_2CO_3$ | 4.24 |
| $H_2O$ | 300 |

TABLE 5

Compounds and amounts for solution 3

| Compound | Amount (g) |
|---|---|
| NaOH | 16.0 |
| $H_2O$ | 400 |

The amounts of magnesium, aluminum and copper precursors were such that the molar ratios were Cu/Al=0.0072 and Mg/Al=3.46. The nominal copper loading was 0.1 wt. %. Solution 1 was added to solution 2 which was at a temperature of 60° C., while adding solution 3 to maintain a pH of 9-11 (a pH meter was typically used to ensure this). On NaOH addition and mixing, a precipitate formed which was then aged for 20 hours at 60° C. The precipitate was isolated by filtration and washed with a solution of 25.44 g $Na_2CO_3$ in 240 g water and then at least three times with 60° C. deionized water. The catalyst was dried overnight at 60° C. and then calcined in air at 600° C. for 2 hours with 4° C./min temperature increase. The yield of catalyst was typically about 7 g. The catalyst was sized between 35-100 mesh sieves (range may vary). The catalyst was reduced in a flow of $H_2$ at ambient pressure and 350° C. prior to use.

Example 7: Coupling of Ethanol to Higher Alcohols

Continuous gas phase coupling of ethanol was performed in a fixed bed reactor containing 4.32 g CuMgAl oxide catalyst powder as prepared in Example 6.

The temperature in the reactor was 325 C and the total pressure 300 psi (2.1 MPa). Ethanol flow was adjusted to 0.134 and 0.600 mL/min to give WHSV, respectively, of 1.47 and 6.58 $h^{-1}$. $H_2$ flow was adjusted to fix $P_{Ethanol}:P_{H2}$ to a value of 4 (17.4 and 78 mL/min for, respectively, 1.47 and 6.58 $h^{-1}$). The partial pressure of $H_2$ was 60 psi (0.41 MPa).

Table 6 shows conversion and yields to products obtained in the tests.

TABLE 6

| WHSV ($h^{-1}$) | 6.58 | 1.47 |
|---|---|---|
| Contact time (s $kg_{cat}$/mol) | 25.2 | 113.1 |
| Conversion (%) | 54.63 | 67.92 |
| Alcohol | 33.84 | 39.32 |
| Primary linear alcohol | 30.49 | 34.63 |
| Primary branched alcohols | 2.47 | 3.25 |
| Secondary alcohols | 0.43 | 0.96 |
| Methanol | 0.45 | 0.48 |
| Aldehyde | 6.50 | 6.99 |
| Ketone | 1.43 | 2.61 |
| Ester | 9.23 | 15.11 |
| Ether | 0.21 | 0.68 |
| Paraffin | 0.11 | 0.15 |
| Olefin | 0.26 | 0.38 |
| Aromatic | 0.00 | 0.00 |
| Unidentified | 3.04 | 2.68 |

As WHSV increased and contact time decreased, ethanol conversion decreased. Alcohols were the major product, but at higher conversion (ca. 68%), increasing amounts of esters, aldehydes and olefins were produced. It is envisaged that at lower conversions, yields of alcohols would be even higher.

Table 7 shows the selectivity to products obtained in the tests.

TABLE 7

| WHSV ($h^{-1}$) | 6.58 | 1.47 |
|---|---|---|
| Contact time (s $kg_{cat}$/mol) | 25.2 | 113.1 |
| Conversion (%) | 54.63 | 67.92 |
| Alcohol | 61.95 | 57.91 |
| Primary linear alcohol | 55.82 | 50.37 |
| Primary branched alcohols | 4.53 | 5.42 |
| Secondary alcohols | 0.78 | 1.42 |
| Methanol | 0.83 | 0.70 |
| Aldehyde | 11.90 | 10.29 |
| Ketone | 2.61 | 3.94 |
| Ester | 16.90 | 22.23 |
| Ether | 0.38 | 1.00 |
| Paraffin | 0.21 | 0.22 |
| Olefin | 0.48 | 0.56 |
| Aromatic | 0.00 | 0.00 |
| Unidentified | 5.57 | 3.93 |

At the lower conversion, the fraction of primary linear alcohols relative to all alcohols was high. As conversion increased, increasing amounts of primary branched alcohols were produced.

Figure 15:
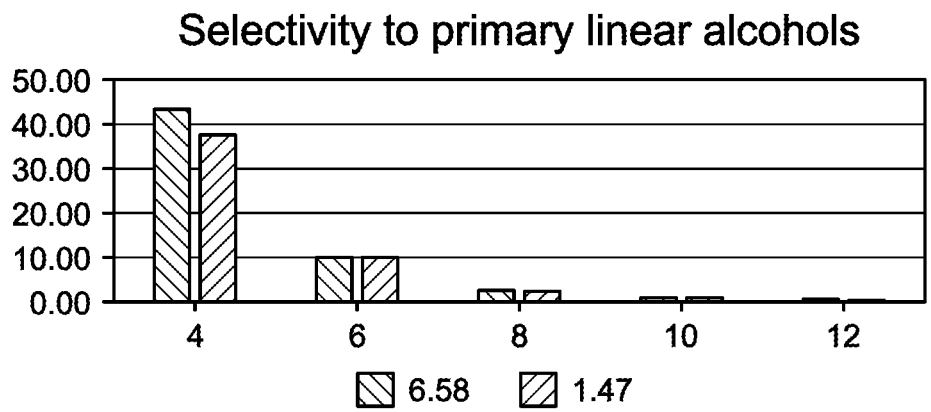
FIG. 15 is a bar chart showing selectivity to primary linear alcohols at different weight hour space velocities.

FIG. 15 illustrates the selectivity to primary linear alcohols based on carbon number and at different WHSV. Only even carbon numbered primary linear alcohols were produced, and 1-butanol and 1-hexanol were the only primary linear alcohols observed. As residence time increased, slightly increasing amounts of higher primary linear alcohols were observed.

Figure 16:
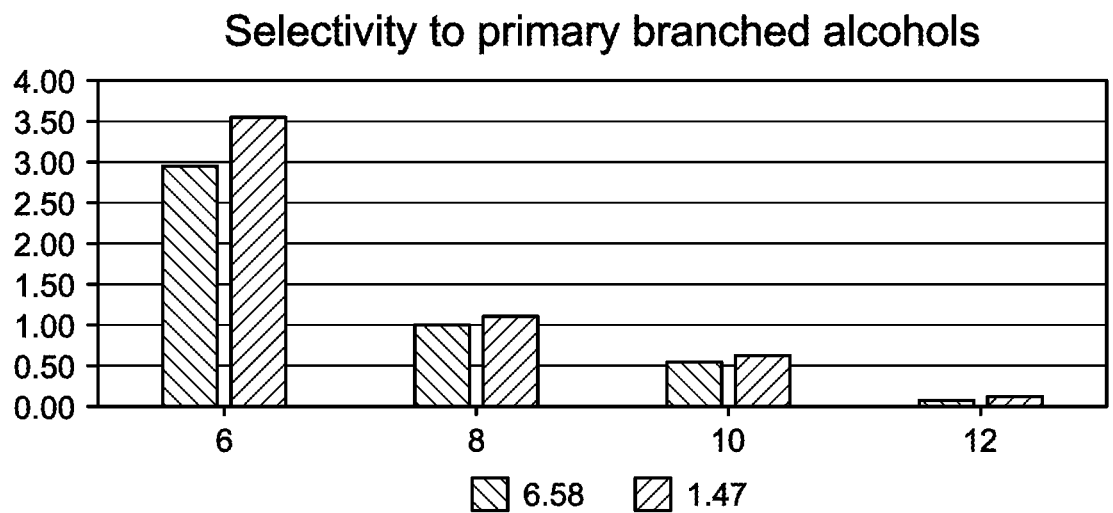
FIG. 16 is a bar chart showing selectivity to primary branched alcohols at different weight hour space velocities.

FIG. 16 illustrates the selectivity to primary branched alcohols based on carbon number and at different residence times. Only even carbon numbered primary branched alcohols were produced. As residence time increased, increasing amounts of higher primary branched alcohols were observed.

Figure 17:
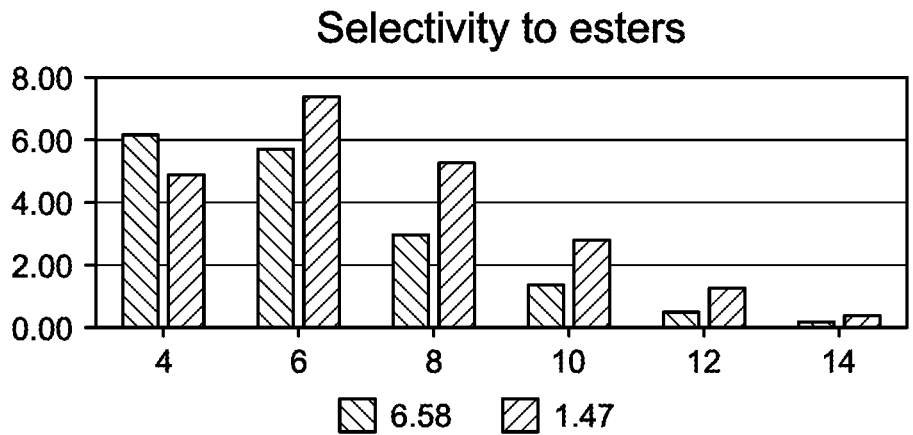
FIG. 17 is a bar chart showing selectivity to esters at different weight hour space velocities.

FIG. 17 illustrates the selectivity to esters based on carbon number and at different residence times. As residence time increased, increasing amounts of esters were observed, particularly C6+ esters.

Example 8: General Method for Alcohol Dehydration

Dehydration reactions were performed in a 45 mL Parr batch reactor with a 2.22 cm stir rod. Solid acid catalyst Amberlyst™ 70 was crushed and sieved to <177 μm and dried at 110° C. prior to reaction. In a typical reaction, 15 g of feed were first added to the reactor along with 750 mg of Amberlyst™ 70. The reactor was then sealed and pressurized with argon to about 290 psi (2 MPa) stirring at 750 rpm. The temperature was then increased to 150° C. with a ramp time of ~10 minutes prior to a 24 h hold. After 24 h the reactor was immediately submerged in an ice bath and cooled to <15° C. to minimize loss of volatile components.

After depressurization, the liquid products and catalyst were collected. The reactor and reactor head were then thoroughly rinsed (~75 mL total) with 1,4-dioxane to ensure full product collection. The resulting solution was then mixed and filtered through a 0.22 μm syringe filter. This solution was then further diluted in dioxane (20:1 by volume), and 1-pentanol was added as an internal standard prior to analysis. The solution was analyzed by gas chromatography (GC).

Example 9: Dehydration of Single-Component Alcohol Feeds

Following the method of Example 8, dehydrations were performed individually on the major alcohols observed in the alcohol coupling step, namely the primary linear alcohols 1-butanol and 1-hexanol. These alcohols were dehydrated to di-n-butyl ether and di-n-hexyl ether respectively at about 97% selectivity. The only other products observed were olefins.

Figure 18:
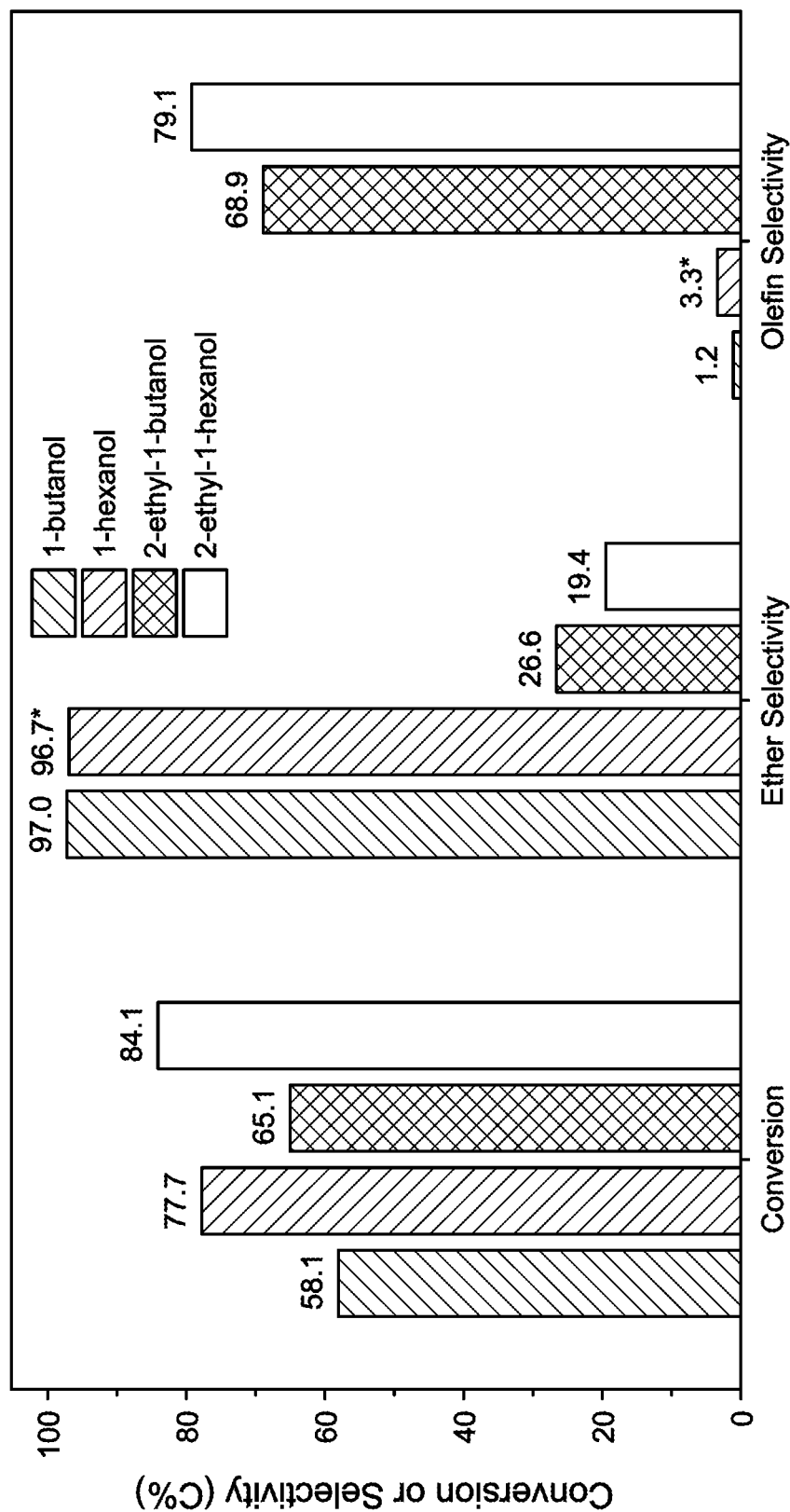
FIG. 18 is a bar chart showing alcohol dehydration conversions and selectivities.

Dehydrations were also performed on the primary branched alcohols 2-ethyl-1-butanol and 2-ethyl-1-hexanol. These alcohols are more selective to olefins than the linear alcohols. 2-ethyl-1-butanol was about 65% selective to 3-methylpentenes and 2-ethyl-1-hexanol about 75% selective to 3-methylheptenes. FIG. 18 illustrates the conversions and selectivities of the single-component alcohol feeds.

Figure 19:
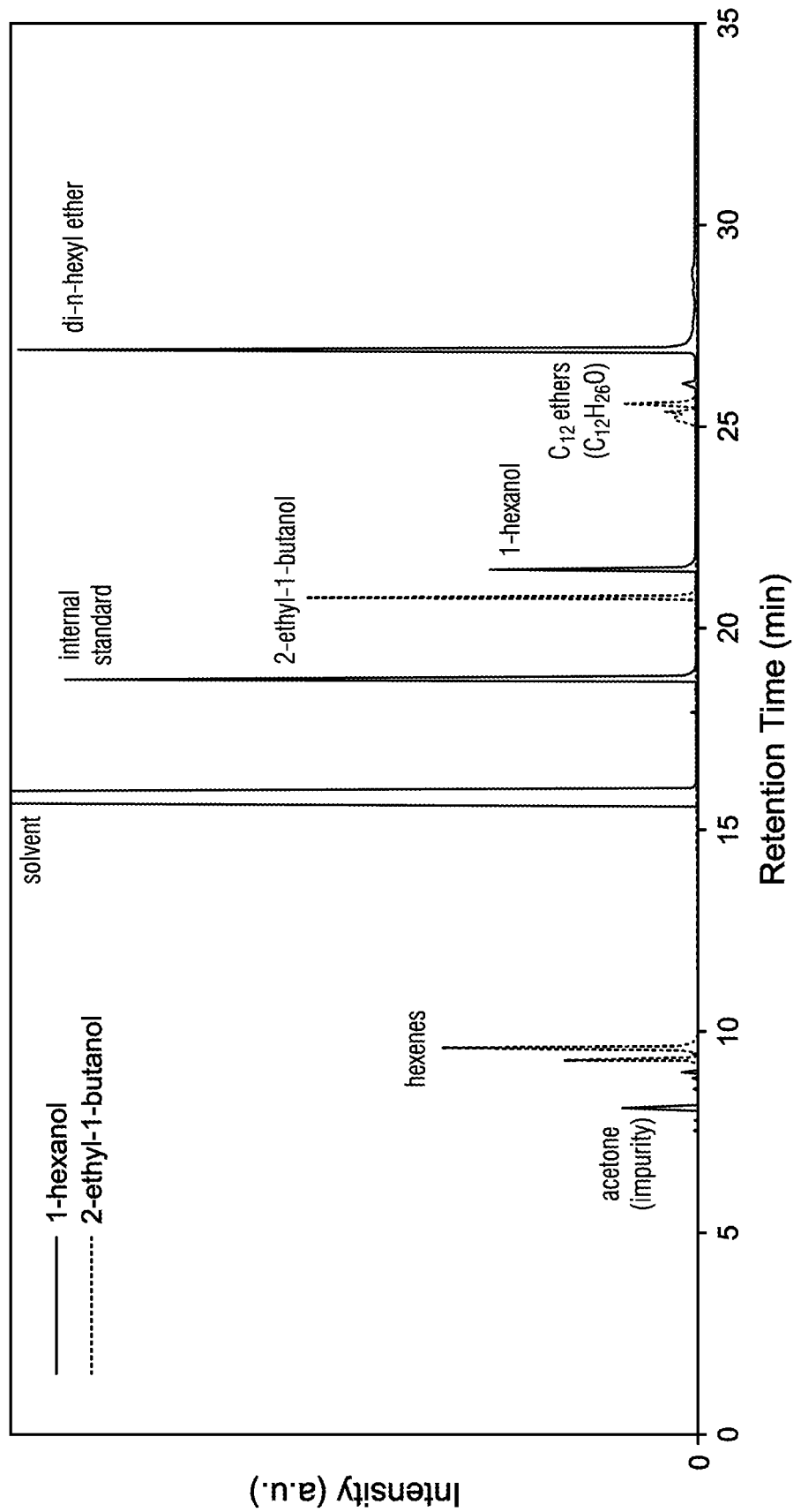
FIG. 19 illustrates the GCs of the dehydration products of 1-hexanol and 1-butyl-2-butanol.

FIG. 19 illustrates the superimposed GCs of the dehydration products of 1-hexanol and 2-ethyl-1-butanol. For 1-hexanol the major product observed was di-n-hexyl ether. For 2-ethyl-1-butanol, the products were hexenes and C12 ethers ($C_{12}H_{26}O$).

Example 10: Dehydration of Mixed Alcohol Feeds

Figure 20:
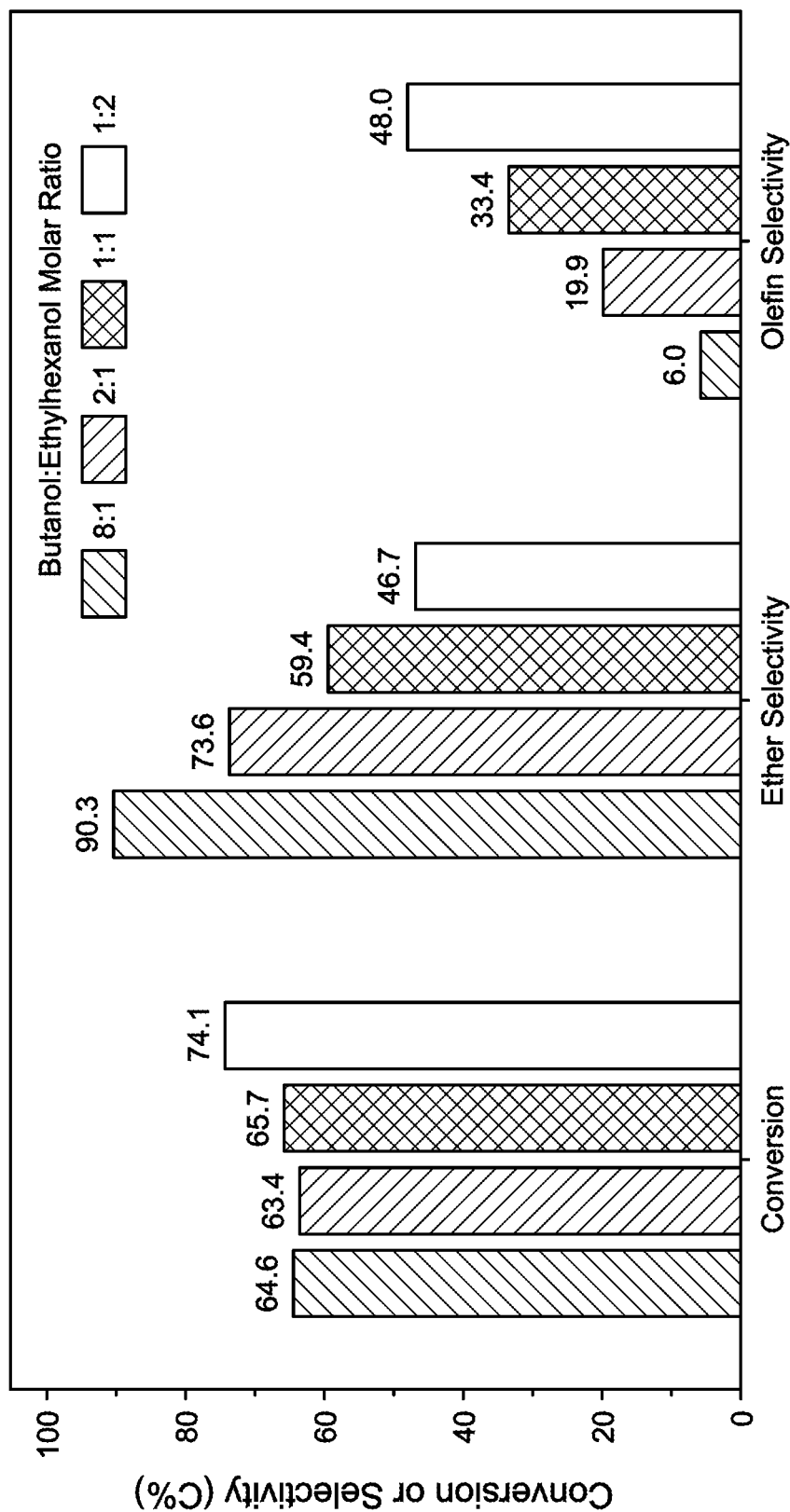
FIG. 20 is a bar chart showing mixed alcohol dehydration conversions and selectivities.

Dehydration of mixed alcohol feeds was undertaken as a model for Guerbet coupled products formed in Example 7. Mixtures of 1-butanol and 2-ethyl-1-hexanol were examined first with molar ratios of 8:1, 2:1, 1:1, and 1:2. FIG. 20 illustrates the conversions and selectivities from these dehydrations.

Feeds with higher 1-butanol contents show higher ether selectivities and lower olefin selectivities. No species other than light olefins and ethers were observed. The conversion of a 1:1 molar ratio of 1-butanol and 2-ethyl-1-hexanol led to an ether selectivity of 59% and an olefin selectivity of 33% at 66% feed conversion. The conversion of 1-butanol was 79% while that of 2-ethyl-1-hexanol was lower at 59%. The cross-etherification product 1-butoxy-2-ethylhexane was positively identified via gas chromatography-mass spectroscopy-electron ionization (GC-MS-EI), clearly showing that cross-etherification occurred between linear and branched alcohols.

Example 11: Dehydration of Mixed Alcohol Feeds

Model alcohol mixtures representative of ethanol coupled products were prepared and subjected to dehydration as per the method of Example 8. The compositions of the feed mixtures are shown in Table 8.

TABLE 8

| Composition | 1 | 2 | 3 | 4 |
|---|---|---|---|---|
| Linear:Branched ratio | 12.5 | 5.3 | 3.2 | 2.0 |
| Composition (mol %) | | | | |
| 1-butanol | 89.8 | 73.3 | 62.7 | 52.3 |
| 1-hexanol | 4.7 | 10.8 | 13.5 | 14.9 |
| 2-ethyl-1-butanol | 4.9 | 12.3 | 16.9 | 21.5 |
| 2-ethyl-1-hexanol | 0.5 | 3.5 | 6.9 | 11.3 |

Figure 21:
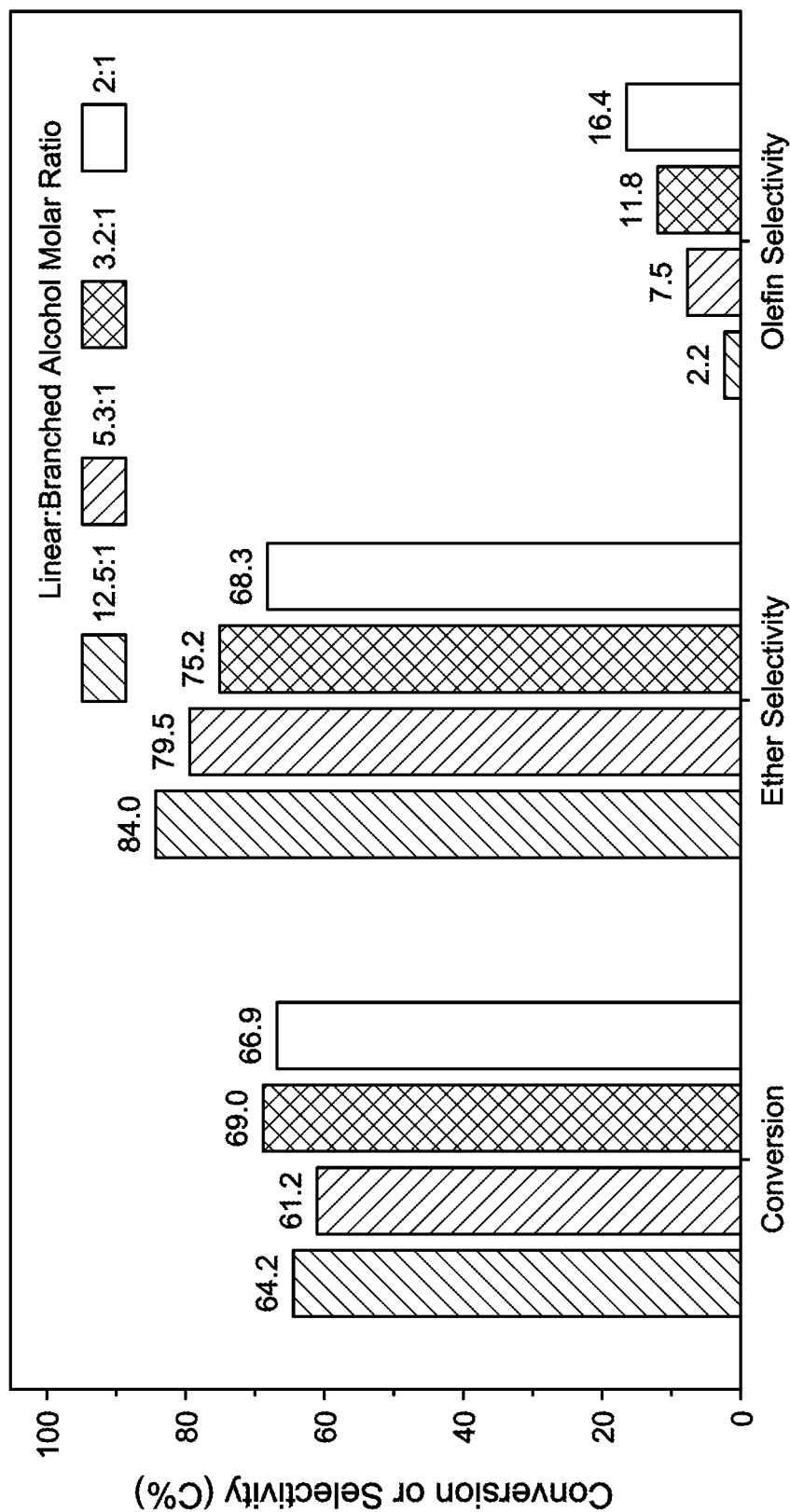
FIG. 21 is a bar chart showing mixed alcohol dehydration conversions and selectivities.

FIG. 21 illustrates the conversions and selectivities from these dehydrations. The mixtures reacted to 65.0-69.5% conversion with ether selectivities ranging from 65.0-81.8%. Cross-etherification was observed between the various alcohols with ethers positively identified based on molecular weight via GC-MS-FI. Approximately 15% of the products couled not be identified. As in the etherification of butanol-ethylhexanol mixtures, ether and olefin selectivities were directly correlated with the linear:branched alcohol feed ratio, though ether selectivities are slightly lower than with the two-component feed. This implies that performing Guerbet condensation at higher conversions where the linear:branched alcohol ratio is lower will result in lower ether selectivities. The olefins were almost entirely 3-methylpentenes and 3-methylheptenes derived from the branched alcohols.

Example 12: Combined Alcohol Coupling and Dehydration

Guerbet coupling was performed in a stainless-steel fixed-bed reactor (40 cm long, 0.95 cm outer diameter) packed with 6.0 g of calcium hydroxyapatite (HAP, Acros Organics) pelletized and sieved to a particle size of 250-354 µm. Prior to reaction, HAP was calcined in 65 mL min$^{-1}$ air at 500° C. (2° C. min$^{-1}$, 2 h hold). Alcohols were fed (10-50 µL min$^{-1}$) with a syringe pump (Teledyne ISCO) concurrently with $H_2$ gas (50-200 mL min-1) at atmospheric pressure in the downflow configuration through a preheated evaporation region maintained at >200° C. prior to entering the reactor. Coupling was carried out at 325° C., 520 s $kg_{HAP}$ mol $_{alcohol}^{-1}$, 8 kPa alcohol, 93 kPa $H_2$.

Ethanol coupling was performed to produce C4+ alcohols. As the water by-product inhibits the following dehydration step it was removed from the product alcohols using molecular sieves. In this way, water concentration was reduced from 15 wt. % to less than 0.5 wt. %. Unreacted ethanol was also removed by distillation. The major components after ethanol removal were 1-butanol (51.8 wt. %), 2-ethyl-1-butanol (13.6 wt. %), 1-hexanol (12.5 wt. %), and 2-ethyl-1-hexanol (4.1 wt. %) with the remainder comprising other alcohols (4.7 wt. %) and species not detected via GC (13.2 wt. %). 79.9 mol. % of the alcohols in the feed were linear.

The mixture of alcohols was subsequently dehydrated over Amberlyst™ 70 to ethers with 73.5% alcohol conversion, 71.6% ether selectivity, and 10.2% olefin selectivity.

CERTAIN EMBODIMENTS

Certain embodiments of processes according to the present disclosure are presented in the following paragraphs.

Embodiment 1 provides a process for producing alcohols from biomass, the process comprising:

(a) contacting biomass and methanol with catalyst (A) in reactor (A) under conditions effective to produce an effluent comprising a mixture of alcohols;

(b) separating the effluent from the reactor (A) into at least two alcohol rich streams and a gas stream comprising carbon monoxide and hydrogen, wherein at least one alcohol rich stream comprises methanol;

(c) recycling at least a portion of the at least one alcohol rich stream comprising methanol to the reactor (A) and/or a feed to reactor (A); and, one or both of steps (d) and (e);

(d) recycling at least a portion of the gas stream comprising carbon monoxide and hydrogen to the reactor (A) and/or a feed to reactor (A);

(e) contacting at least a portion of the gas stream comprising carbon monoxide and hydrogen with catalyst (B) in reactor (B) under conditions effective to produce methanol, and subsequently feeding at least a portion of the so-formed methanol to reactor (A) and/or a feed to reactor (A).

Embodiment 2 provides a process according to embodiment 1, wherein the biomass is dispersed and/or at least partially solubilized in a fluid prior to feeding to reactor (A).

Embodiment 3 provides a process according to embodiment 2, wherein the fluid comprises one or more of methanol, ethanol and an inert fluid, such as a saturated hydrocarbon.

Embodiment 4 provides a process according to any one of embodiments 1 to 3, wherein the biomass and the methanol are separately fed to reactor (A).

Embodiment 5 provides a process according to any one of embodiments 1 to 4, wherein the weight percent biomass in reactor (A) is at least 5 wt. %, or at least 10 wt. %, or at least 15 wt. %, or at least 20 wt. %, based on the total weight of feed components to reactor (A).

Embodiment 6 provides a process according to any one of embodiments 1 to 5, wherein catalyst (A) comprises one or more metals supported on one or more metal oxides.

Embodiment 7 provides a process according to embodiment 6, wherein the one or more metals comprise one or more of Cu, Pd, Pt, Ni and Ru, and the one or more metal oxides comprise one or more of MgO, CaO, SrO, BaO, CeO, $Al_2O_3$, $SiO_2$, $ZrO_2$, and $TiO_2$.

Embodiment 8 provides a process according to embodiment 6, wherein the one or more metals comprise Cu and the metal oxide comprises MgO and $Al_2O_3$.

Embodiment 9 provides a process according to embodiment 7 or embodiment 8, wherein the amount of Cu in catalyst (A) is between 5 wt. % and 30 wt. %, or between 10 wt. % and 20 wt. %, based on the total weight of the catalyst.

Embodiment 10 provides a process according to any one of embodiments 7 to 9, wherein catalyst (A) is reduced prior to use.

Embodiment 11 provides a process according to any one of embodiments 1 to 10, wherein the contacting in step (a) is performed at about 280° C. to about 350° C.

Embodiment 12 provides a process according to any one of embodiments 1 to 11, wherein the pressure in reactor (A) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

Embodiment 13 provides a process according to any one of embodiments 1 to 12, wherein catalyst (B) comprises one or more metals supported on one or more metal oxides.

Embodiment 14 provides a process according to embodiment 13, wherein the one or more metals comprise one or more of Cu, Pd, Pt, Ni and Ru, and the one or more metal oxides comprise one or more of MgO, CaO, ZnO, SrO, BaO, CeO, $Al_2O_3$, $SiO_2$, $ZrO_2$, and $TiO_2$.

Embodiment 15 provides a process according to embodiment 13 or embodiment 14, wherein catalyst (B) comprises Cu supported on a metal oxide comprising ZnO and $Al_2O_3$.

Embodiment 16 provides a process according to embodiment 15, wherein the amount of Cu in catalyst (B) is between 5 wt. % and 30 wt. %, or between 10 wt. % and 20 wt. %, and the amount of Zn in the catalyst is between 2 wt. % and 15 wt. %, or between 5 wt. % and 10 wt. %., based on the total weight of the catalyst.

Embodiment 17 provides a process according to any one of embodiments 13 to 16, wherein catalyst (B) is reduced prior to use.

Embodiment 18 provides a process according to any one of embodiments 1 to 17, wherein the contacting in step (e) is performed at about 280° C. to about 350° C.

Embodiment 19 provides a process according to any one of embodiments 1 to 18, wherein the pressure in reactor (B) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

Embodiment 20 provides a process according to any one of embodiments 1 to 19, wherein prior to step (b), at least a portion of the effluent from reactor (A) is contacted with catalyst (C) in reactor (C) under conditions effective to produce methanol from carbon monoxide and hydrogen.

Embodiment 21 provides a process according to embodiment 20, wherein catalyst (C) comprises one or more metals supported on one or more metal oxides.

Embodiment 22 provides a process according to embodiment 21, wherein the one or more metals comprise one or more of Cu, Pd, Pt, Ni and Ru, and the one or more metal oxides comprise one or more of MgO, CaO, ZnO, SrO, BaO, CeO, $Al_2O_3$, $SiO_2$, $ZrO_2$, and $TiO_2$.

Embodiment 23 provides a process according to embodiment 21 or embodiment 22, wherein the one or more metals comprise Cu and the metal oxides comprises ZnO and $Al_2O_3$.

Embodiment 24 provides a process according to embodiment 23, wherein the amount of Cu in catalyst (C) is between 5 wt. % and 30 wt. %, or between 10 wt. % and 20 wt. %, and the amount of Zn in the catalyst is between 2 wt. % and 15 wt. %, or between 5 wt. % and 10 wt. %., based on the total weight of the catalyst.

Embodiment 25 provides a process according to any one of embodiments 22 to 24, wherein catalyst (C) is reduced prior to use.

Embodiment 26 provides a process according to any one of embodiments 20 to 25, wherein the contacting with catalyst (C) is performed at about 240° C. to about 300° C.

Embodiment 27 provides a process according to any one of embodiments 20 to 26, wherein the pressure in reactor (C) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

Embodiment 28 provides a process according to any one of embodiments 1 to 27, wherein, prior to step (d) or step (e), the gas stream comprising carbon monoxide and hydrogen is treated to remove at least a portion of carbon dioxide.

Embodiment 29 provides a process according to any one of embodiments 1 to 28, further comprising feeding a make-up stream of carbon monoxide and hydrogen to one or both reactor (A) and reactor (B) and/or one or more of a feed to reactor (A) and reactor (B).

Embodiment 30 provides a process according to embodiment 29, wherein at least a portion of the make-up stream of carbon monoxide and hydrogen is derived from the gasification of biomass.

Embodiment 31 provides a process according to embodiment 29 or embodiment 30, wherein the make-up stream of carbon monoxide and hydrogen is rich in hydrogen.

Embodiment 32 provides a process according to embodiment 29 or embodiment 30, wherein the make-up stream of carbon monoxide and hydrogen is rich in carbon monoxide.

Embodiment 33 provides a process according to any one of embodiments 20 to 32, further comprising feeding a make-up stream of carbon monoxide and hydrogen to reactor (C) and/or a feed to reactor (C).

Embodiment 34 provides a process according to embodiment 33, wherein at least a portion of the make-up stream of carbon monoxide and hydrogen is derived from the gasification of biomass.

Embodiment 35 provides a process according to embodiment 33 or embodiment 34, wherein the make-up stream of carbon monoxide and hydrogen is rich in hydrogen.

Embodiment 36 provides a process according to embodiment 33 or embodiment 34, wherein the make-up stream of carbon monoxide and hydrogen is rich in carbon monoxide.

Embodiment 37 provides a process according to any one of embodiments 1 to 36, wherein the alcohol rich stream comprising methanol substantially comprises methanol.

Embodiment 38 provides a process according to any one of embodiments 1 to 36 process according to claim 1, wherein the alcohol rich stream comprising methanol further comprises C2 to C4 alcohols.

Embodiment 39 provides a process according to any one of embodiments 1 to 38, wherein in step (b) the mixture of alcohols is separated into three or more alcohol rich streams.

Embodiment 40 provides a process according to any one of embodiments 1 to 39, wherein the alcohol rich stream comprising methanol is first contacted with biomass, to solubilize at least some of the biomass, prior to feeding the resulting mixture to reactor (A).

Embodiment 41 provides a process according to any one of embodiments 1 to 40, wherein biomass and methanol are fed to reactor (A) after a period of time during which only carbon monoxide and hydrogen are fed to reactor (A), wherein during said period of time the carbon monoxide and hydrogen produce methanol.

Embodiment 42 provides a process according to any one of embodiments 1 to 41, further comprising the step of recycling at least part of the effluent from reactor (A) back to reactor (A).

Embodiment 43 provides a process according to any one of embodiments 1 to 42, wherein the biomass comprises one or more of agricultural residues, energy crops, wood, wood wastes, food waste, municipal solid waste, cellulose, sugar cane bagasse, corn stover, and chitin.

Embodiment 44 provides a process according to any one of embodiments 1 to 43, wherein the selectivity to monoalcohols in the effluent from reactor (A) is at least about 30%.

Embodiment 45 provides a process according to any one of embodiments 20 to 44, wherein the selectivity to monoalcohols in an effluent from reactor (C) is at least about 30%.

Embodiment 46 provides a process according to any one of embodiments 1 to 45, wherein the weight percent biomass in reactor (A) is at least 10 wt. % based on the total weight of feed components to reactor (A) and the selectivity to mono-alcohols in the effluent from reactor (A) is at least about 30%.

Embodiment 47 provides a process for producing alcohols from biomass, the process comprising:

(a) contacting biomass and methanol with catalyst (A) in reactor (A) under conditions effective to produce a mixture of alcohols;

(b) contacting effluent from reactor (A) with catalyst (C) in reactor (C) under conditions effective to produce methanol from carbon monoxide and hydrogen;

(c) separating effluent from reactor (C) into at least two alcohol rich streams and a gas stream comprising carbon monoxide and hydrogen, wherein at least one alcohol rich stream comprises methanol;

(d) recycling at least a portion of the at least one alcohol rich stream comprising methanol to reactor (A) and/or a feed to reactor (A); and, one or both of steps (e) and (f);

(e) recycling at least a portion of the gas stream comprising carbon monoxide and hydrogen to reactor (C); and (f) contacting at least a portion of the gas stream comprising carbon monoxide and hydrogen with catalyst (B) in reactor (B) under conditions effective to produce methanol and subsequently feeding at least a portion of the so-formed methanol to reactor (A) and/or a feed to reactor (A).

Embodiment 48 provides a process according to embodiment 47, wherein the biomass is dispersed and/or at least partially solubilized in a fluid prior to feeding to reactor (A).

Embodiment 49 provides a process according to embodiment 48, wherein the fluid comprises one or more of methanol, ethanol and an inert fluid, such as a saturated hydrocarbon.

Embodiment 50 provides a process according to embodiment 47, wherein the biomass and the methanol are separately fed to reactor (A).

Embodiment 51 provides a process according to any one of embodiments 47 to 50, wherein the weight percent biomass in reactor (A) is at least 5 wt. %, or at least 10 wt. %, or at least 15 wt. %, or at least 20 wt. %, based on the total weight of feed components to reactor (A).

Embodiment 52 provides a process according to any one of embodiments 47 to 51, wherein catalyst (A) comprises one or more metals supported on one or more metal oxides.

Embodiment 53 provides a process according to embodiment 52, wherein the one or more metals comprise one or more of Cu, Pd, Pt, Ni and Ru, and the metal oxide comprises one or more of MgO, CaO, SrO, BaO, CeO, $Al_2O_3$, $SiO_2$, $ZrO_2$, and $TiO_2$.

Embodiment 54 provides a process according to embodiment 52, wherein the one or more metals comprise Cu and the one or more metal oxides comprise MgO and $Al_2O_3$.

Embodiment 55 provides a process according to embodiment 53 or embodiment 54, wherein the amount of Cu in the catalyst is between 5 wt. % and 30 wt. %, or between 10 wt. % and 20 wt. %, based on the total weight of the catalyst.

Embodiment 56 provides a process according to any one of embodiments 52 to 55, wherein catalyst (A) is reduced prior to use.

Embodiment 57 provides a process according to any one of embodiments 47 to 56, wherein the contacting in step (a) is performed at about 280° C. to about 350° C.

Embodiment 58 provides a process according to any one of embodiments 47 to 57, wherein the pressure in reactor (A) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

Embodiment 59 provides a process according to any one of embodiments 47 to 58, wherein catalyst (C) comprises one or more metals supported on one or more metal oxides.

Embodiment 60 provides a process according to embodiment 59, wherein the one or more metals comprises one or more of Cu, Pd, Pt, Ni and Ru, and the one or more metal oxides comprise one or more of MgO, CaO, ZnO, SrO, BaO, CeO, $Al_2O_3$, $SiO_2$, $ZrO_2$, and $TiO_2$.

Embodiment 61 provides a process according to embodiment 59 or embodiment 60, wherein the one or more metals comprise Cu and the one or more metal oxides comprise ZnO and $Al_2O_3$.

Embodiment 62 provides a process according to embodiment 61, wherein the amount of Cu in catalyst (C) is between 5 wt. % and 30 wt. %, or between 10 wt. % and 20 wt. %, and the amount of Zn in the catalyst is between 2 wt. % and 15 wt. %, or between 5 wt. % and 10 wt. %., based on the total weight of the catalyst.

Embodiment 63 provides a process according to any one of embodiments 59 to 62, wherein catalyst (C) is reduced prior to use.

Embodiment 64 provides a process according to any one of embodiments 47 to 63, wherein the temperature in reactor (C) is lower than the temperature in reactor (A).

Embodiment 65 provides a process according to any one of embodiments 47 to 64, wherein the contacting with catalyst (C) is performed at about 240° C. to about 300° C.

Embodiment 66 provides a process according to any one of embodiments 47 to 65, wherein the pressure in reactor (C) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

Embodiment 67 provides a process according to any one of embodiments 47 to 66, wherein catalyst (B) comprises one or more metals supported on one or more metal oxides.

Embodiment 68 provides a process according to any one of embodiments 47 to 67, wherein the one or more metals comprise one or more of Cu, Pd, Pt, Ni and Ru, and the one or more metal oxides comprise one or more of MgO, CaO, ZnO, SrO, BaO, CeO, $Al_2O_3$, $SiO_2$, $ZrO_2$, and $TiO_2$.

Embodiment 69 provides a process according to embodiment 67 or embodiment 68, wherein catalyst (B) comprises Cu supported on a metal oxide comprising ZnO and $Al_2O_3$.

Embodiment 70 provides a process according to embodiment 69, wherein the amount of Cu in catalyst (B) is between 5 wt. % and 30 wt. %, or between 10 wt. % and 20 wt. %, and the amount of Zn in the catalyst is between 2 wt. % and 15 wt. %, or between 5 wt. % and 10 wt. %., based on the total weight of the catalyst.

Embodiment 71 provides a process according to any one of embodiments 68 to 70, wherein catalyst (B) is reduced prior to use.

Embodiment 72 provides a process according to any one of embodiments 47 to 71, wherein the contacting in step (e) is performed at about 280° C. to about 350° C.

Embodiment 73 provides a process according to any one of embodiments 47 to 72, wherein the pressure in reactor (B) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

Embodiment 74 provides a process according to any one of embodiments 47 to 73, wherein, prior to step (e), the gas stream comprising carbon monoxide and hydrogen is treated to remove at least a portion of carbon dioxide.

Embodiment 75 provides a process according to any one of embodiments 47 to 74, further comprising feeding a make-up stream of carbon monoxide and hydrogen to one or more of reactor (A), reactor (B) and reactor (C) and/or one or more of a feed to reactor (A), reactor (B) and reactor (C).

Embodiment 76 provides a process according to embodiment 75, wherein at least a portion of the make-up stream of carbon monoxide and hydrogen is derived from the gasification of biomass.

Embodiment 77 provides a process according to embodiment 75 or embodiment 76, wherein the make-up stream of carbon monoxide and hydrogen is rich in hydrogen.

Embodiment 78 provides a process according to embodiment 75 or embodiment 76, wherein the make-up stream of carbon monoxide and hydrogen is rich in carbon monoxide.

Embodiment 79 provides a process according to any one of embodiments 47 to 78, wherein the alcohol rich stream comprising methanol substantially comprises methanol.

Embodiment 80 provides a process according to any one of embodiments 47 to 79, wherein the alcohol rich stream comprising methanol further comprises C2 to C4 alcohols.

Embodiment 81 provides a process according to any one of embodiments 47 to 80, wherein in step (c) the mixture of alcohols is separated into three or more alcohol rich streams.

Embodiment 82 provides a process according to any one of embodiments 47 to 81, wherein the alcohol rich stream comprising methanol is first contacted with biomass, to solubilize at least some of the biomass, prior to feeding the resulting mixture to reactor (A).

Embodiment 83 provides a process according to any one of embodiments 47 to 82, wherein the biomass and methanol are fed to reactor (A) after a period of time during which only carbon monoxide and hydrogen are fed to reactor (A), wherein during said period of time carbon monoxide and hydrogen produce methanol.

Embodiment 84 provides a process according to any one of embodiments 47 to 83, further comprising the step of recycling at least part of the effluent from one or both reactor (A) and reactor (C) back to reactor (A).

Embodiment 85 provides a process according to any one of embodiments 47 to 84, wherein the biomass comprises one or more of agricultural residues, energy crops, wood, wood wastes, food waste, municipal solid waste, cellulose, sugar cane bagasse, corn stover, and chitin.

Embodiment 86 provides a process according to any one of embodiments 47 to 85, wherein the selectivity to mono-alcohols in the effluent from reactor (A) is at least about 30%.

Embodiment 87 provides a process according to any one of embodiments 47 to 86, wherein the selectivity to mono-alcohols in the effluent from reactor (C) is at least about 30%.

Embodiment 88 provides a process according to any one of embodiments 47 to 87, wherein the weight percent biomass in reactor (A) is at least 10 wt. % based on the total weight of feed components to reactor (A) and the selectivity to mono-alcohols in the effluent from reactor (A) is at least about 30%.

Certain embodiments of processes according to the present disclosure are presented in the following paragraphs.

Embodiment 1 provides a process for producing ethers and olefins from biomass, the process comprising:
a) contacting biomass and methanol with catalyst (A) in reactor (A) under conditions effective to produce a first effluent comprising a mixture of alcohols;
b) contacting at least a portion of the first effluent comprising a mixture of alcohols with catalyst (D) in reactor (D) under conditions effective to produce a second effluent comprising higher alcohols; and
c) contacting at least a portion of the second effluent comprising higher alcohols with catalyst (E) in reactor (E) under conditions effective to dehydrate at least a portion of the higher alcohols to ethers and olefins.

Embodiment 2 provides a process according to embodiment 1, wherein the biomass is dispersed and/or at least partially solubilized in a fluid prior to feeding to reactor (A).

Embodiment 3 provides a process according to embodiment 2, wherein the fluid comprises one or more of methanol, ethanol and an inert fluid, such as a saturated hydrocarbon.

Embodiment 4 provides a process according to any one of embodiments 1 to 3, wherein the biomass and the methanol are separately fed to reactor (A).

Embodiment 5 provides a process according to any one of embodiments 1 to 4, wherein the weight percent biomass in reactor (A) is at least 5 wt. %, or at least 10 wt. %, or at least 15 wt. %, or at least 20 wt. %, based on the total weight of feed components to reactor (A).

Embodiment 6 provides a process according to any one of embodiments 1 to 5, wherein catalyst (A) comprises one or more metals supported on one or more metal oxides.

Embodiment 7 provides a process according to embodiment 6, wherein the one or more metals comprise one or more of Cu, Pd, Pt, Ni and Ru, and the one or more metal oxides comprise one or more of MgO, CaO, SrO, BaO, CeO, $Al_2O_3$, $SiO_2$, $ZrO_2$, and $TiO_2$.

Embodiment 8 provides a process according to embodiment 6, wherein the one or more metals comprise Cu and the metal oxide comprises MgO and $Al_2O_3$.

Embodiment 9 provides a process according to embodiment 7 or embodiment 8, wherein the amount of Cu in catalyst (A) is between 5 wt. % and 30 wt. %, or between 10 wt. % and 20 wt. %, based on the total weight of the catalyst.

Embodiment 10 provides a process according to any one of embodiments 7 to 9, wherein catalyst (A) is reduced prior to use.

Embodiment 11 provides a process according to any one of embodiments 1 to 10, wherein the contacting in step (a) is performed at about 280° C. to about 350° C.

Embodiment 12 provides a process according to any one of embodiments 1 to 11, wherein the pressure in reactor (A) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

Embodiment 13 provides a process according to any one of embodiments 1 to 12 further comprising:
(i) separating the effluent from reactor (A) into at least two alcohol rich streams and a gas stream comprising carbon monoxide and hydrogen, wherein at least one alcohol rich stream comprises methanol; and recycling at least a portion of the at least one alcohol rich stream comprising methanol to reactor (A) and/or a feed to reactor (A).

Embodiment 14 provides a process according to any one of embodiments 1 to 13, further comprising one or both of the following (i) and (ii):
(i) recycling at least a portion of the gas stream comprising carbon monoxide and hydrogen to reactor (A) and/or a feed to reactor (A);
(ii) contacting at least a portion of the gas stream comprising carbon monoxide and hydrogen with catalyst (B) in reactor (B) under conditions effective to produce methanol, and subsequently feeding at least a portion of the so-formed methanol to reactor (A) and/or a feed to reactor (A).

Embodiment 15 provides a process according to embodiment 14, wherein catalyst (B) comprises one or more metals supported on one or more metal oxides.

Embodiment 16 provides a process according to embodiment 15, wherein the one or more metals comprise one or more of Cu, Pd, Pt, Ni and Ru, and the one or more metal oxides comprise one or more of MgO, CaO, ZnO, SrO, BaO, CeO, $Al_2O_3$, $SiO_2$, $ZrO_2$, and $TiO_2$.

Embodiment 17 provides a process according to embodiment 15 or embodiment 16, wherein catalyst (B) comprises Cu supported on a metal oxide comprising ZnO and $Al_2O_3$.

Embodiment 18 provides a process according to embodiment 17, wherein the amount of Cu in catalyst (B) is between 5 wt. % and 30 wt. %, or between 10 wt. % and 20 wt. %, and the amount of Zn in the catalyst is between 2 wt. % and 15 wt. %, or between 5 wt. % and 10 wt. %., based on the total weight of the catalyst.

Embodiment 19 provides a process according to any one of embodiments 15 to 18, wherein catalyst (B) is reduced prior to use.

Embodiment 20 provides a process according to any one of embodiments 14 to 19, wherein the contacting in step (ii) is performed at about 280° C. to about 350° C.

Embodiment 21 provides a process according to any one of embodiments 14 to 20, wherein the pressure in reactor (B) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

Embodiment 22 provides a process according to any one of embodiments 1 to 21, wherein, prior to step (b), at least a portion of the effluent from reactor (A) is contacted with catalyst (C) in reactor (C) under conditions effective to produce methanol from carbon monoxide and hydrogen.

Embodiment 23 provides a process according to embodiment 22, wherein catalyst (C) comprises one or more metals supported on one or more metal oxides.

Embodiment 24 provides a process according to embodiment 23, wherein the one or more metals comprise one or more of Cu, Pd, Pt, Ni and Ru, and the one or more metal oxides comprise one or more of MgO, CaO, ZnO, SrO, BaO, CeO, $Al_2O_3$, $SiO_2$, $ZrO_2$, and $TiO_2$.

Embodiment 25 provides a process according to embodiment 23 or embodiment 24, wherein the one or more metals comprise Cu and the metal oxides comprises ZnO and $Al_2O_3$.

Embodiment 26 provides a process according to embodiment 25, wherein the amount of Cu in catalyst (C) is between 5 wt. % and 30 wt. %, or between 10 wt. % and 20 wt. %, and the amount of Zn in the catalyst is between 2 wt. % and 15 wt. %, or between 5 wt. % and 10 wt. %., based on the total weight of the catalyst.

Embodiment 27 provides a process according to any one of embodiments 23 to 26, wherein catalyst (C) is reduced prior to use.

Embodiment 28 provides a process according to any one of embodiments 22 to 27, wherein the contacting with catalyst (C) is performed at about 240° C. to about 300° C.

Embodiment 29 provides a process according to any one of embodiments 22 to 28, wherein the pressure in reactor (C) is between about 1000 psi (6.9 MPa) and about 4000 psi (27.6 MPa), or between about 1000 psi (6.9 MPa) and about 3500 psi (24.1 MPa), or between about 1000 psi (6.9 MPa) and about 3000 psi (20.6 MPa), or between about 1000 psi (6.9 MPa) and about 2500 psi (17.2 MPa), or between about 1000 psi (6.9 MPa) and about 2000 psi (13.8 MPa), or between about 1000 psi (6.9 MPa) and about 1500 psi (10.3 MPa).

Embodiment 30 provides a process according to any one of embodiments 1 to 29 wherein, prior to step (a) or step (b), the gas stream comprising carbon monoxide and hydrogen is treated to remove at least a portion of carbon dioxide.

Embodiment 31 provides a process according to any one of embodiments 1 to 30, wherein the process further comprises feeding a make-up stream of carbon monoxide and hydrogen to reactor (A) and/or to any one or more of the feeds to reactor (A).

Embodiment 32 provides a process according to any one of embodiments 14 to 31, wherein the process further comprises feeding a make-up stream of carbon monoxide and hydrogen to reactor (B) and/or to any one or more of the feeds to reactor (B).

Embodiment 33 provides a process according to any one of embodiments 22 to 32, wherein the process further comprises feeding a make-up stream of carbon monoxide and hydrogen to reactor (C) and/or to any one or more of the feeds to reactor (C).

Embodiment 34 provides a process according to any one of embodiments 31 to 33, wherein at least a portion of the make-up stream of carbon monoxide and hydrogen is derived from the gasification of biomass.

Embodiment 35 provides a process according to any one of embodiments 31 to 34, wherein the make-up stream of carbon monoxide and hydrogen is rich in hydrogen.

Embodiment 36 provides a process according to any one of embodiments 31 to 34, wherein the make-up stream of carbon monoxide and hydrogen is rich in carbon monoxide.

Embodiment 37 provides a process according to any one of embodiments 13 to 36, wherein the alcohol rich stream comprising methanol substantially comprises methanol.

Embodiment 38 provides a process according to any one of embodiments 13 to 36, wherein, the alcohol rich stream comprising methanol further comprises C2 to C4 alcohols.

Embodiment 39 provides a process according to any one of embodiments 1 to 38, wherein, the mixture of alcohols from step (a) is separated into three or more alcohol rich streams.

Embodiment 40 provides a process according to embodiment 37, wherein, the alcohol rich stream comprising methanol is first contacted with biomass, to solubilize at least a portion of the biomass, prior to feeding the resulting mixture to reactor (A).

Embodiment 41 provides a process according to any one of embodiments 1 to 40, wherein, biomass and methanol are fed to reactor (A) after a period of time during which only carbon monoxide and hydrogen are fed to reactor (A), wherein during said period of time the carbon monoxide and hydrogen produce methanol.

Embodiment 42 provides a process according to any one of embodiments 1 to 41, wherein the process further comprises the step of recycling at least a portion of the effluent from reactor (A) back to reactor (A).

Embodiment 43 provides a process according to any one of embodiments 1 to 42, wherein the biomass comprises one or more of agricultural residues, energy crops, wood, wood wastes, food waste, municipal solid waste, cellulose, sugar cane bagasse, corn stover, and chitin.

Embodiment 44 provides a process according to any one of embodiments 1 to 43, wherein the selectivity to mono-alcohols in the effluent from reactor (A) is at least about 30%.

Embodiment 45 provides a process according to any one of embodiments 22 to 44, wherein the selectivity to mono-alcohols in an effluent from reactor (C) is at least about 30%.

Embodiment 46 provides a process according to any one of embodiments 1 to 45, wherein the weight percent biomass in reactor (A) is at least 10 wt. % based on the total weight of feed components to reactor (A) and the selectivity to mono-alcohols in the effluent from reactor (A) is at least about 30%.

Embodiment 47 provides a process according to any one of embodiments 1 to 46, wherein at least a portion of the mixture of alcohols contacted with catalyst (D) in step (b) comprise primary alcohols.

Embodiment 48 provides a process according to embodiment 47, wherein the primary alcohols comprise one or more C2 to C5 alcohols.

Embodiment 49 provides a process according to embodiment 47, wherein the primary alcohols comprise one or more of ethanol and 1-butanol.

Embodiment 50 provides a process according to any one of embodiments 1 to 49, wherein the contacting in step (b) is performed in the presence of one or more of hydrogen and inert gas.

Embodiment 51 provides a process according to any one of embodiments 1 to 50, wherein, the higher alcohols produced in step (b) comprise one or more C4+ alcohols.

Embodiment 52 provides a process according to any one of embodiments 1 to 51, wherein step (b) is performed at a temperature from about 250° C. to about 370° C., preferably from about 280° C. to about 350° C.

Embodiment 53 provides a process according to any one of embodiments 1 to 52, wherein step (b) is performed at a pressure from about 15 psi (0.1 MPa) to about 1000 psi (6.9 MPa), or from about 100 psi (0.69 MPa) to about 1000 psi (6.9 MPa), or from about 200 psi (1.38 MPa) to about 500 psi (3.45 MPa).

Embodiment 54 provides a process according to any one of embodiments 1 to 53, wherein, in step (b), the partial pressure of hydrogen is less than 100 psi (0.69 MPa), or less than 90 psi (0.62 MPa), or less than 80 psi (0.55 MPa) or less than 70 psi (0.48 MPa), or less than 60 psi (0.41 MPa).

Embodiment 55 provides a process according to any one of embodiments 1 to 54, wherein catalyst (D) is a heterogeneous catalyst comprising one or more Group A oxides, said Group A oxides being oxides of Mg, Ca, Zn, Mn, Sr, Si and Zr; one or more Group B oxides, said Group B oxides being one or more oxides of Al, La, Ga, Ce, Fe, Sc, Cr, P and V; and combinations of both Group A and Group B oxides, and, optionally, one or more of Cu, Ni, Pt, Pd, Rh, Co, Cs and Rb.

Embodiment 56 provides a process according to any one of embodiments 1 to 54, wherein catalyst (D) is a heterogeneous catalyst comprising one or more oxides of Mg, Ca, Zn, Sr, Al and Ce.

Embodiment 57 provides a process according to any one of embodiments 1 to 54, wherein catalyst (D) is a heterogeneous catalyst comprising one or more oxides of Mg, Ca and Zn, one or more oxides of Al, La, Ga, Ce, Fe and Cr, and one or more of Cu, Ni, Pt, Pd, Rh and Co.

Embodiment 58 provides a process according to any one of embodiments 1 to 54, wherein catalyst (D) is a heterogeneous catalyst comprising one or more oxides of Mg, Ca and Sr, one or more of P and V, and, optionally, one or more of Cu, Ni, Pt, Pd, Rh, and Co.

Embodiment 59 provides a process according to any one of embodiments 1 to 54, wherein catalyst (D) is a heterogeneous catalyst comprising Al and Si metal oxides and one or more of Cs and Rb.

Embodiment 60 provides a process according to any one of embodiments 55 to 58, wherein the weight percent of the one or more of Cu, Ni, Pt, Pd, Rh and Co in catalyst (D) is up to about 10 wt. %, or from about 0.01 wt. % to about 9 wt. %, or from about 0.01 wt. % to about 8 wt. %, or from about 0.01 wt. % to about 7 wt. %, or from about 0.01 wt. % to about 6 wt. %, or from about 0.01 wt. % to about 5 wt. %, or from about 0.01 wt. % to about 4 wt. %, or from about 0.01 wt. % to about 3 wt. %, or from about 0.01 wt. % to about 2 wt. %, or from about 0.01 wt. % to about 1 wt. %, or from about 0.01 wt. % to about 0.5 wt. %, or from about 0.01 wt. % to about 0.4 wt. %, or from about 0.01 wt. % to about 0.3 wt. %, or from about 0.01 wt. % to about 0.2 wt. %, or from about 0.01 wt. % to about 0.1 wt. %, based on the total weight of the catalyst.

Embodiment 61 provides a process according to any one of embodiments 55 to 57 or 60, wherein catalyst (D) comprises Mg and Al oxides and Cu and the weight percent of Cu is preferably 0.05 wt. % to 1.0 wt. %, or 0.05 wt. % to 0.5 wt. %, or 0.05 wt. % to 0.2 wt. %, based on the total weight of the catalyst.

Embodiment 62 provides a process according to any one of embodiments 55 to 61, wherein catalyst (D) is reduced prior to use.

Embodiment 63 provides a process according to any one of embodiments 1 to 62, wherein the selectivity to alcohols in step (b) is at least about 45%, or at least about 50%, or at least about 55%, or at least about 60%, or at least about 65%, or at least about 70%, or at least about 75%, or at least about 80%.

Embodiment 64 provides a process according to any one of embodiments 1 to 63, wherein the selectivity to primary linear alcohols in step (b), based on total alcohols formed, is at least about 80%, or at least about 85%, or at least about 90%, or at least about 95%, or at least about 96%, or at least about 97%, or at least about 98%, or at least about 99%.

Embodiment 65 provides a process according to any one of embodiments 1 to 64, wherein the selectivity to primary branched alcohols in step (b), based on total alcohols formed, is less than about 20%, or less than about 15%, or less than about 10%, or less than about 5%, or less than about 4%, or less than about 3%, or less than about 2%, or less than about 1%.

Embodiment 66 provides a process according to any one of embodiments 1 to 65, wherein the effluent from step (b) further comprises one or more olefins.

Embodiment 67 provides a process according to embodiment 66, wherein the selectivity to olefins in step (b) is less than about 20%, or less than about 15%, or less than about 10%, or less than about 5%.

Embodiment 68 provides a process according to any one of embodiments 1 to 67, wherein the effluent from step (b) further comprises one or more esters.

Embodiment 69 provides a process according to embodiment 68, wherein the selectivity to esters in step (b) is less than about 30%, or less than about 25%, or less than about 20%, or less than about 15%, or less than about 10%, or less than about 5%.

Embodiment 70 provides a process according to any one of embodiments 1 to 69, wherein the effluent from step (b) further comprises one or more ethers.

Embodiment 71 provides a process according to embodiment 70, wherein the selectivity to ethers in step (b) is less than about 20%, or less than about 15%, or less than about 10%, or less than about 5%.

Embodiment 72 provides a process according to any one of embodiments 1 to 71, wherein the effluent from step (b) further comprises one or more aldehydes and/or ketones.

Embodiment 73 provides a process according to embodiment 72, wherein the selectivity to aldehydes and ketones in step (b) is less than about 20%, or less than about 15%, or less than about 10%, or less than about 5%.

Embodiment 74 provides a process according to any one of embodiments 1 to 73, wherein step (c) is performed at a temperature from about 100° C. to about 180° C.

Embodiment 75 provides a process according to any one of embodiments 1 to 74, wherein catalyst (E) is a solid acid catalyst comprising one or more of acidic resins, alumina and aluminosilicates, heteropoly acids, and tungsten and molybdenum functionalized oxides.

Embodiment 76 provides a process according to any one of embodiments 1 to 75, wherein the ethers produced in step (c) comprise one or more C8-C24 ethers.

Embodiment 77 provides a process according to any one of embodiments 1 to 76, wherein the olefins produced in step (c) comprise one or more C6-C14 olefins.

Embodiment 78 provides a process according to any one of embodiments 1 to 77, wherein the process further comprises:

(i) separating the effluent from step (b) into a first stream rich in olefins and one or more second streams rich in alcohols, wherein the one or more second streams rich in alcohols comprise a first stream rich in C2-C4 alcohols and a second stream rich in C4+ alcohols; and (ii) recycling at least a portion of the first stream rich in C2-C4 alcohols to step (b).

Embodiment 79 provides a process according to embodiment 78, wherein the process further comprises:

(iii) contacting at least a portion of the second stream rich in C4+ alcohols with catalyst (E) in reactor (E) under conditions effective to dehydrate at least a portion of the C4+ alcohols to ethers and olefins; and (iv) separating the ethers and olefins produced in step (iii) into a second stream rich in olefins, a stream rich in ethers, and a stream rich in alcohols.

Embodiment 80 provides a process according to embodiment 79, wherein the process further comprises the step of combining at least a portion of the first stream rich in olefins produced in step (i) of embodiment 78 with at least a portion of the second stream rich in olefins produced in step (iv) of embodiment 79.

Embodiment 81 provides a process according to any one of embodiments 78 to 80, wherein the first stream rich in olefins produced in step (i) comprises C2-C4 olefins.

Embodiment 82 provides a process according to any one of embodiments 78 to 81, wherein the process further comprises the step of recycling at least a portion of the stream rich in alcohols produced in step (iv) to step (iii).

Embodiment 83 provides a process according to any one of embodiments 79 to 82, wherein the stream rich in ethers produced in step (iv) comprises one or more C8-C16+ ethers.

Embodiment 84 provides a process according to any one of embodiments 79 to 83, wherein the second stream rich in olefins produced in step (iv) comprises one or more C6+ olefins.

Embodiment 85 provides a process according to any one of embodiments 78 to 84, wherein at least a portion of any one or more of the first stream rich in olefins, the second stream rich in olefins, and the combined streams of olefins, are oligomerized to higher olefins in the presence of a catalyst comprising acidic sites.

Embodiment 86 provides a process according to embodiment 85, wherein the catalyst comprising acid sites further comprises one or more transition metals, for example cobalt and/or nickel.

Embodiment 87 provides a process according to embodiment 85 or embodiment 86, wherein the higher olefins comprise C8-C16+ olefins.

Embodiment 88 provides a process according to any one of embodiments 85 to 87, wherein at least a portion of the higher olefins is hydrotreated in the presence of a transition metal catalyst to paraffins.

Embodiment 89 provides a process according to embodiment 88, wherein the paraffins comprise C8-C16+ paraffins.

The contents of all references and published patents and patent applications cited throughout the application are hereby incorporated by reference.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the reactants may be varied to optimize the desired effects, additional reactants may be added, and/or similar reactants may be substituted for one or more of the reactants described. Additional advantageous features and functionalities associated with the processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims

The invention claimed is:

1. A process for producing alcohols from biomass, the process comprising:
(a) contacting biomass and methanol with catalyst (A) in reactor (A) under conditions effective to produce an effluent comprising a mixture of alcohols;
(b) separating the effluent from the reactor (A) into at least two alcohol rich streams and a gas stream comprising carbon monoxide and hydrogen, wherein at least one alcohol rich stream comprises methanol;
(c) recycling at least a portion of the at least one alcohol rich stream comprising methanol to the reactor (A) and/or a feed to reactor (A); and, one or both of steps (d) and (e);
(d) recycling at least a first portion of the gas stream comprising carbon monoxide and hydrogen to the reactor (A) and/or a feed to reactor (A);
(e) contacting at least a second portion of the gas stream comprising carbon monoxide and hydrogen with catalyst (B) in reactor (B) under conditions effective to produce a methanol-containing product, and subsequently feeding at least a portion of the methanol-containing product to reactor (A) and/or a feed to reactor (A),
wherein, prior to step (d) or step (e), the at least a first portion of the gas stream comprising carbon monoxide and hydrogen, the at least a second portion of the gas stream comprising carbon monoxide and hydrogen, or a combination thereof, is treated to remove at least a portion of carbon dioxide.

2. The process of claim 1, wherein the biomass is dispersed and/or at least partially solubilized in a fluid prior to feeding to reactor (A).

3. The process of claim 2, wherein the fluid comprises one or more of methanol, ethanol and an inert fluid.

4. The process of claim 1, wherein the biomass and the methanol are separately fed to reactor (A).

5. The process of claim 1, wherein the weight percent biomass in reactor (A) is at least 10 wt. %, based on the total weight of feed components to reactor (A).

6. The process of claim 1, wherein catalyst (A) comprises one or more metals supported on one or more metal oxides.

7. The process of claim 6, wherein the one or more metals comprise one or more of Cu, Pd, Pt, Ni and Ru, and the one or more metal oxides comprise one or more of MgO, CaO, SrO, BaO, CeO, $Al_2O_3$, $SiO_2$, $ZrO_2$, and $TiO_2$.

8. The process of claim 7, wherein the one or more metals comprise Cu and the metal oxide comprises MgO and $Al_2O_3$.

9. The process of claim 7, wherein the amount of Cu in catalyst (A) is between 5 wt. % and 30 wt. %, based on the total weight of the catalyst.

10. The process of claim 6, wherein catalyst (A) is reduced prior to use.

11. The process of claim 1, wherein the contacting in step (a) is performed at about 280° C. to about 350° C.

12. The process of claim 1, wherein the pressure in reactor (A) is between about 1000 psi (6.9 MPa) and about 4000 psi (27.6 MPa).

13. The process of claim 1, wherein catalyst (B) comprises one or more metals supported on one or more metal oxides.

14. The process of claim 13, wherein the one or more metals comprise one or more of Cu, Pd, Pt, Ni and Ru, and the one or more metal oxides comprise one or more of MgO, CaO, ZnO, SrO, BaO, CeO, $Al_2O_3$, $SiO_2$, $ZrO_2$, and $TiO_2$.

15. The process of claim 14, wherein catalyst (B) comprises Cu supported on a metal oxide comprising ZnO and $Al_2O_3$.

16. The process of claim 15, wherein the amount of Cu in the catalyst is between 5 wt. % and 30 wt. %, and the amount of Zn in the catalyst is between 2 wt. % and 15 wt. %, based on the total weight of the catalyst.

17. The process of claim 13, wherein catalyst (B) is reduced prior to use.

18. The process of claim 1, wherein the contacting in step (e) is performed at about 280° C. to about 350° C.

19. The process of claim 1, wherein the pressure in reactor (B) is between about 1000 psi (6.9 MPa) and about 4000 psi (27.6 MPa).

20. A process for producing alcohols from biomass, the process comprising:
- contacting biomass and methanol with catalyst (A) in reactor (A) under conditions effective to produce an effluent comprising a mixture of alcohols, the conditions in reactor (A) comprising a first temperature;
- contacting at least a portion of the effluent from reactor (A) with catalyst (C) in reactor (C) under conditions effective to produce methanol from carbon monoxide and hydrogen, the conditions in reactor (C) comprising a temperature lower than the first temperature;
- separating the effluent from the reactor (C) into at least two alcohol rich streams and a gas stream comprising carbon monoxide and hydrogen, wherein at least one alcohol rich stream comprises methanol;
- recycling at least a portion of the at least one alcohol rich stream comprising methanol to the reactor (A) and/or a feed to reactor (A); and, one or both of steps i) and ii);
  - i) recycling at least a portion of the gas stream comprising carbon monoxide and hydrogen to the reactor (A) and/or a feed to reactor (A);
  - ii) contacting at least a portion of the gas stream comprising carbon monoxide and hydrogen with catalyst (B) in reactor (B) under conditions effective to produce a methanol-containing product, and subsequently feeding at least a portion of the methanol-containing product to reactor (A) and/or a feed to reactor (A).

21. The process of claim 20, wherein catalyst (C) comprises one or more metals supported on one or more metal oxides.

22. The process of claim 21, wherein the one or more metals comprise one or more of Cu, Pd, Pt, Ni and Ru, and the one or more metal oxides comprise one or more of MgO, CaO, ZnO, SrO, BaO, CeO, $Al_2O_3$, $SiO_2$, $ZrO_2$, and $TiO_2$.

23. The process of claim 22, wherein the one or more metals comprise Cu and the metal oxides comprises ZnO and $Al_2O_3$.

24. The process of claim 23, wherein the amount of Cu in the catalyst is between 5 wt. % and 30 wt. %, and the amount of Zn in the catalyst is between 2 wt. % and 15 wt. %, based on the total weight of the catalyst.

25. The process of claim 21, wherein catalyst (C) is reduced prior to use.

26. The process of claim 20, wherein the contacting with catalyst (C) is performed at about 240° C. to about 300° C.

27. The process of claim 20, wherein the pressure in reactor (C) is between about 1000 psi (6.9 MPa) and about 4000 psi (27.6 MPa).

28. The process of claim 20, wherein, prior to step i) or step ii), the gas stream comprising carbon monoxide and hydrogen is treated to remove at least a portion of carbon dioxide.

29. The process of claim 1, further comprising feeding a make-up stream of carbon monoxide and hydrogen to one or both reactor (A) and reactor (B) and/or a feed to at least one of reactor (A) and reactor (B).

30. The process of claim 29, wherein at least a portion of the make-up stream of carbon monoxide and hydrogen is derived from the gasification of biomass.

* * * * *